United States Patent
Laugharn, Jr. et al.

(10) Patent No.: US 9,320,995 B2
(45) Date of Patent: Apr. 26, 2016

(54) METHOD AND APPARATUS FOR PROCESSING SAMPLE MATERIAL

(71) Applicant: Covaris, Inc., Woburn, MA (US)

(72) Inventors: James A. Laugharn, Jr., Winchester, MA (US); Xiaoyin He, Waltham, MA (US); Srikanth Kakumanu, North Billerica, MA (US)

(73) Assignee: Covaris, Inc., Woburn, MA (US)

( * ) Notice: Subject to any disclaimer, the term of this patent is extended or adjusted under 35 U.S.C. 154(b) by 44 days.

(21) Appl. No.: 14/028,771

(22) Filed: Sep. 17, 2013

(65) Prior Publication Data

US 2015/0079655 A1    Mar. 19, 2015

(51) Int. Cl.
| | |
|---|---|
| B01D 43/00 | (2006.01) |
| G01N 1/34 | (2006.01) |
| G01N 1/38 | (2006.01) |
| C12N 13/00 | (2006.01) |
| A61L 2/10 | (2006.01) |
| B01L 7/00 | (2006.01) |

(52) U.S. Cl.
CPC . *B01D 43/00* (2013.01); *A61L 2/10* (2013.01); *B01L 7/00* (2013.01); *C12N 13/00* (2013.01); *G01N 1/34* (2013.01); *G01N 1/38* (2013.01); *B01L 2200/147* (2013.01); *B01L 2300/0681* (2013.01); *B01L 2300/0832* (2013.01); *B01L 2400/0436* (2013.01); *B01L 2400/0439* (2013.01)

(58) Field of Classification Search
None
See application file for complete search history.

(56) References Cited

U.S. PATENT DOCUMENTS

| | | |
|---|---|---|
| 6,719,449 B1 | 4/2004 | Laugharn, Jr. et al. |
| 6,948,843 B2 | 9/2005 | Laugharn, Jr. et al. |
| 7,521,023 B2 | 4/2009 | Laugharn, Jr. et al. |
| 7,686,500 B2 | 3/2010 | Laugharn, Jr. et al. |
| 7,687,026 B2 | 3/2010 | Laugharn, Jr. et al. |

(Continued)

OTHER PUBLICATIONS

World Health Organization, WHO Technical Report; Series No. 924, Annex 4 "Guidelines on viral inactivation and removal procedures intended to assure the viral safety of human blood plasma products" pp. 150-224 (2004).

(Continued)

*Primary Examiner* — Robert R Raevis
(74) *Attorney, Agent, or Firm* — Wolf, Greenfield & Sacks, P.C.

(57) ABSTRACT

Methods and systems for treating material with focused acoustic energy and/or ultraviolet radiation are described. Sample material may be provided to a single batch vessel or may flow in a continuous or intermittent fashion into/out of a processing chamber within which the material is exposed to focused acoustic energy and/or ultraviolet radiation. Exposure to focused acoustics in a flow through environment may enhance the effects of the radiation on the sample material. Further, in flow-through or single batch arrangements, sample material may be retained exterior to or within a processing chamber by one or more retaining members (e.g., filter, valve, etc.) until a characteristic of the sample material reaches one or more particular criteria (e.g., physical, chemical, biological). Once the criteria of the sample material is attained (e.g., via further treatment), the material is then permitted to flow past the retaining member(s) and through the inlet or outlet of the chamber. Further, focused acoustic processing may be used to treat articles, such as the retaining member(s), rather than only sample material located within an internal processing volume of the chamber.

21 Claims, 30 Drawing Sheets

(56) References Cited

U.S. PATENT DOCUMENTS

| | | |
|---|---|---|
| 7,687,039 B2 | 3/2010 | Laugharn, Jr. et al. |
| 7,757,561 B2 | 7/2010 | Laugharn, Jr. et al. |
| 7,811,525 B2 | 10/2010 | Laugharn, Jr. et al. |
| 7,981,368 B2 | 7/2011 | Laugharn, Jr. et al. |
| 8,263,005 B2 | 9/2012 | Laugharn, Jr. et al. |
| 8,273,253 B2 | 9/2012 | Curran |
| 8,353,619 B2 | 1/2013 | Laugharn, Jr. et al. |
| 8,409,801 B2 | 4/2013 | Laugharn, Jr. |
| 8,459,121 B2 | 6/2013 | Laugharn, Jr. |
| 2002/0009768 A1* | 1/2002 | Chu ............... 435/40.5 |
| 2009/0317884 A1 | 12/2009 | Laugharn, Jr. |
| 2012/0015419 A1 | 1/2012 | Laugharn, Jr. |
| 2012/0024867 A1 | 2/2012 | Laugharn, Jr. |
| 2012/0055264 A1* | 3/2012 | Sinha ............... 73/861.25 |
| 2012/0144905 A1 | 6/2012 | Laugharn, Jr. et al. |
| 2012/0234625 A1 | 9/2012 | Laugharn, Jr. et al. |
| 2012/0325727 A1* | 12/2012 | Dionne et al. ............... 209/155 |
| 2013/0026669 A1 | 1/2013 | Beckett et al. |
| 2013/0155802 A1* | 6/2013 | Beckett et al. ............... 366/108 |
| 2013/0177922 A1 | 7/2013 | Laugharn, Jr. et al. |

OTHER PUBLICATIONS

Lytle et al. "Predicted Inactivation of Viruses of Relevance to Biodefense by Solar Radiation" *J. Virol.* vol. 79(22), pp. 14244-14252 (2005).

Bae et al. "Evaluation of Viral Inactivation Efficacy of a Continuous Flow Ultraviolet-C Reactor (UVivatec)" *Kor. J. Microbiol. Biotechnol.*, vol. 37, No. 4, pp. 377-382 (2009).

Yang et al. Fragmentation of Genomic DNA using Microwave Irradiation, *Journal of Biomolecular Techniques*, vol. 24, pp. 98-103 (2013).

Uvivatec® virus inactivation based on UV-C irradiation, Sartorius Stedim Biotech S.A. 2013 (1 page).

* cited by examiner

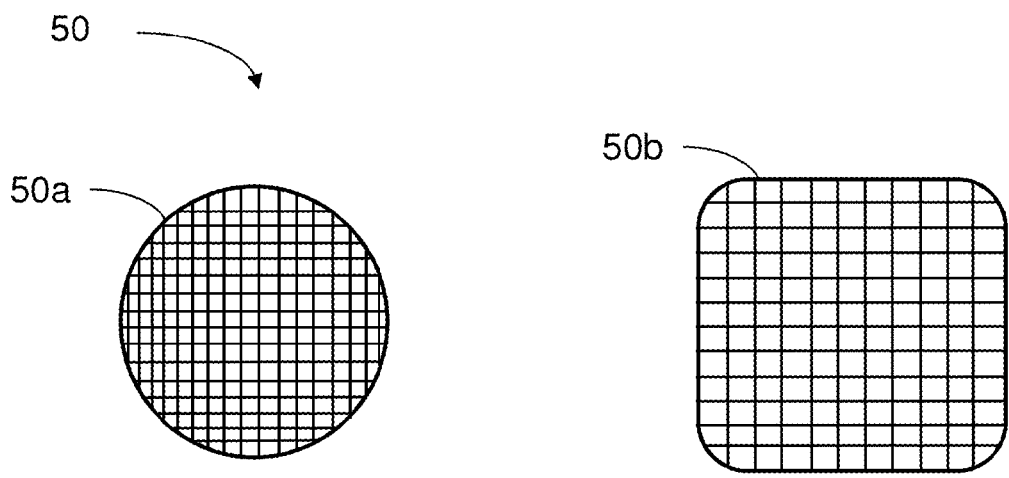
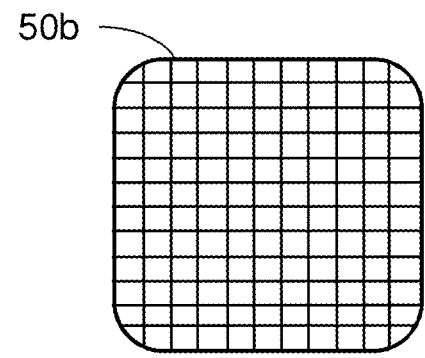
Fig. 2a  Fig. 2b
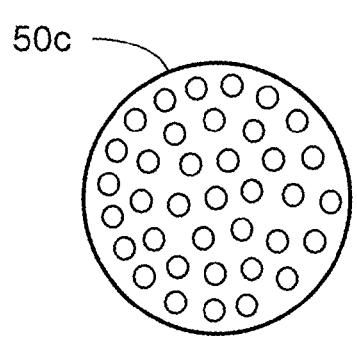
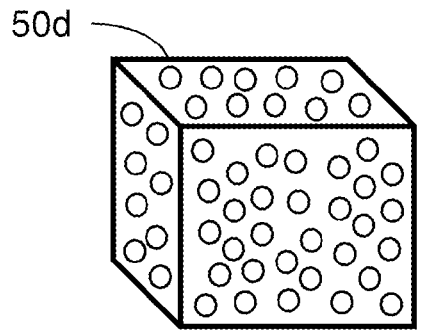
Fig. 2c  Fig. 2d
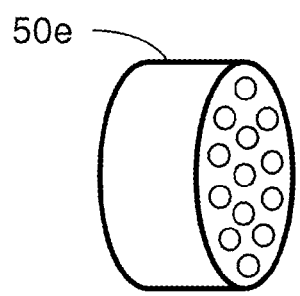
Fig. 2e

METHOD AND APPARATUS FOR PROCESSING SAMPLE MATERIAL

BACKGROUND

1. Field of Invention

Systems and methods for processing samples are generally disclosed.

2. Related Art

Ultrasonics have been utilized for many years for a variety of diagnostic, therapeutic, and research purposes. The acoustic physics of ultrasonics is well understood; however, the biophysical, chemical, and mechanical effects are generally only empirically understood. Some uses of sonic or acoustic energy in materials processing include "sonication," an unrefined process of mechanical disruption involving the direct immersion of an unfocused ultrasound source emitting energy in the kilohertz ("kHz") range into a fluid suspension of the material being treated. Accordingly, the sonic energy often does not reach a target in an effective dose because the energy is scattered, absorbed, and/or not properly aligned with the target. Sonication has also hit limits on effectiveness when applied to higher sample volumes or continuous process streams. There are also specific clinical examples of the utilization of therapeutic ultrasound (e.g., lithotripsy) and of diagnostic ultrasound (e.g., fetal imaging).

However, ultrasonics have heretofore not been controlled to provide an automated, broad range, precise materials processing or reaction control mechanism. In U.S. Pat. No. 7,521,023 and others, the use of 'focused acoustical energy' is described to overcome some of the limitations of traditional 'sonication.' Focusing the acoustical energy has many advantages, and can be effective at processing high sample volumes or continuous process streams through the use of a "processing chamber" through which the sample material passes.

Further, ultraviolet radiation has been used as a method of sterilizing chemical/biological samples and/or bioactive preparations (e.g., pharmaceuticals) that would otherwise be at risk for contamination. However, it has been observed that ultraviolet radiation can cause tissue or protein damage due to overexposure and/or non-uniform delivery.

SUMMARY

In accordance with the present disclosure, a focused acoustic treatment apparatus may be arranged as a continuous flow-through system, for continuous processing of sample material, or as a single batch vessel system. The inventors have recognized and appreciated that it would be advantageous for such an apparatus to be constructed so as to retain sample material within the internal volume, or immediately exterior to the internal volume, of a processing chamber. For instance, a retaining member (e.g., filter, valve, etc.) may be suitably positioned at an inlet or outlet of a processing chamber so as to retain material exterior to or within the internal volume of the chamber, based on whether one or more characteristics of the material meets the criteria.

Accordingly, material that attains the characteristic(s) that meet the predetermined criteria is permitted to flow past the retaining member and through the inlet (into the processing chamber) or outlet (out of the processing chamber). However, material having characteristics that do not meet the appropriate physical, chemical and/or biological criteria is not permitted to flow past the retaining member and through the inlet or outlet.

As an example, when sample material is retained within the internal volume of the processing chamber, the sample material may be subject to focused acoustic treatment, for a period of time, until certain characteristics of the material (e.g., physical, chemical, biological, etc.) meets one or more criteria. Or, sample material may be filtered into the internal volume of the processing chamber prior to acoustic treatment.

A physical criteria may, for example, be based on particle size, where particles of sample material smaller than a threshold particle size may be permitted to flow past, or through, a filter positioned at the outlet of the chamber, while particles greater than the threshold particle size are prevented from flowing past, or through, the filter.

In some embodiments, chemical or biological criteria may be used as primary or secondary criteria for controlling the exit of the sample from the processing chamber. For example, biological and/or chemical sensors may be placed at the exit of a processing chamber to detect the presence or absence of certain chemical compositions (e.g., polymers, small molecules, chemical concentrations, etc.) and/or biological material (e.g., bacteria, viruses, fungi, etc.). Such detection may serve as a process analytical tool for determining whether the processed/treated samples are permitted to exit the processing/reaction chamber, or enter into the processing/reaction chamber.

Material located within the internal volume of the processing chamber may be subjected to focused acoustic energy having a frequency of about 100 kHz to 100 MHz and a focal zone of acoustic energy, where the acoustic energy is generated by an acoustic energy source/transducer spaced from the chamber. Depending on parameters of the focused acoustics and the material itself that is processed, focused acoustic treatment of a material may give rise to a number of different results. For example, focused acoustic treatment described herein may be used for shearing nucleic acids, fragmenting particles, lysing cells, mixing solutions, creating emulsions and/or suspensions, cleaning or otherwise removing material from articles, sterilizing samples, or yielding any other suitable result.

As discussed herein, focused acoustic processing may be optionally used to treat articles other than biological/chemical based sample material located within an internal processing volume of the chamber. For instance, a retaining member that is used to filter sample material, or otherwise act as a gateway for whether certain characteristics of the sample material meets a certain set of criteria, may itself be exposed to focused acoustic energy having a frequency of about 100 kHz to 100 MHz and a focal zone of acoustic energy having a width of less than about 2 centimeters.

In some cases, material may undesirably adhere to or otherwise collect at the retaining member; for example, a filter or valve (e.g., membrane) through which material passes or to which material may adhere, or settle, may become congested and require a cleaning treatment so as to remove the material that impedes or clogs suitable flow through or past the filter or valve. Accordingly, focused acoustic energy may be useful for cleaning or otherwise moving such collections of material from a retaining member so that suitable flow through the retaining member may occur.

The inventors have also appreciated that the effects of certain types of irradiation on samples (e.g., sterilization of samples) may be enhanced, or otherwise increased, when used together with focused acoustic energy. In some embodiments, the material located within the internal volume of the processing chamber may be exposed to irradiation simultaneously, and/or in succession (e.g., alternating), with focused acoustic energy, for example, until the amount of undesirable components, such as infectious microbes, within the sample material, reach a desired threshold amount.

Irradiation may be provided by a source separate from the acoustic energy source, and may serve to treat the material, for example, in a manner complementary to that of the treatment provided by the focused acoustic energy. Or, as discussed above, focused acoustics may serve to enhance the effects of the irradiation. In some embodiments, the irradiation comprises ultraviolet radiation, which may provide a sterilizing treatment for the material.

In one illustrative embodiment, a method of sample treatment is provided. The method includes exposing material located within an internal volume of a chamber to focused acoustic energy having a frequency of about 100 kHz to 100 MHz and a focal zone of acoustic energy in the internal volume; retaining a portion of the material at a region of the chamber based on whether the portion of the material has a characteristic that meets a criterion; and permitting flow of the portion of the material toward or away from the internal volume of the chamber based on whether the characteristic of the portion of the material meets the criterion.

In another illustrative embodiment, a sample treatment apparatus is provided. The apparatus includes a chamber defining an internal volume and having an inlet to receive an inflow of material into the internal volume and an outlet to discharge an outflow of material from the internal volume; an acoustic energy source spaced from the chamber and arranged to emit acoustic energy having a frequency of about 100 kHz to 100 MHz to create a focal zone of acoustic energy in the internal volume; and at least one retaining member constructed and arranged to retain a portion of the material at a region of the chamber based on whether the portion of the material has a characteristic that meets a criterion.

In yet another illustrative embodiment, a method of sample treatment is provided. The method includes exposing material located within an internal volume of a chamber to non-visible electromagnetic radiation and focused acoustic energy having a frequency of about 100 kHz to 100 MHz; and flowing a portion of the material toward or away from the internal volume of the chamber.

In an illustrative embodiment, a sample treatment apparatus is provided. The apparatus includes a chamber defining an internal volume; an acoustic energy source spaced from the chamber and arranged to emit acoustic energy having a frequency of about 100 kHz to 100 MHz to create a focal zone of acoustic energy in the internal volume; and at least one non-visible electromagnetic radiation source housed by the chamber and arranged to emit radiation toward the internal volume.

In another illustrative embodiment, a method of treating an article is provided. The method includes moving material disposed at a retaining member to accommodate flow past the retaining member by exposing the retaining member to focused acoustic energy having a frequency of about 100 kHz to 100 MHz and a focal zone of acoustic energy having a width of less than about 2 centimeters, the retaining member constructed to obstruct movement of a portion of a sample from one side of the retaining member to an opposite side of the retaining member based on whether the portion of the material has a characteristic that meets a criterion.

In yet another illustrative embodiment, a sample treatment apparatus is provided. The apparatus includes at least one retaining member constructed and arranged to retain a portion of the material at a region of the chamber based on whether the portion of the material has a characteristic that meets a criterion; and an acoustic energy source spaced from the at least one retaining member and arranged to emit acoustic energy having a frequency of about 100 kHz to 100 MHz to create a focal zone of acoustic energy having a focal zone of less than 2 centimeters located at a portion of the at least one retaining member.

Other advantages and novel features of the invention will become apparent from the following detailed description of various non-limiting embodiments when considered in conjunction with the accompanying figures and claims.

BRIEF DESCRIPTION OF THE DRAWINGS

Illustrative embodiments of the present disclosure are more particularly described in the following detailed description, taken in conjunction with the accompanying drawings. In the drawings, like reference characters generally refer to the same parts throughout the different views. Also, the drawings are not necessarily to scale, emphasis instead generally being placed upon illustrating principles of the invention.

FIGS. 2a-2e illustrate various views of embodiments of retaining members in accordance with some embodiments;

FIG. 9b depicts another cross-sectional view of the sample treatment apparatus of FIG. 10a;

FIG. 10b illustrates a cross-sectional view of the apparatus of FIG. 10a;

FIG. 10c depicts a close up perspective view of a portion of the apparatus of FIG. 10a;

FIG. 10d shows another close up perspective view of a portion of the apparatus of FIG. 10a;

DETAILED DESCRIPTION

Figure 1A:
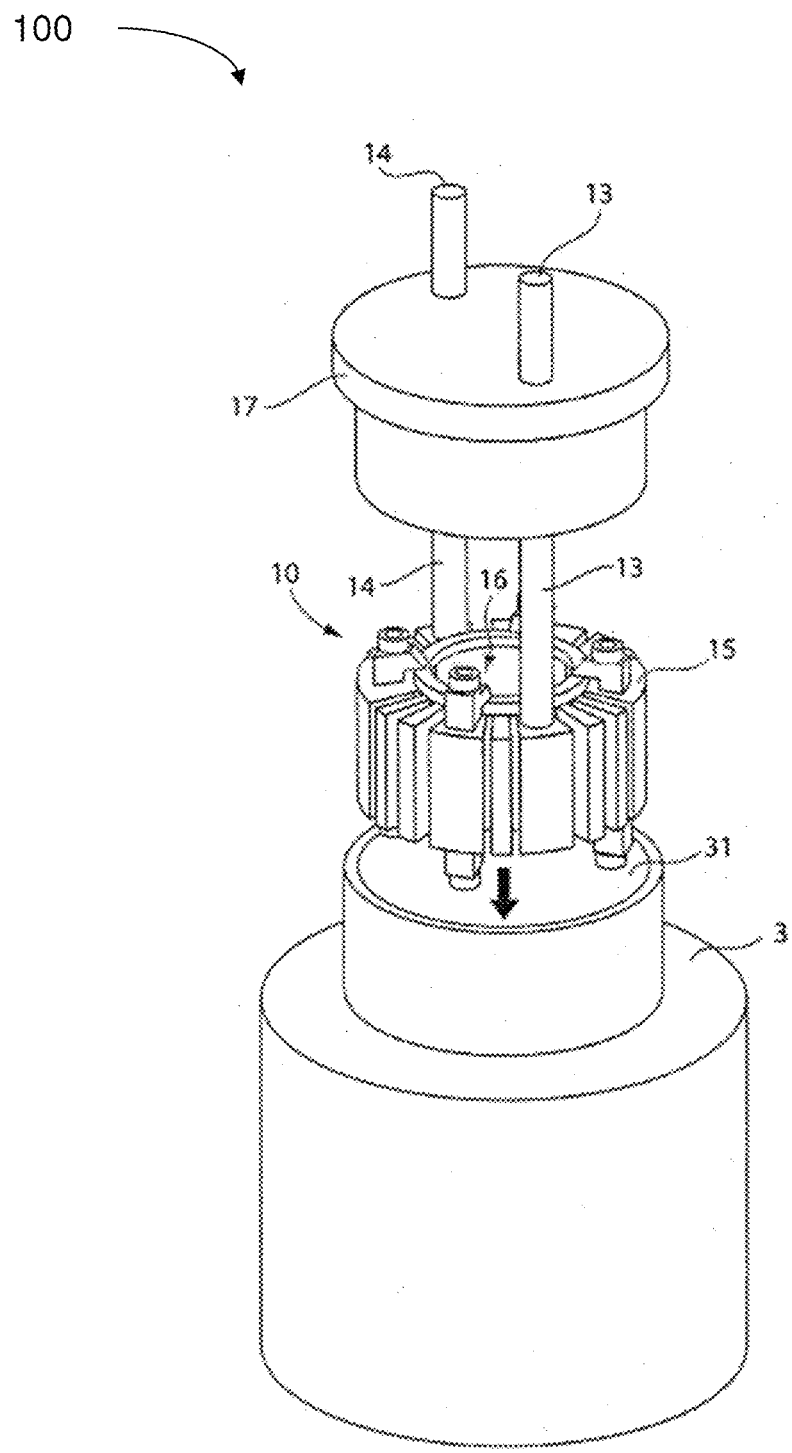
FIG. 1a is an exploded perspective view of a sample treatment apparatus in accordance with some embodiments.

"Sonic energy" as used herein is intended to encompass such terms as acoustic energy, acoustic waves, acoustic pulses, ultrasonic energy, ultrasonic waves, ultrasound, shock waves, sound energy, sound waves, sonic pulses, pulses, waves, or any other grammatical form of these terms, as well as any other type of energy that has similar characteristics to sonic energy. "Focal zone" or "focal point" as used herein means an area where sonic energy converges and/or impinges on a target, although that area of convergence is not necessarily a single focused point, but may include a volume of varying size and shape. As used herein, the terms "process chamber," "processing chamber" or "processing zone" as used herein means a vessel or region where the sonic energy converges, and the sample material is present for treatment. As used herein, "nonlinear acoustics" can mean lack of proportionality between input and output. For example, as the amplitude applied to the acoustic transducer increases, the proportionality of the sinusoidal output may decrease such that eventually the peak positive pressure increases at a higher rate than the peak negative pressure. Also, water may exhibit nonlinear behavior at high acoustic energy intensities, and in a converging acoustic field, the waves may become more disturbed as the intensity increases toward the focal point.

Nonlinear acoustic properties of tissue can be useful in diagnostic and therapeutic applications. As used herein, "acoustic streaming" can mean generation of fluid flow by acoustic waves. Such an effect can be non-linear. Bulk fluid flow of a liquid in the direction of the sound field can be created as a result of momentum absorbed from the acoustic field. As used herein, "acoustic micro-streaming" can mean time-independent circulation that occurs only in a small region of the fluid around a source or obstacle, for example, an acoustically driven bubble in a sound field. As used herein, "acoustic absorption" can refer to a characteristic of a material relating to the material's ability to convert acoustic energy into thermal energy. As used herein, "acoustic impedance" can mean a ratio of sound pressure on a surface to sound flux through the surface, the ratio having a reactance and a resistance component. As used herein, "acoustic window" can mean a system or device for allowing sonic energy to pass through to the sample within the processing chamber or zone. As used herein, "acoustic lens" can mean a system or device for spreading, converging or otherwise directing sounds waves. As used herein, "acoustic scattering" can mean irregular and multi-directional reflection and diffraction of sound waves produced by multiple reflecting surfaces, the dimensions of which are small compared to the wavelength, or by certain discontinuities in the medium through which the wave is propagated.

Systems of the present disclosure may be used for a number of different types of focused acoustic processing of a sample, such as for mixing, sterilization, particularization, cell lysis, reaction enhancement and/or DNA/RNA shearing, e.g., to reduce the base pair length of DNA fragments from 1,000 s or 10,000 s of base pairs to lengths of 3 k base pairs or smaller, in a reproducible and high-yield manner. Systems described herein may provide acoustic treatment involving focused acoustic energy having a frequency of about 100 kHz to 100 MHz. The acoustic energy may have a focal zone that has a width of less than 2 cm. Examples of such acoustic treatment systems and control arrangements are described in U.S. Pat. Nos. 6,948,843 and 6,719,449, assigned to Covaris of Woburn, Mass., appropriate aspects of which may be incorporated in systems described herein.

Systems of the present disclosure may be used in single batch arrangements as well as flow through arrangements, where an inlet is provided for supplying sample material to a processing chamber and an outlet is provided to accommodate exit of treated sample material from the processing chamber. Flow through arrangements may allow for continuous focused acoustic processing of large volumes of sample material where sample material may be circulated and, in some cases, recirculated, through the processing chamber without interruption; although, in some cases described herein, sample material may be retained within the processing chamber until a certain characteristic the material meets one or more criteria (e.g., physical, chemical, biological, etc.). Examples of flow through arrangements that involve focused acoustic processing and control are described in U.S. Pat. No. 8,459,121, assigned to Covaris of Woburn, Mass., appropriate aspects of which may be incorporated in systems described herein.

In accordance with aspects of the present disclosure, single batch systems and continuous flow through arrangements that incorporate focused acoustic processing may employ one or more retaining members (e.g., filter, valve, etc.) for retaining sample material immediately exterior to or within the processing volume of a chamber in which focused acoustic treatment occurs, unless or based on whether a characteristic of the sample material meets one or more criteria or threshold characteristic(s). Once the sample material, or a portion thereof, meets the criteria (e.g., sample particles having a particle size smaller than a threshold size, sample solution having a transmittance greater than a threshold transmittance, sample material having a certain chemical/biological composition, sample material exhibiting a particular set of properties, absence or presence of particular biological material, etc.), then that portion of the sample material which meets the criteria is then permitted to enter the processing volume through an inlet, or alternatively, exit the processing volume through an outlet.

Accordingly, rather than a sample material flowing through an inlet into a process chamber for treatment and then immediately out of the chamber through an outlet, the sample material may be subject to a suitable degree of control, for example, how much treatment the sample material receives, and for how long, prior to exit out of the chamber. For instance, despite the chamber having a number of inlets and outlets, portions of the sample material processed in the flow through system may be substantially held in place, or kept contained within a confined space, and exposed to treatment within the chamber for extended periods of time, until the portion(s) of sample material exhibit characteristics that meet the criteria for permitting the portion(s) of sample material to exit the confined space. Or, depending on whether suitable criteria is met, portions of sample material may be obstructed from entering into the processing chamber, even prior to focused acoustic or irradiation treatment.

In addition to being subject to focused acoustic energy, material located within the internal volume of a processing chamber may be exposed to a suitable type and degree of electromagnetic irradiation (e.g., non-visible electromagnetic radiation, such as ultraviolet radiation, infrared radiation and/or microwave radiation). In some embodiments, such irradiation includes ultraviolet radiation, which has a wavelength shorter than that of visible light, but longer than X-rays; e.g., having a wavelength range between 10 nm and 400 nm. In some embodiments, irradiation includes microwave radiation, which has a wavelength longer than that of visible and infrared light; e.g., having a wavelength range between 1 mm and 1 m. For example, microwave irradiation may be used, at times, in cooperation with thermal heating, to fragment nucleic acids to size ranges suitable for sequencing.

Ultraviolet irradiation may employ a radiation wavelength and intensity that is appropriate for sterilizing sample material (e.g., killing cells, viruses, organisms, etc.) located within the processing chamber. Accordingly, in some embodiments, sample material with properties that do not meet one or more desired criteria (e.g., particles are not small enough to pass through a filter and exit the chamber via an outlet, sample material has not yet reached a desired level of sterilization or other physical/chemical/biological property and so are not permitted to exit the chamber, etc.) may be retained within the internal volume of the flow through process chamber and, while present within the processing volume, may be subject to focused acoustic treatment and/or ultraviolet radiation. It can be appreciated that irradiation in accordance with aspects of the present disclosure may include any suitable electromagnetic radiation, such as X-rays, gamma rays, infrared radiation, visible light, non-visible, electromagnetic radiation, microwave radiation, etc.

In some applications, it may be preferred, or required, that clinical preparations of biopharmaceuticals or bioactive agents derived from plasma, cell lines, blood samples, or tissues of human or animal origin be sterilized or otherwise free from contamination, or risk of contamination. Accordingly, in some embodiments, the system includes one or more suitable electromagnetic radiation sources (e.g., low-pressure mercury-vapor lamp for emitting ultraviolet radiation) that is effective for sterilizing material upon a sufficient degree of exposure. For example, the type of ultraviolet radiation emitted may fall within the Ultraviolet C (UVC) subtype category. In general, UVC radiation has a wavelength range of between 100-280 nm (energy per photon 4.43-12.4 eV) and energy output of between 5-200 J/m$^2$, or other parameter(s) known in the art, and is typically employed to kill microorganisms, such as bacteria, viruses, fungi, and others.

In some cases, the germicidal or virucidal nature of ultraviolet irradiation may be quite effective at wavelengths of between approximately 185 nm and 265 nm (e.g., 185 nm, 254 nm, 265 nm), particularly for inactivating viruses. Ultraviolet radiation within this wavelength range may be effective to degrade nucleic acids and, with a sufficient amount of exposure, is able to render a wide variety of viruses inactive. In some instances, while not necessarily the case in every situation, viruses that contain single-stranded nucleic acids may be more sensitive to ultraviolet radiation than viruses with double-stranded nucleic acids. This is due to the lack of a complementary strand in single-stranded nucleic acids, which results in an inability to repair damaged DNA/RNA. In some cases, as genome size increases, thereby increasing the overall likelihood of exposure to external effects/treatment (e.g., radiation, or other types of treatment), the sensitivity of a virus to ultraviolet radiation may also increase accordingly.

While ultraviolet irradiation may be effective as a sterilization treatment for sample materials, there is also potential for protein and/or tissue damage to arise in ultraviolet irradiated samples, for example, due to overexposure and/or delivery of non-uniform doses. However, where ultraviolet radiation (or another type of radiation) is employed, the use of a continuous flow system incorporating focused acoustic treatment may provide for an elevated level of mixing and uniformity of microorganism/virus exposure to the radiation.

In some embodiments, the effects of irradiation (e.g., sterilization through ultraviolet radiation) on a sample may further be enhanced when the sample is also exposed to focused acoustic energy. As such, for some embodiments, a sample treatment system is provided with one or more irradiation sources (e.g., ultraviolet irradiation at 185 nm, 254 nm, 265 nm wavelengths, etc.) in cooperation with focused acoustic energy in a continuous flow through or single batch arrangement. Such a system may be used for the preparation of a number of biological formulations (e.g., vaccines, blood and plasma products, bioactive agents, proteins and enzyme extracts, fermentation media, therapeutic proteins, etc.) while being able to maintain the integrity of the biological system (i.e., without resulting damage to the sample material). It can be appreciated that any appropriate number and type of electromagnetic radiation sources may be used, based on the application(s) for which the sample material is prepared.

In some embodiments, the retaining member itself, or another suitable article, may be subjected to focused acoustic processing and/or electromagnetic irradiation. For instance, a retaining member may be cleared of any unwanted material that might have a tendency, with use, to collect within, adjacent to, or around the surface of the retaining member. Or, such material may simply be rearranged/moved on the surface of the retaining member. In some embodiments, focused acoustic energy may be used to clean a filter, or valve, that has been clogged with residual material or debris remaining on its surface.

For a filter, once such residual material or debris is removed from the surface, or moved to another location, the filter is better able to function by effectively filtering out particles having a size smaller than the threshold particle size from particles having a size greater than the threshold particle size. For a valve, upon movement or agitation of residual material or debris, when actuated to an open position, the valve, which might otherwise be clogged, is able to accommodate flow through of sample material having characteristics that exhibit the desired flow through criteria.

Figure 1B:
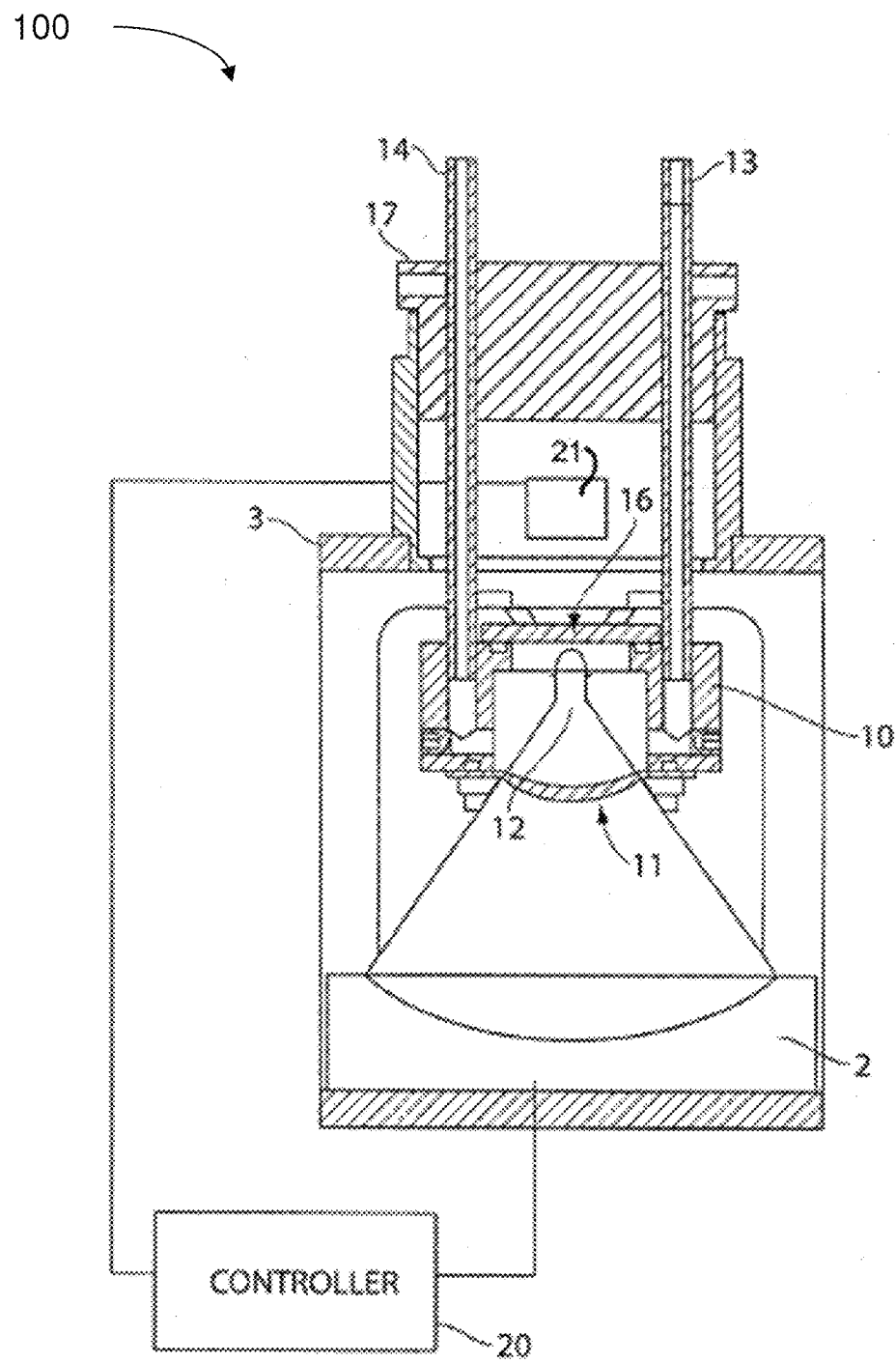
FIG. 1b is a cross-sectional view of the FIG. 1a embodiment in an assembled condition.

FIGS. 1a-1b depict an embodiment of a sample treatment system 100 including a processing chamber 10, where focused acoustic energy generated by an acoustic energy source 2 passes through an acoustic window 11 of the chamber and into an internal volume 12 of the chamber 10 where the sample material is located. A radiation source (not shown in FIGS. 1a-1b) may also be included for providing radiation treatment to the sample material. As is discussed in more detail below, the sample treatment system 100 may include a controller 20 (e.g., including a suitably programmed general purpose computer or other data processing device) that receives feedback and control information (e.g., from one or more sensors, user input devices, etc.) and correspondingly controls operation of the acoustic energy source 2 and/or other system components. Optionally, sample material is provided into the internal volume 12 via an inlet 13 and is removed from the volume 12 via an outlet 14.

The inlet and outlet may be arranged in a variety of ways, and in this embodiment the inlet 13 and outlet 14 each include a conduit coupled to the chamber 10. In some embodiments, the inlet and/or outlet may include a check valve, one-way valve, electronically-controlled valves or other arrangements that help to ensure that flow occurs in a desired way, e.g., so the flow of material runs from the inlet to the outlet, although, in some cases, flow may be intermittent. The internal volume 12 may be sized and shaped as appropriate for the material to be treated, e.g., some acoustic treatment applications (such as sterilization) may function more effectively if a relatively small volume of material is treated within a relatively small processing volume, whereas other applications (such as mixing) may produce better results using a larger volume for the internal volume 12.

The internal volume 12 can have different shapes or other configuration characteristics, e.g., the internal volume 12 may be defined by vertical walls, can have a conical shape, can have a curved shape, and so on. Also, the chamber 10 can be made of multiple components such as an upper member, lower acoustically transparent member, and a body which together define the internal volume that contains the material to be treated. Alternatively, the chamber 10 may be made as a single unitary piece or in other ways.

One or more walls of the chamber 10 may serve as, or otherwise be associated with, a thermal transfer mechanism, or heat exchanger, to dissipate any heat generated in the internal volume 12 and/or to receive heat from outside of the chamber 10 that is transferred into the internal volume 12. As can be seen in FIG. 1*a*, the chamber 10 may include a heat exchanger 15 in the form of a plurality of radial fins. Of course, the heat exchanger 15 could be formed in other ways, such as including a Peltier device that uses electrical power to transfer heat from one location to another, an electric resistance heater, heat conducting rods, tubes or other structures, phase-changing materials used to transfer heat from one location to another, and so on.

The heat exchanger 15 may be arranged to operate with any suitable thermal coupling medium, such as air or other gas, water or other liquid, or a solid material. For example, as shown in FIG. 1*b*, the chamber 10 may be completely or partially submerged in a liquid that serves to transmit heat with respect to the heat exchanger 15. Close thermal coupling between water or other outside thermal coupling medium and the internal volume 12 may help control of the temperature of the material in the internal volume 12 during acoustic processing. Control of the temperature of the coupling medium 4 can help control temperature in the internal volume 12. For example, the coupling medium 4 can be recirculated through a chiller, a heater, or other means to adjust the temperature of the coupling medium 4. Thus, the sample material inside the chamber 10 can be thermally linked to the coupling medium 4 temperature by careful consideration of the design of the chamber 10.

The thermal coupling between the inside wall of the chamber 10 and the sample material may be tightly linked, due to high mixing, turbulence, and activity at the surface of the internal wall, thus creating high convective heat transfer. Heat can pass either through one or more ends of the chamber 10 (e.g., at the windows 11 and 16), or through the side walls of the vessel before being linked to the coupling medium 4 bulk temperature. It is noted that heat can flow in either direction, depending on the relative difference between the coupling medium and the sample material temperature, and the desired target of maintaining the sample at a target temperature to achieve a desired effect.

Heat transfer between the chamber 10 internal wall and the coupling medium can be achieved by simple conduction through the wall to the outside surface, or the external surface area can be enhanced through the use of fins or other high heat transfer effects such as a jacketed vessel with pumped fluid. For example, a jacket may be positioned around at least part of the chamber 10 and a thermal transfer medium may be circulated in the space between the jacket and the chamber 10 external wall. In addition, inlet and/or outlet conduits can also be coupled to the coupling medium temperature and/or the thermal transfer medium by the use of enhanced thermal surfaces at the inlet, or outlet of the chamber 10. For example, although not shown in the figures, the inlet 13 and/or outlet 14 may pass through a space between the jacket and the chamber 10 so as to transfer heat with respect to the thermal transfer medium. Alternatively, the inlet and/or outlet medium conduit may include heat exchanger features that allow heat to be transferred with respect to the acoustic coupling medium 4.

In certain embodiments, the acoustic energy source 2 may include an ultrasound transducer that projects a focused ultrasound beam or wave front toward the window 11 of the chamber 10. The window 11, which may sealingly close an opening in the chamber 10, may be suitably transparent to, or otherwise transmit acoustic energy so that the ultrasound beam penetrates the window 11 to form a focal zone within the internal volume 12 that acts upon the material in the chamber 10. The window 11 may be configured to transmit a substantial amount of ultrasound energy from the acoustic source 2 to the material in the chamber 10, minimize the absorption of ultrasound energy within the walls of the chamber 10, and/or maximize heat transfer between the internal volume 12 and, for example, an external water bath or other coupling medium.

In certain embodiments, the window 11 is glass, sapphire, quartz, a polymer such as a thin film polymer such as a polyimide (e.g., Kapton®), or thin sheet of metal (e.g., stainless steel). The window may have any suitable shape or other configuration, e.g., may be flat (or otherwise present a relatively flat surface to the impinging acoustic energy), or may be curved so as have a hemispherical or other convex shape. In certain embodiments, the window 11 is shaped to guide the sonic energy in a preferred manner relative to the internal volume 12, such as focusing or defocusing the acoustic energy, through a 'lens' effect caused by the physical shape of the window 11 (such as an effect caused by a concave or convex shape).

In some embodiments, the window 11 has an acoustic impedance similar to that of water and a relatively low acoustic absorption. One suitable material is low density polyethylene, but other polymers such as polypropylene, polystyrene, poly(ethylene terephthalate) ("PET"), polyimide (e.g., Kapton®), and other rigid and flexible polymers may be used. In some embodiments, the window 11 exhibits a substantial difference in acoustic impedance compared with water, for example stainless steel, but it is thin (e.g., one or more orders of magnitude thinner than the wavelength of acoustic energy transmitted within the material. In such cases, the acoustic attenuation (e.g., both reflection and absorption) may be small, or negligible. Thus, a sufficient amount of acoustic energy may propagate into the internal volume 12.

If the window 11 is formed from a thin film material, the film may be a laminate to facilitate thermal bonding to the chamber 10. For example, the window 11 may be sealingly attached to the chamber 10 using heat sealing. Thicker, more rigid materials may also be employed for the window 11. In some embodiments, while the window 11 may be acoustically transparent, such a window may resist transmission of a particular type of radiation (e.g., ultraviolet) therethrough. Accordingly, both focused acoustic energy and electromagnetic radiation may be retained within the internal volume 12 of the chamber so as to enhance the overall treatment effects of each, as well as the combined effect of both.

The upper portion of the chamber 10 may include an inspection window 16, which can be flat or domed or otherwise arranged to enclose the internal volume 12 while permitting visible light inspection of the internal volume 12. Such inspection may be done by a human, or by a suitably arranged sensor 21 such as a video camera, photodetector, IR detector, and so on. Characteristics of the material in the internal volume 12 detected by the sensor 21 may be used by the controller 20 to control the acoustic energy source 2 or other components of the system 100. For example, if excessive cavitation is to be avoided, the controller 20 may adjust the acoustic energy at the focal zone if the sensor 21 detects the presence of cavitation bubbles of a certain size and/or number. Or, if exposure of the sample material to ultraviolet radiation is too great, then the controller 20 may adjust the intensity of ultraviolet radiation emitted into the internal volume of the chamber. Conversely, if the intensity of ultraviolet radiation emitted from a radiation source is too small, then the controller may send a signal to make the appropriate adjustment.

Other features may be detected by the sensor 21, such as the size, density or other characteristics of particles in the chamber 10 in the case, for example, where the acoustic treatment is intended to break down the size of particles in the sample material. The sensor may be useful to detect other characteristics of the sample as well, such as transmittance, degree of mixing, degree of sterilization of the sample, chemical or biological composition of the sample (e.g., chemical sensor, biosensor, etc.), concentration of materials, bubble formation, whether an emulsion/suspension has resulted, or other suitable features.

For instances where the acoustic treatment is used to break apart or otherwise mix parts of cells, the sensor may be employed to detect appropriate characteristics. Thus, the sensor 21 may detect whether acoustic and/or irradiation treatment is progressing as desired and whether processing is complete, e.g., to trigger the introduction of additional sample material into the chamber 10, or force sample material to exit the processing chamber. Like the window 11, the inspection window 16 may be formed of any suitable material, such as glass, sapphire, quartz, plastic and/or polymer materials.

The body of the chamber 10 may be made of any material or combination of materials suitable to contain the material in the internal volume 12 during treatment, to act as an environmental seal, and/or to provide a thermal transfer mechanism. In some embodiments, the chamber 10 may be made of a rigid or flexible material, such as a thermally conductive metal (e.g., stainless steel, aluminum, etc.) or polymer, or a combination of such materials. Preferably, the material used for the chamber 10 has a low acoustic absorption and acceptable heat transfer properties for a desired application.

In certain embodiments, the upper portion of the chamber 10 (e.g., including the inspection window 16) can be arranged to reflect acoustic energy back into the internal volume 12, providing for additional process efficiencies. If the chamber 10 is made from multiple parts, such as by upper and lower members, the members may be joined together by thermal bonding, adhesive bonding, external clamping, mechanical fasteners (such as the bolts shown in FIG. 1a) with an o-ring or other gasket to form a seal between the members, welding, and so on. If the bond is to be achieved by thermal bonding, the upper and lower members may be made of, or include, film laminates having heat bondable outer layers and heat resistant inner layers.

As can be seen in FIG. 1b, the sample treatment system 100 may include a vessel 3 that contains the acoustic energy source 2, the chamber 10 as well as a coupling medium 4. The vessel 3 may take any suitable size, shape or other configuration, and may be made of any suitable material or combination of materials (such as metal, plastic, composites, etc.). In this illustrative embodiment, the vessel 3 has a jar- or can-like configuration with an opening 31 arranged to permit access to an internal volume of the vessel 3. The acoustic energy source 2 and the coupling medium 4 (such as water or other liquid, or optionally a solid material) may be positioned in the vessel 3, e.g., with the acoustic energy source 2 near a bottom of the vessel 3.

In some embodiments, if the coupling material 4 is solid, the vessel 3 and the coupling medium 4 may be essentially integrated with each other, with the coupling medium 4 essentially functioning as an acoustic coupling as well as a physical attachment of the acoustic source 2 and the chamber 10. An opening 31 may be provided and arranged so that the chamber 10 can be lowered into the vessel 3, e.g., so that the chamber 10 is partially or completely submerged in the coupling medium 4. The coupling medium 4 may function as both an acoustic coupling medium, e.g., to transmit acoustic energy from the acoustic energy source 2 to the window 11, as well as a thermal coupling medium, e.g., to accept heat energy from the chamber 10. In other embodiments, the thermal and acoustic coupling medium may be separate, e.g., where the chamber 10 is provided with a cooling jacket.

In this illustrative embodiment, the opening 31 is sized and shaped to receive the chamber 10, which has a barrel shape in this embodiment with the inlet 13 and outlet 14 extending generally along the longitudinal axis of the barrel shape of the chamber 10. A cap 17 is engaged with the inlet 13 and outlet 14 conduits and is arranged so that the chamber 10 may be suspended in the coupling medium 4, supported by the inlet and outlet conduits and the cap 17. The chamber 10 may be positioned in the vessel 3 so that a focal zone of acoustic energy created by the acoustic energy source 2 is suitably located in the internal volume 12 of the chamber 10.

Thus, assembly of the system 100 may be eased because appropriate positioning of the chamber 10 relative to the acoustic energy source 2 may be achieved by simply engaging the cap 17 with the opening 31 of the vessel 3. No adjustment of the chamber 10 position in the vessel 3 need be required as long as the chamber is suitably positioned relative to the cap 17 and the cap 17 is properly engaged with the vessel 3. The cap 17 may engage with the opening 31 of the vessel 3 so that not only the cap 17/chamber 10 are supported by the vessel 3, but also so that the vessel opening 31 is sealed or otherwise closed by the cap 17, e.g., to help prevent contamination of the coupling medium 4. The inlet and outlet conduits may pass through the cap 17, e.g., for fluid connection to supply and/or return lines or other conduits that carry the material to be treated in the chamber 10.

It should be understood that the chamber 10 may be arranged in any suitable way, and for a variety of different applications. For example, in the embodiment shown in FIG. 1b, the inlet 13 and outlet 14 communicate with the internal volume 12 on opposite sides of the volume 12 and at a same vertical level. However, the inlet 13 and outlet 14 may communicate with the internal volume 12 in other ways, e.g., the inlet 13 may be fluidly coupled with the internal volume 12 at a location that is above, or below, a location where the outlet is fluidly coupled to the internal volume.

Having the inlet and outlet coupled at different heights may provide advantages depending on the specific application. For example, in some applications, having the inlet located above the outlet may help control the temperature of the material in the internal volume 12, e.g., cooler fluid entering at the inlet may mix with relatively warm fluid near a top of the internal volume 12. In other applications, having the inlet below the outlet may help ensure that material having a desired size or density is encouraged to exit at the outlet, e.g., larger, more dense particles may remain in the internal volume 12 below the outlet until the particles are broken down by the acoustic treatment into a desired size/density range. In the case of a water jacketed chamber, positioning the inlet and outlet at opposite ends of the chamber can enable counterflow heat exchanger operation and improved heat transfer and temperature control of the sample.

FIGS. 2a-2e show various embodiments of retaining members 50 that may be employed with sample treatment systems described herein. In some embodiments, and as shown, retaining members 50a, 50b, 50c, 50d, 50e may be provided and used as filters. Accordingly, retaining members 50a, 50b, 50c, 50d, 50e may be porous filters, having openings that allow particles of a particular size to pass through the filter from one side to another, allowing for size exclusion. That is, the filter may be constructed to have openings of a certain shape and size to define a threshold particle size such that particles of an appropriate shape and having a particle size that is smaller than the threshold particle size are permitted to flow through the filter via one or more of the openings. On the other hand, particles having a shape and particle size that do not allow for the particle(s) to flow through the holes of the porous filter (e.g., particle size is larger than the threshold particle size of the filter) are prevented from passing through the filter.

In some instances, retaining members may be useful to keep unwanted portions of sample material, such as contaminants, microbes, etc., within the processing chamber. Accordingly, sample material that exits the processing chamber may be more pure than upon first entry into the chamber. Alternatively, retaining members may be useful to keep unwanted portions of sample material outside of the processing chamber.

Retaining members may be constructed in any suitable manner. In some embodiments, retaining members, such as filters 50a, 50b, include a sieve-like mesh. In some embodiments, retaining members, such as filters 50c, 50d, 50e, include sponge-like openings and holes that run through the filter. It can be appreciated that retaining members may incorporate any suitable structure. In some cases, retaining members may have features that effectively lower the nucleation or cavitation threshold of the sample material within the processing chamber.

Retaining members, such as filters, may include any suitable material. In some embodiments, retaining members may include a membrane (e.g., porous membrane), polymer (e.g., polyethersulfone, polyimide, polyester, polystyrene, polyether, polyvinyl alcohol, polysulfone, polyether sulfone, polyacrilonitrile, polyamide, polyethylene, polypropylene, polytetrafluoroethylene, polyvinylidene fluoride, polyvinylchloride, etc.), cellulose (e.g., cellulose acetate, nitrocellulose, cellulose esters, etc.), glass, or another appropriate material. For example, a 0.22 micron polyethersulfone size exclusion filter may be employed in various embodiments of sample treatment systems described herein.

In some embodiments, retaining members may be formed of a material that allows for an appropriate seal to be formed between the retaining member and the inlet/outlet of the processing chamber. Alternatively, in some cases, a sealing material (e.g., o-ring, silicone filler, etc.) may be provided between the retaining member and the entrance, or other portion, of the inlet/outlet so as to ensure that any sample material that flows through the inlet/outlet also flows through the retaining member. It should be understood that retaining members may include any appropriate material, or combination of materials.

Retaining members may exhibit any appropriate shape that may be appropriate for positioning of the filter so as to suitably engage with the outlet of the processing chamber. For example, a retaining member may be shaped so as to accommodate flow of sample material from the internal volume of the processing chamber toward the outlet. In some embodiments, the retaining member may be structured so as to cover the entrance, or other portion, of the inlet/outlet. For example, as discussed above, the retaining member may be shaped so as to be able to form a seal with the perimeter of a portion (e.g., mouth) of the inlet/outlet. Accordingly, in some cases, any sample material, after having been appropriately treated, exiting the processing chamber through the outlet must suitably pass through the retaining member. As shown in FIGS. 2a-2e, on cross-section, filters 50a, 50c, 50e have generally round shapes (e.g., spherical, ellipsoidal, cylindrical, etc.); and filters 50b, 50d have generally square/rectangular cross-sections.

As discussed further below, retaining members may include a valve arrangement (e.g., one-way valve, check valve, two-way valve, electromechanically actuated valve, feedback based valve, etc.) that allows material to flow through the valve when the valve is placed in an open position, and prevents material from passage through the valve when the valve is placed in a closed position. The valve may be actuated by a controller 20 based on sensor feedback information provided to the valve and/or the controller.

It can be appreciated that retaining members are not required to prevent particles of sample material from exiting the internal volume of the processing chamber through physical contact, such as via a physical barrier. For example, if particles of the sample material have magnetic properties, in some embodiments, the retaining member(s) may also have magnetic properties that, at certain times, serve to keep particles that are affected by a magnetic field within the internal volume of the chamber; and, at other times, allow the particles to exit the chamber.

If particles of a sample material do not exhibit the criterion or threshold characteristic that would otherwise permit, or serve as a signal to permit, the particles to enter or exit the chamber, then a retaining member may be oriented, or positioned, so that the particles of the sample material are caused (e.g., forced) to remain within the internal volume of the processing chamber. For example, a magnetic retaining member may be positioned close to the inlet/outlet of the chamber so as to attract and retain particles that exhibit a magnetic response. Conversely, if the particles of the sample material do exhibit a criterion, such as a physical criterion, that would permit, or provide the signal to permit, the particles to enter or exit the chamber, then the retaining member may be oriented, or positioned, in a manner that allows the particles of the sample material to enter or exit the processing chamber.

Figure 3:
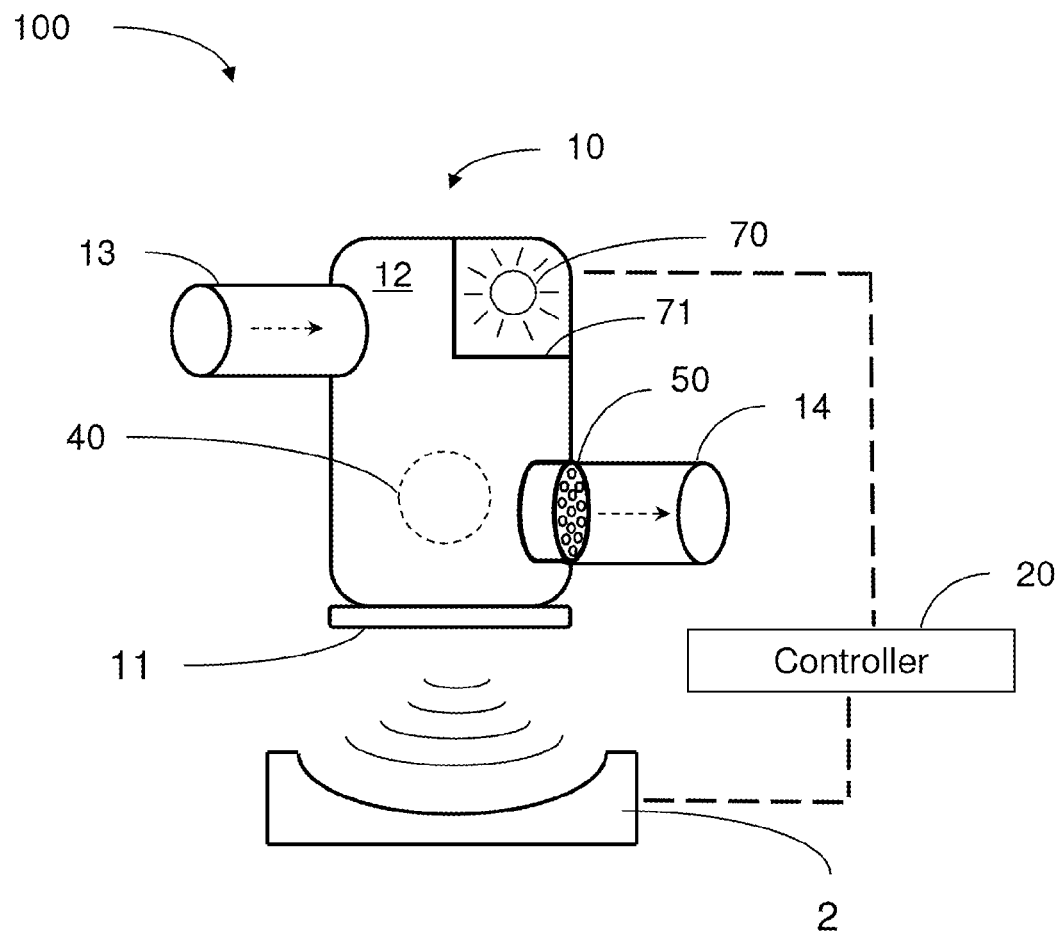
FIG. 3 depicts a schematic view of a sample treatment apparatus in accordance with some embodiments.

FIG. 3 shows an embodiment of a sample treatment system 100 that includes an inlet 13 for accommodating flow of sample material into a processing chamber 10 and an outlet 14 for allowing the sample material to flow out of the processing chamber. A size exclusion filter 50 having a number of openings that are substantially uniform in size and shape is positioned at the mouth of the outlet 14 such that any material that exits the processing chamber would also pass through the filter.

In some embodiments, as long as the filter, or other retaining member, keeps the sample material within the internal volume of the chamber, the sample continues to be processed, whether by focused acoustic energy and/or by irradiation (e.g., UVC radiation). Thus, whatever portion of the sample material does not reach or otherwise exhibit characteristics that satisfy the particular criterion for permitting passage through the retaining member is held within the internal volume for further processing. For example, as long as the criterion is not attained, the sample material may be continuously exposed within the internal volume of the chamber to focused acoustic energy and/or irradiation for possible time periods of greater than 1 minute, 2 minutes, 5 minutes, 10 minutes, 30 minutes, 60 minutes, and so on, until the criterion or some threshold characteristic is reached. In some cases, sample material is exposed to focused acoustic energy and/or radiation treatment for an extended, or indefinite, period of time, until the controller, or operator, alters the treatment plan or criterion that would allow the sample material to exit the chamber via an outlet.

The system 100 also includes a radiation source 70 for emitting ultraviolet radiation, or another type of radiation, into the internal volume of the processing chamber. In some embodiments, while not expressly shown in the figures, the system may include multiple sources capable of emitting different types of radiation (e.g., having different wavelengths, intensity, etc.) so as to provide a suitable combination of radiation emitted toward the sample. Further, multiple radiation sources may be optionally contained or otherwise housed within one or more corresponding chambers.

In some embodiments, the radiation source 70 is located behind a window 71. The window 71 may provide protection for the radiation source 70 so that the source does not come into direct contact with the sample material. As the sample material may be biological in nature, with soft tissue and other particles, it may be preferable for the sample material not to collect at the radiation source, and possibly adhering to the source itself, which may diminish the effectiveness of the emitted radiation. The window 71 may further be transparent or translucent so as to transmit radiation emitted from the source 70 through the window and toward the internal volume 12 of the chamber.

The window 71 may include any suitable material that is transparent or translucent so as to allow transmission of radiation therethrough, for example, glass, thin film polymers, moldable polymers, quartz, sapphire, other suitable materials, or combinations thereof. In some embodiments, the window 71 includes nucleation sites, such as geometrical protrusions or features (e.g., less than 5 microns in size) that may be suitable for initiating high-velocity eddy currents.

In some embodiments, the wall of the chamber around the radiation source may be reflective or may otherwise direct radiation emitted away from the internal volume 12 back toward the internal volume and the sample material located therein. Such a reflective structure may provide for further exposure of the sample material to the radiation.

Irradiation treatments may be focused or unfocused. In some embodiments, a lens is employed in cooperation with a radiation source so that emitted radiation may be focused in a suitable manner toward the internal volume of the processing chamber.

As discussed above, the sample treatment system 100 may include an acoustic energy source 2 spaced from the processing chamber 10. Acoustic energy emitted from the source 2 may be transmitted through a window 11 and converge at a focal zone 40, for focused acoustic treatment of material located within the internal volume 12.

Focused acoustic energy treatment, optionally provided in a continuous flow through system, may provide for highly efficient mixing and/or particularization (e.g., fragmenting) of the contents within the internal volume of the chamber. For example, such mixing and/or flow through may increase overall exposure of the sample material to radiation emitted from the source 70 in a continuous and uniform manner. When ultraviolet radiation is emitted from the source, focused acoustic treatment may provide for the sample material to be sterilized more efficiently than if no focused acoustic energy was provided to the material at all.

In some cases, subjecting the sample to focused acoustic energy and/or continuous flow through may enhance the effects of irradiation (e.g., sterilization, cleaning, etc.) on the sample. When used in combination with focused acoustics, high doses of ultraviolet radiation may be delivered evenly and uniformly throughout the sample material, efficiently, and without deleterious effects. As a result, the residence time(s) in the irradiation chamber may be shortened (due to the focused acoustic energy) and ultraviolet radiation treatment can be more accurately controlled.

The system may include a controller 20 coupled with the acoustic energy source 2 and/or the radiation source 70 for controlling the operation of the source(s). For example, depending on the desired level of focused acoustic energy treatment, which may be based on feedback information gathered from one or more sensors (not shown in this figure) regarding some aspect(s) of the sample material (e.g., whether the sample material has reached a desired degree of particularization transmittance, concentration, presence of a chemical/biological material, viscosity, temperature, density, mixing; how a reaction has proceeded, etc.), the controller may adjust one or more parameters of acoustic energy emission from the source 2 (e.g., intensity, cycles per burst, power output, etc.), as further described herein.

Similarly, depending on the desired level of ultraviolet radiation treatment, which may also be based on feedback information gathered from one or more sensors regarding the sample material (e.g., whether the sample has been sterilized, whether the sample has been damaged from radiation overexposure, etc.), the controller may adjust one or more parameters of ultraviolet irradiation from the source 70 (e.g., intensity, wavelength, frequency, power output, etc.), as also described herein.

It can be appreciated that any suitable sensor(s) may be used in embodiments of the present disclosure.

It can be appreciated that any suitable radiation source or combination of different sources may be used for emitting any suitable type of radiation, for example, ultraviolet radiation, infrared radiation, visible light, etc. In some embodiments, the radiation source is a low-pressure mercury lamp which generates ultraviolet radiation at a particular wavelength (e.g., 100-280 nm, 185-265 nm, ~254 nm).

FIGS. 4a-4e illustrate an embodiment of a sample treatment system 100 in operation where a sample material having a particle 60 is suitably sterilized, mixed and particularized.

Figure 4A:
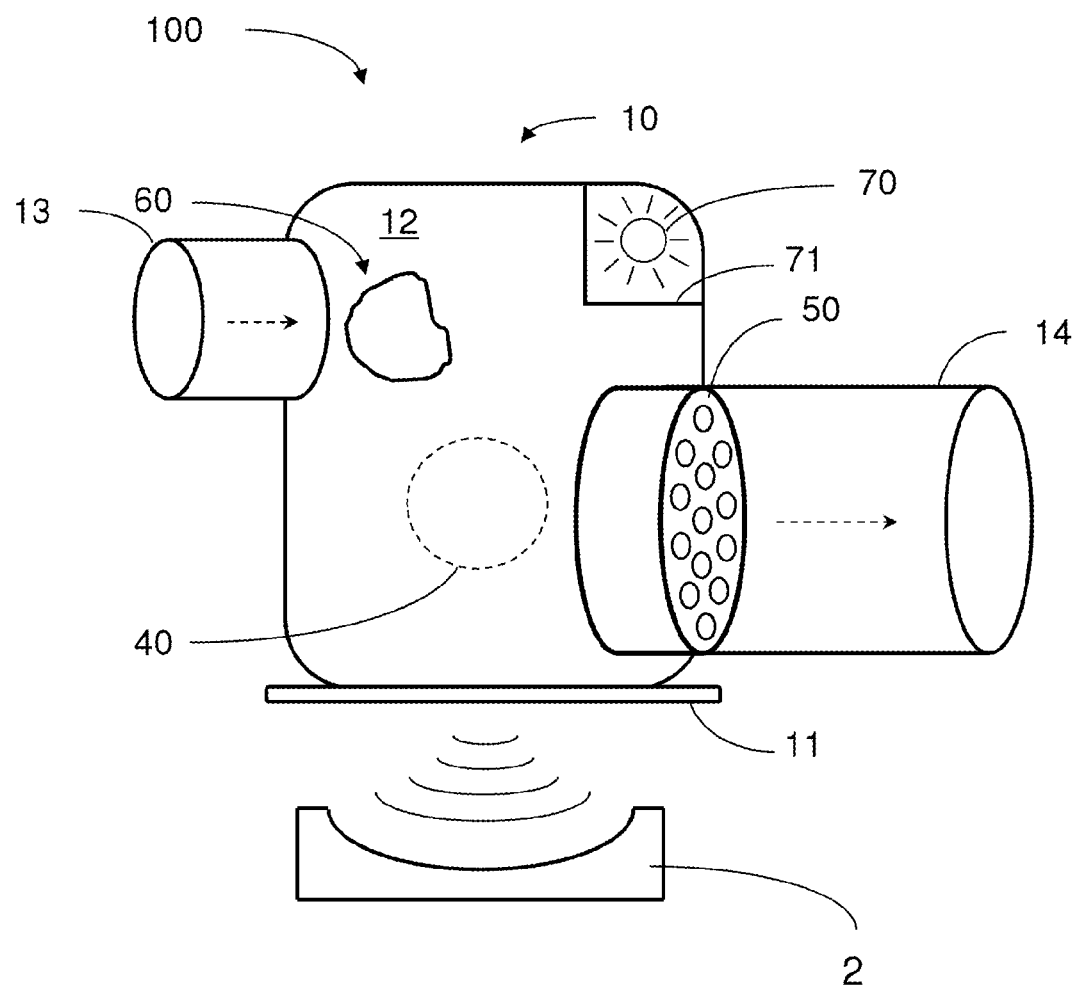
FIGS. 4a-4e illustrate schematic views of a sample treatment apparatus in operation in accordance with some embodiments.

In FIG. 4a, the sample material, including a particle 60 provided in a solution, enters through the inlet 13 into the internal volume 12 of the chamber 10. The particle 60 is subject to ultraviolet radiation emitted from the radiation source 70 and transmitted into the internal volume 12 through the window 71. The particle 60, initially, does not meet the threshold particle size that would allow the particle to exit the chamber 10 and proceed through the outlet 14.

Figure 4B:
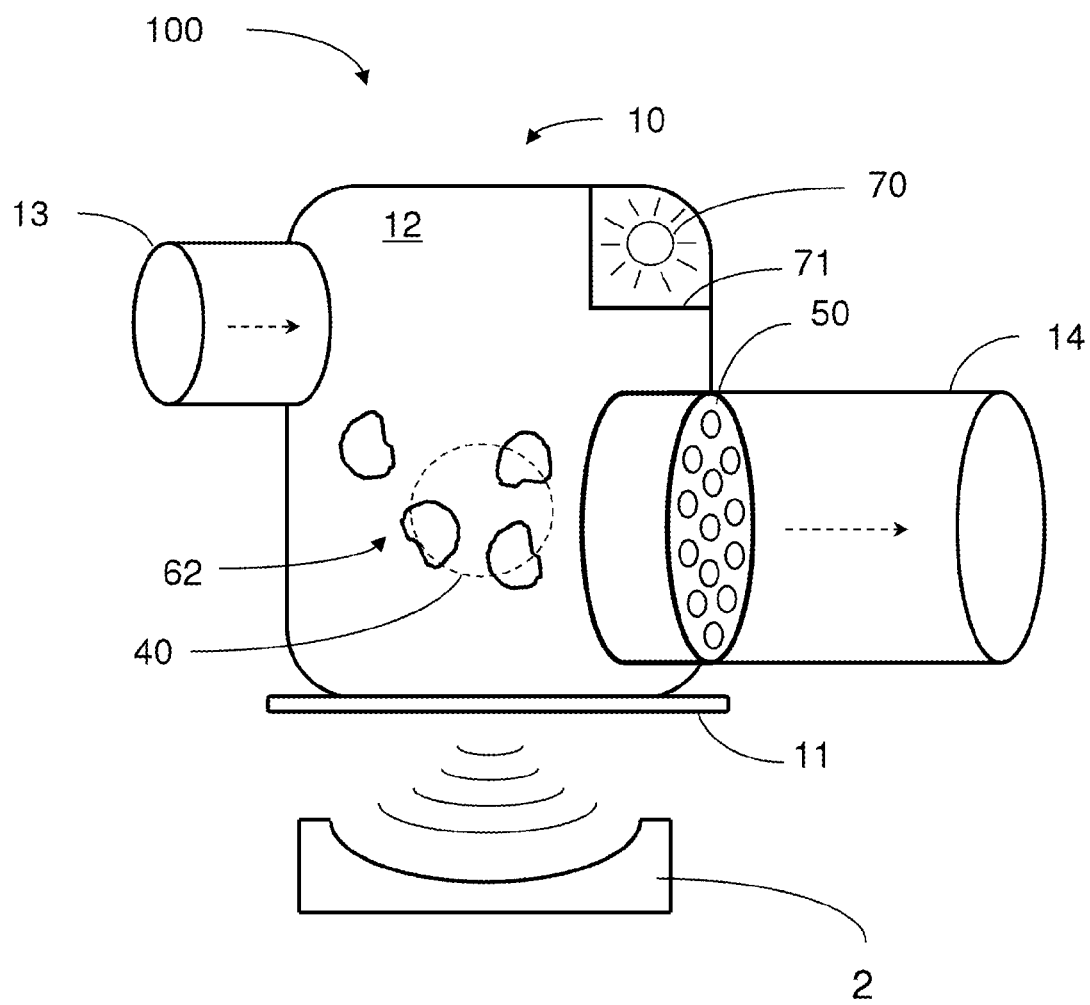
Figure 4C:
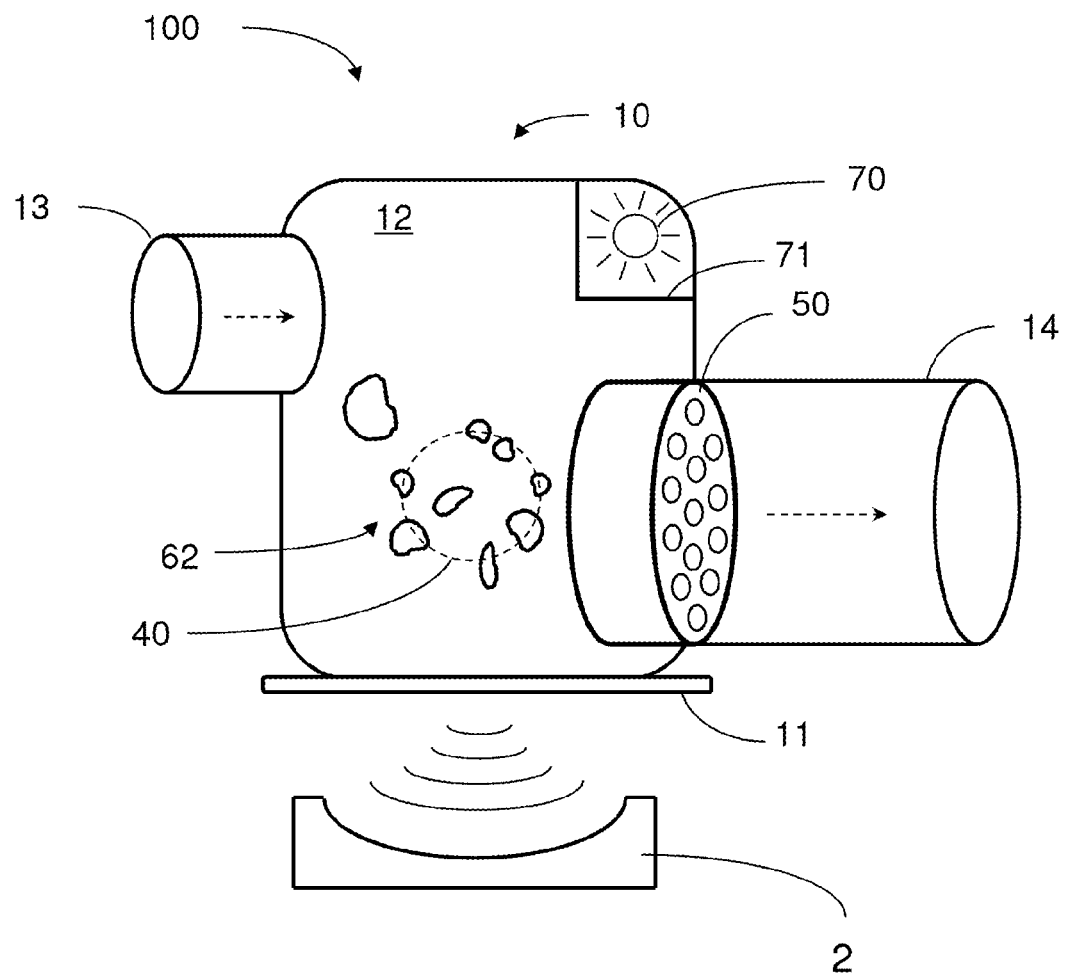

However, as shown in FIGS. 4b and 4c, the acoustic energy source 2 emits acoustic energy through the window 11 and into the internal volume 12 of the chamber 10. The acoustic energy converges at a focal zone 40 located within the internal volume. Upon exposure to the focused acoustic energy, the particle 60 is broken down into smaller particle fragments 62, reducing the overall size of the particle(s). The sample material is mixed within the internal volume 12 upon further exposure to the focused acoustic energy.

Accordingly, while the sample material is located within the internal volume 12 of the chamber, the sample material may be subject to an appropriate amount of focused acoustic treatment and radiation, simultaneously or in succession, depending on a desired treatment plan. That is, it should be appreciated that various methods of treatment described are optional in nature and not required for certain embodiments of the present disclosure. For example, the sample material may be subject to focused acoustic treatment independently from exposure to radiation; and vice versa, the sample material may be subject to radiation independently from exposure to focused acoustic treatment. Further, the sample material may be subject to a particular protocol of focused acoustic treatment and radiation treatment, whether in an alternating fashion or provided together at the same time.

Figure 4D:
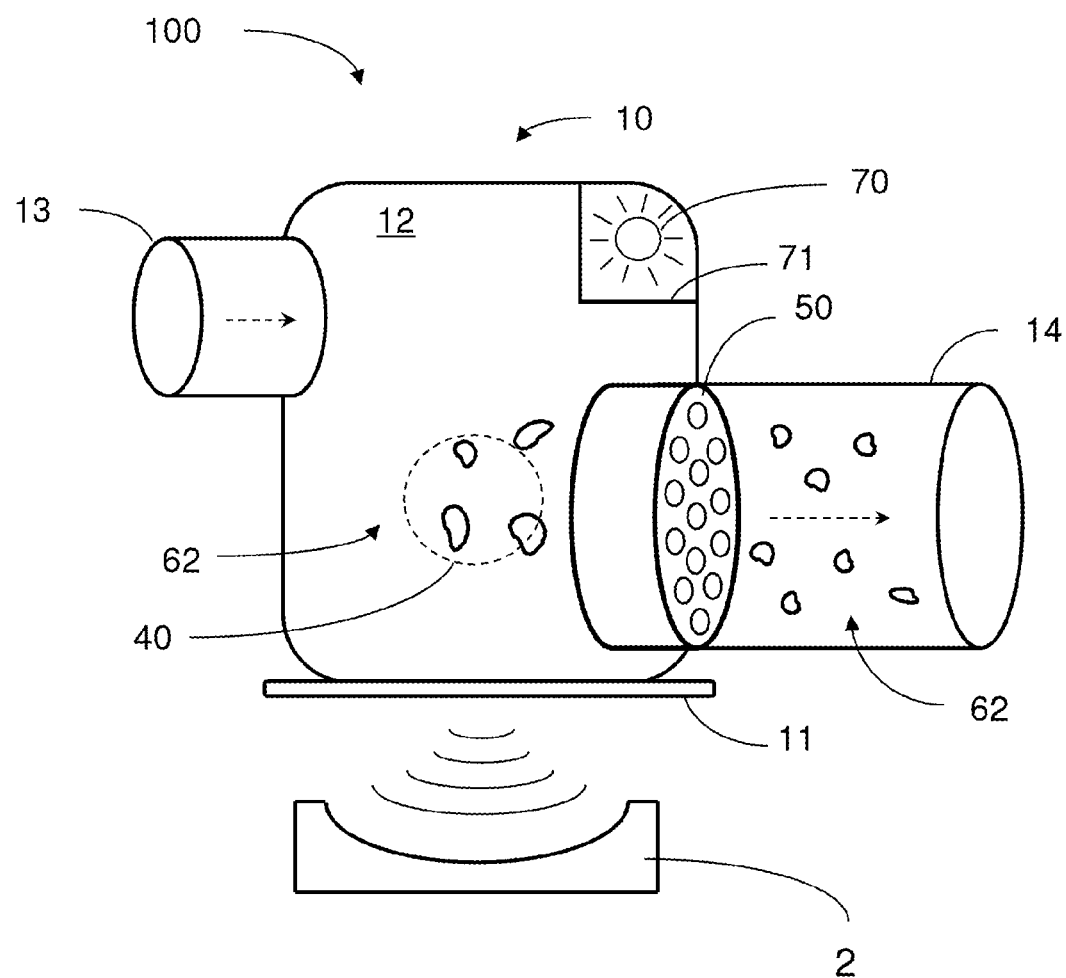
Figure 4E:
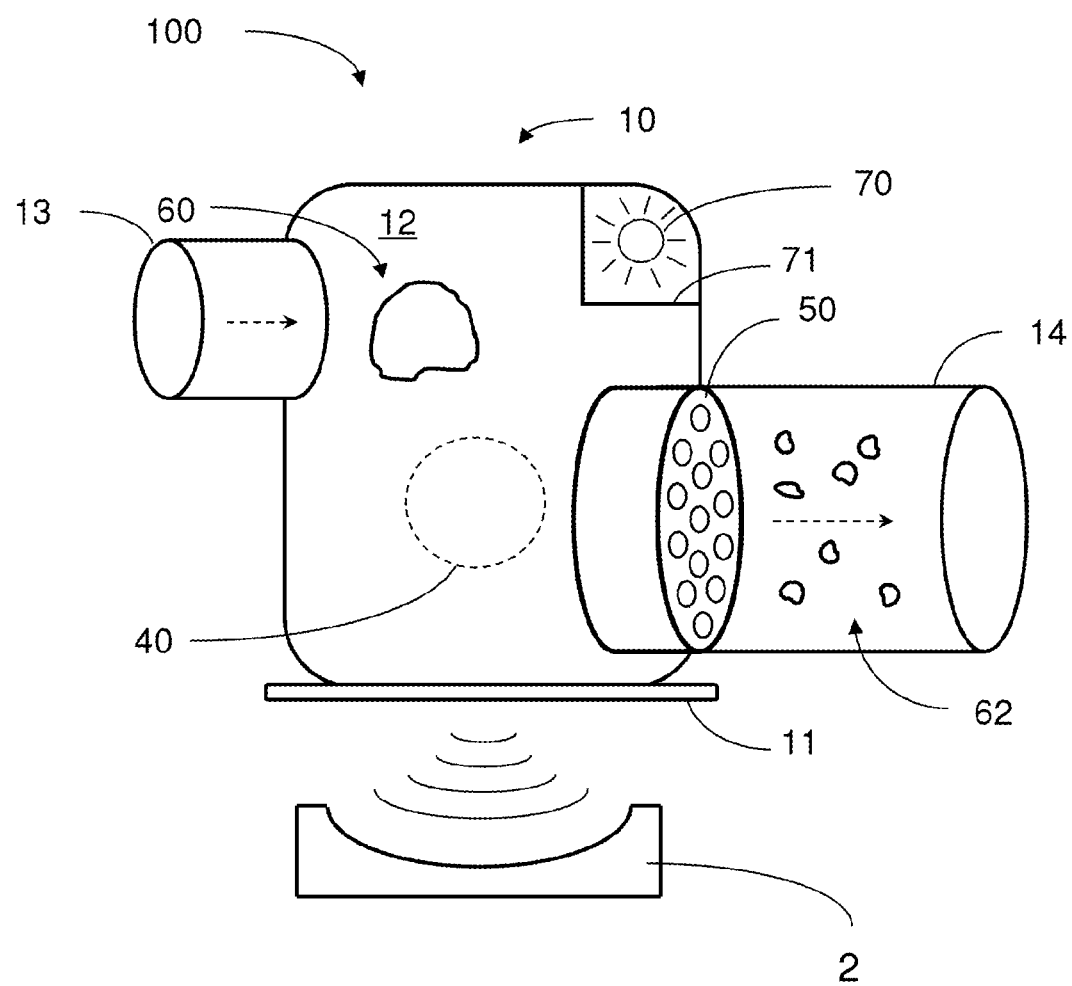

As particle fragments 62 are broken down further, the particle fragments may reach a size that is below the threshold particle size of the size exclusion filter 50, thus, permitting the particles to exit from the chamber 10 through the outlet 14, as depicted in FIG. 4*d*. Though, particle fragments 62 that do not reach a size that is below the threshold particle size of the filter are retained within the internal volume 12 of the chamber. That is, particle fragments that are not small enough are held within the internal volume, and thereby further exposed to focused acoustic energy and/or radiation. In this embodiment, particle fragments are permitted to exit from the internal volume of the chamber once they reach a size smaller than the threshold particle size provided by the filter 50. When appropriate, additional particle(s) 60 may be supplied through the inlet 13 and into the internal volume of the chamber, as depicted in FIG. 4*e*.

While not expressly shown in the figures, an appropriate retaining member may be positioned at the inlet of the chamber so as to filter entry of sample material into the processing volume.

Filters, valves, or other retaining members, in accordance with the present disclosure may be constructed or linked to one or more sensors according to any suitable desired criteria (e.g., physical, chemical, biological, etc.), such as a threshold particle size or chemical/biological composition. For example, the openings of the filter may be sized so as to approximate the threshold particle size, permitting particles with respective sizes less than the threshold particle size to pass through the filter, while obstructing particles having particle sizes greater than the threshold particle size from passing through the filter.

In some embodiments, the threshold particle size is between about 10 nm and about 10 microns, between about 100 nm and about 1 micron, between about 100 nm and about 500 nm (e.g., 150 nm, 200 nm, 220 nm, 250 nm, 300 nm, 350 nm, 400 nm, etc.). It can be appreciated that filters, or other retaining members, described herein may be constructed in accordance with any suitable threshold particle size. It can also be appreciated that a physical criterion for permitting passage through or past a retaining member may be that the material has a particle size that is larger, rather than smaller, than a threshold particle size.

Chemical or biological characteristics of the sample may be monitored through one or more sensors (e.g., microscopes, fluorescence markers, chemical/biological strips or detectors, etc.). Based on information provided by the sensor(s), the sample may then be permitted to enter and/or exit the internal volume of the processing chamber.

It can be appreciated that the criteria which is required for passage of sample material through one or more retaining members is not necessarily a "threshold" value where the particular criteria is met when a characteristic (e.g., physical, chemical, biological, etc.) is greater or less than the threshold value. For example, the criteria could be a range of values where sample material is not permitted to pass through the retaining member(s) unless the sample material has characteristics that fall within the range of desired criteria, such as a range of particle sizes, transmittance values, presence or absence of a (bio)chemical composition, degree of sterilization, or other suitable characteristics.

Figure 5A:
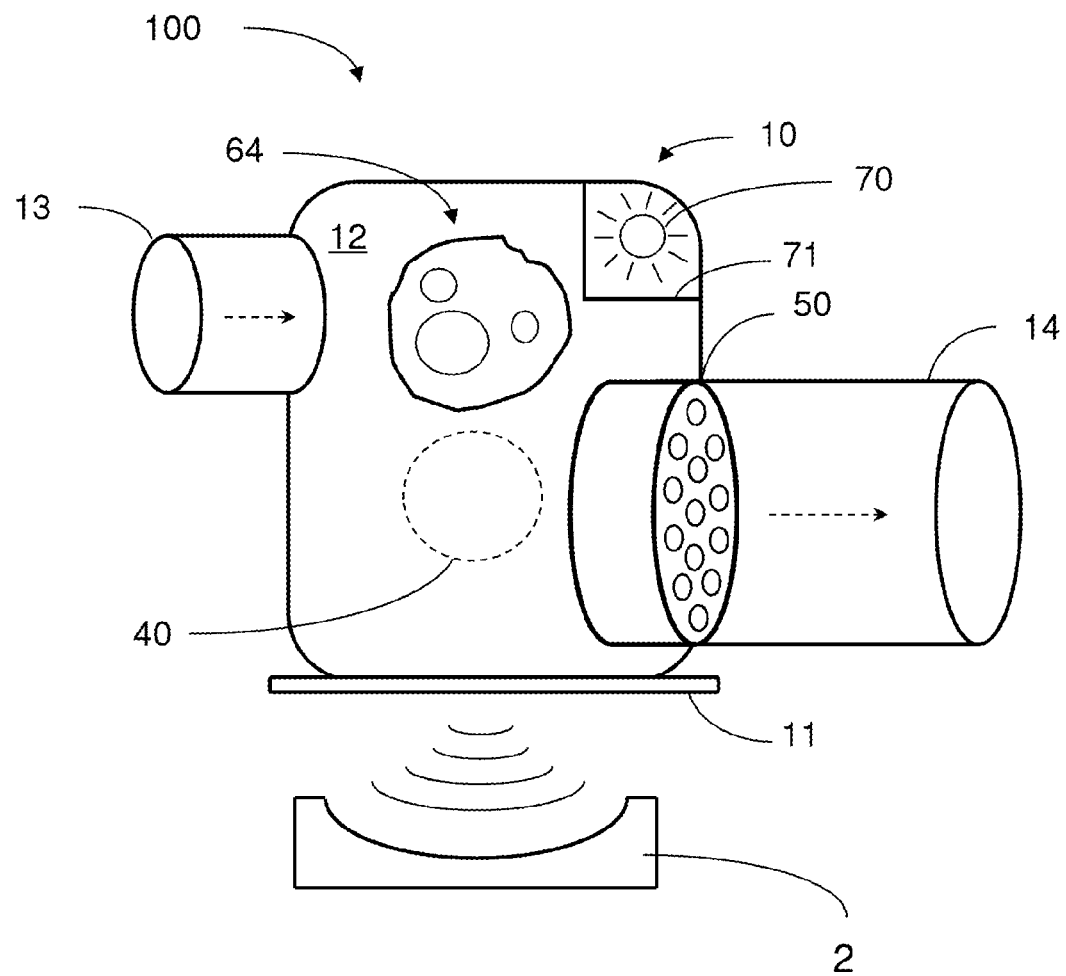
FIGS. 5a-5b depict schematic views of another sample treatment apparatus in operation in accordance with some embodiments.
Figure 5B:
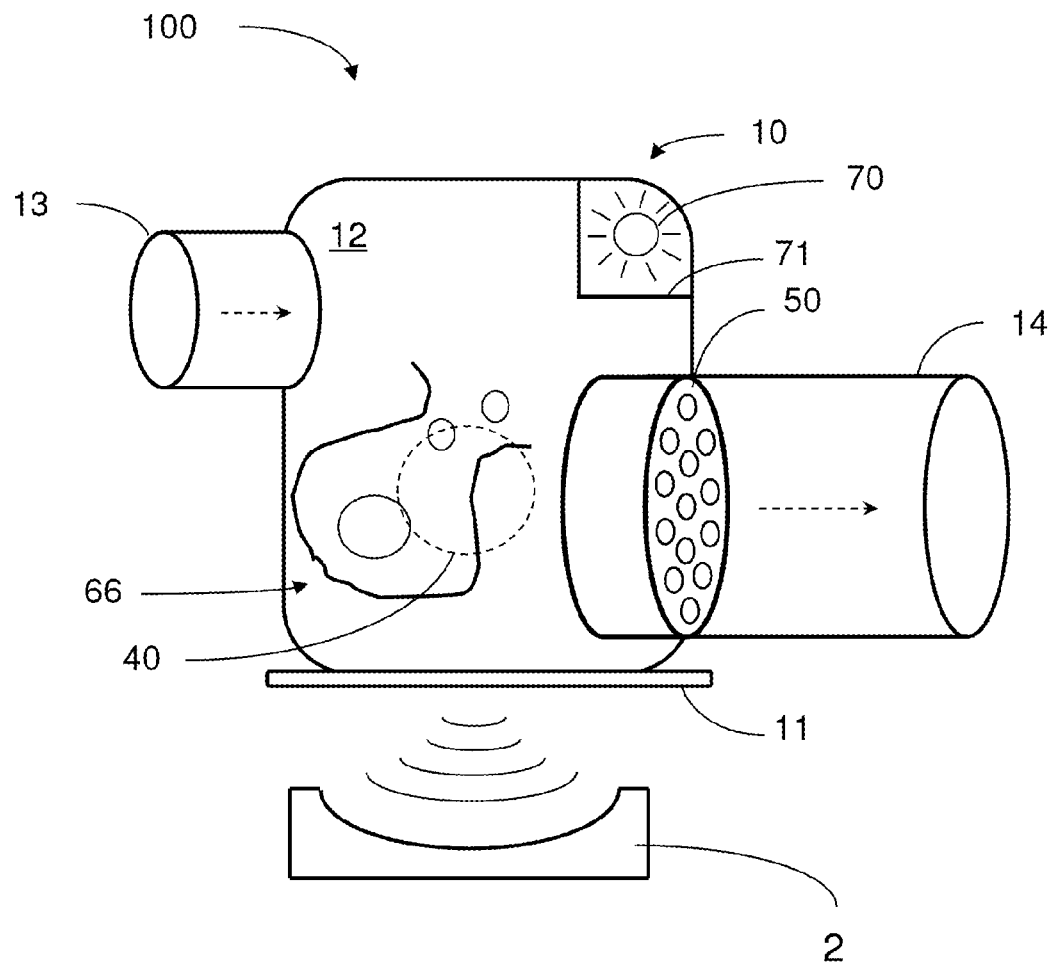

FIGS. 5*a*-5*b* illustrate an embodiment of a sample treatment system 100 in operation where a sample material having a cell 64 is processed using focused acoustic energy and/or ultraviolet radiation.

In FIG. 5*a*, the sample material, including the cell 64 provided in a solution, enters through the inlet 13 into the internal volume 12 of the chamber 10. The cell 64 is subject to ultraviolet radiation emitted from the radiation source 70 having entered the internal volume 12 through the window 71. At first, the cell 64 is too large to exit the chamber 10 through the outlet 14.

However, the cell is lysed upon exposure to the focused acoustic energy, as shown in FIG. 5*b*. Accordingly, parts of the lysed cell 66 are dispersed and mixed throughout the sample material, and subsequently filtered at the outlet 14.

In general, the respective energy of acoustic energy and radiation energy output may vary depending on the composition of the sample material and the intended application for which the sample is used. For example, if the sample material includes cells and/or proteins that may be sensitive to denaturation, the energy output of the acoustic energy source and/or the radiation source may be relatively low. However, if the sample material includes salt or carbon source compositions, the energy output of the acoustic energy source and/or the radiation source, along with overall flow rate, may be comparatively higher. It can be appreciated that cavitation caused by overall energy output of focused acoustic energy may be inhibited or enhanced based on the desired application(s).

Figure 6A:
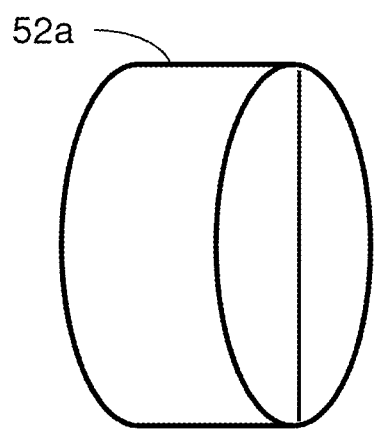
FIGS. 6a-6b illustrate perspective views of a retaining member in accordance with some embodiments.
Figure 6B:
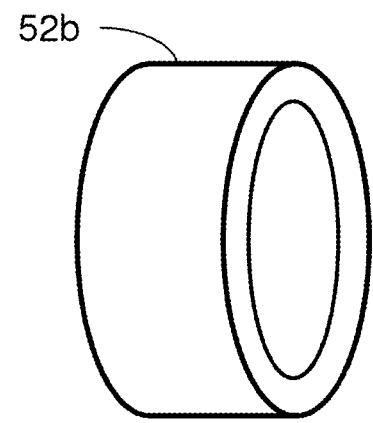

FIGS. 6*a*-6*b* depict an embodiment of another retaining member 52 that may be employed with sample treatment systems described herein. In some embodiments, and as shown, the retaining member 52 may be a valve, which may be actuated, by any suitable manner, to be in a closed position 52*a* and an open position 52*b*, as desired.

The valve may be positioned at the entrance to the outlet of the processing chamber (or at an inlet to the chamber) and controlled such that when the sample material within the processing chamber does not have characteristics that meet one or more criteria, as determined through feedback information gathered from a sensor, the valve is actuated or otherwise placed into a closed position. When the sample material within the processing chamber has characteristics that do meet the criteria (e.g., falls within a certain range of particle size, exhibits a particular level of transmittance, has a certain chemical/biological composition, is suitably sterilized, etc.), based on feedback information, the valve is placed in an open position.

When the valve is in the closed position, the sample material is obstructed from exiting from the internal volume of the chamber through the outlet. In contrast, when the valve is in the open position, the sample material is permitted to flow through the outlet away from the internal volume of the chamber.

As discussed above, in some embodiments, a criterion may be a characteristic other than particle size, such as the optical transmittance of the sample, presence/absence of a chemical/biological composition, or other characteristics. For instance, the system may be configured such that the material (e.g., solution) is prevented from flowing into the outlet and out from the internal volume of the processing chamber (e.g., valve is placed in a closed position) unless the sample material exhibits an optical transmittance that falls within a certain threshold transmittance range. Though, when the sample material does exhibit an optical transmittance that falls within the threshold transmittance range, the material is then allowed to flow into the outlet and out from the internal volume of the processing chamber (e.g., valve is placed in an open position). Accordingly, the system may be equipped with one or more sensors for sensing optical transmittance of the sample material, and a controller that receives the sensed information and, based on the sensed information, sends a signal to actuate the valve to be open or closed.

When the sample material includes a solution with particles of a certain size, the optical transmittance may vary. In some cases, solutions having particles of a generally small average size (e.g., less than 100 nm) may exhibit a greater optical transmittance as compared with solutions having particles that are comparatively larger in size (e.g., greater than 100 nm, between 400 nm and 700 nm). Though, it should be appreciated that there may be instances where solutions having particles of a larger average size may exhibit a greater optical transmittance than solutions having particles that are comparatively smaller in size.

Or, as the sample material is processed, the sample may or may not form a state of dispersion, such as an emulsion or a suspension, that exhibits a respective level of optical transmittance. For example, prior to focused acoustic processing of a sample solution, the solution may have a relatively high optical transmittance. Once subject to focused acoustic treatment, the solution may form an emulsion having multiple phases (e.g., forming liquid-liquid, liquid-air, liquid-solid interfaces) that interfere with light transmittance. That is, once the emulsion is formed, the optical transmittance of the sample may decrease substantially. Accordingly, depending on the desired threshold optical transmittance, the retaining member may or may not allow flow of the sample material out of the processing chamber.

Figure 7A:
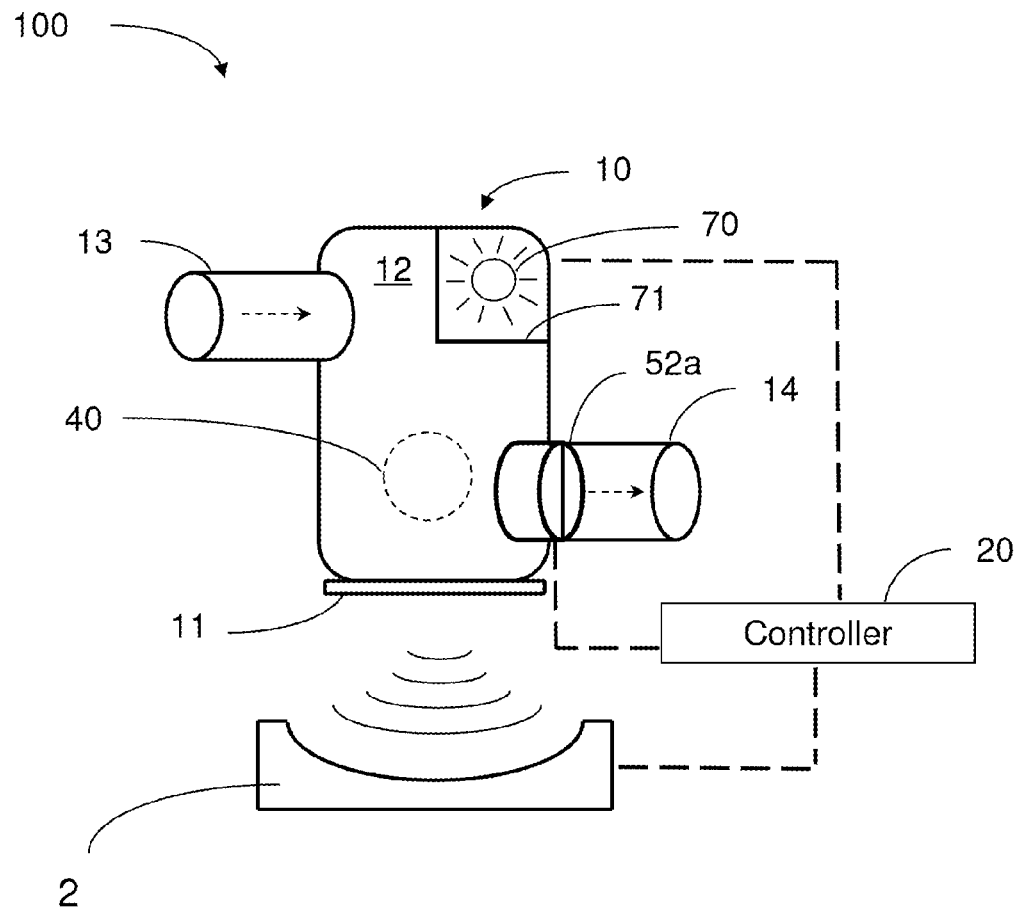
FIGS. 7a-7b depict a schematic view of a sample treatment apparatus in accordance with some embodiments.
Figure 7B:
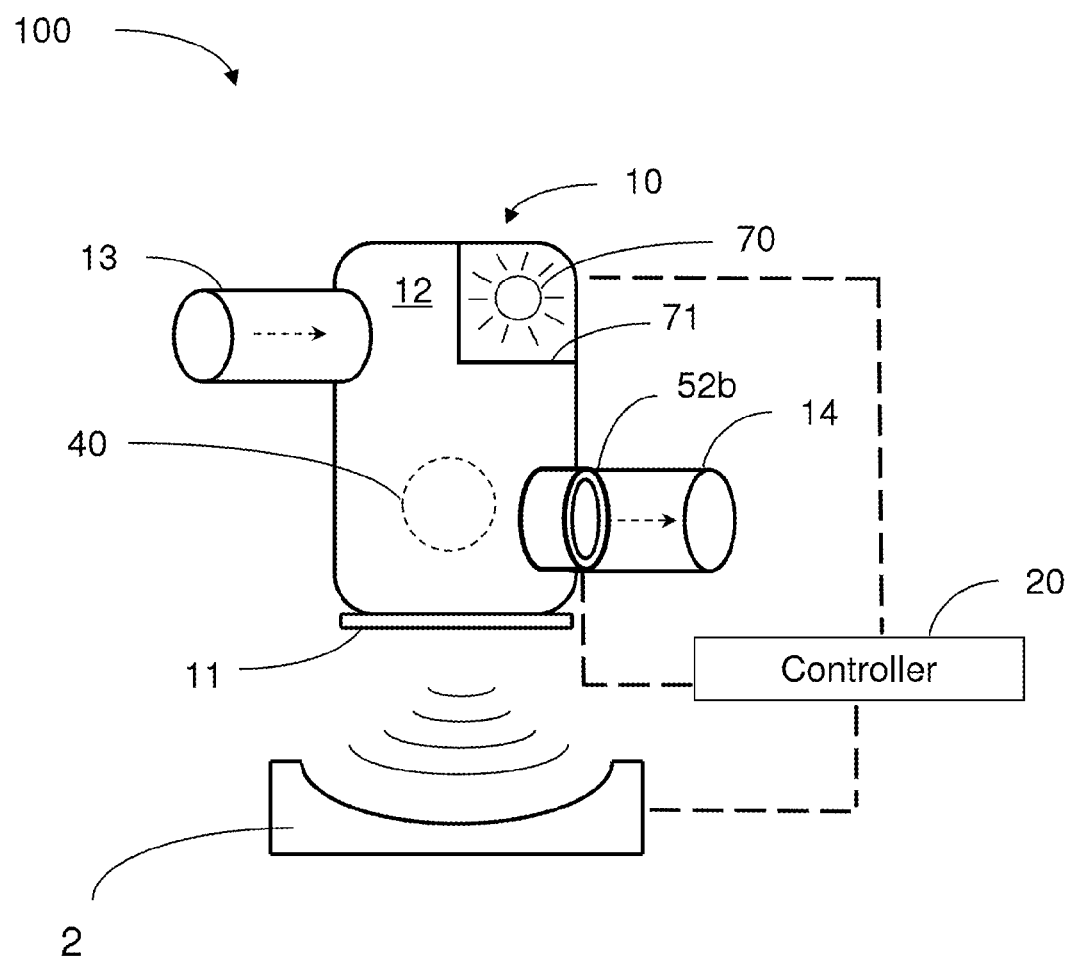

FIGS. 7a-7b shows an embodiment of a sample treatment system 100 that includes an inlet 13 for accommodating flow of sample material into a processing chamber 10 and an outlet 14 for accommodating flow of the sample material out of the processing chamber. A valve in a closed position 52a is positioned at the mouth of the outlet 14 to prevent material from exiting the internal volume of the processing chamber. While not shown, it can be appreciated that valves in accordance with the present disclosure may be positioned at other locations of the system, such as at an inlet of the chamber.

The system 100 also includes a radiation source 70 for emitting electromagnetic radiation (e.g., ultraviolet) into the internal volume of the processing chamber. As shown, the radiation source 70 is located behind a window 71, which may provide protection for the radiation source 70 so that the sample material, which may be biological, does not come into direct contact with or otherwise adhere to the radiation source. The window 71 may be transparent or translucent so as to transmit radiation emitted from the source 70 through the window and toward the internal volume 12 of the chamber. In some embodiments, the wall of the chamber around the radiation source may be reflective or may otherwise direct radiation emitted away from the internal volume 12 back toward the internal volume and the sample material located therein.

As discussed above, the sample treatment system 100 may include an acoustic energy source 2 spaced from the processing chamber 10. Acoustic energy emitted from the source 2 may be transmitted through a window 11 and converge at the focal zone 40, allowing for focused acoustic treatment of material located within the internal volume 12.

The system may include a controller 20 coupled with the acoustic energy source 2, the radiation source 70 and/or the valve 52, for controlling the operation of each component. As discussed above, the controller may employ an algorithm that processes feedback information gathered from one or more sensors (not shown in FIGS. 7a-7b) regarding the sample material, determine what level of focused acoustic energy and/or radiation treatment to which the sample material should be exposed to reach one or more preferred characteristics, and adjust one or more parameters of the appropriate source(s) 2, 70.

The controller may also process feedback information regarding the sample material and make a determination as to whether the sample material has characteristics that meet a particular criterion for flow of the sample material through or past the retaining member. If the characteristics of the material do not exhibit the one or more criteria, the controller 20 may transmit an appropriate signal to the valve that results in actuation of the valve to a closed position 52a. Once the material has characteristics that do meet the one or more criteria, the controller 20 may then transmit an appropriate signal to the valve that results in the valve being actuated to an open position 52b.

Figure 8:
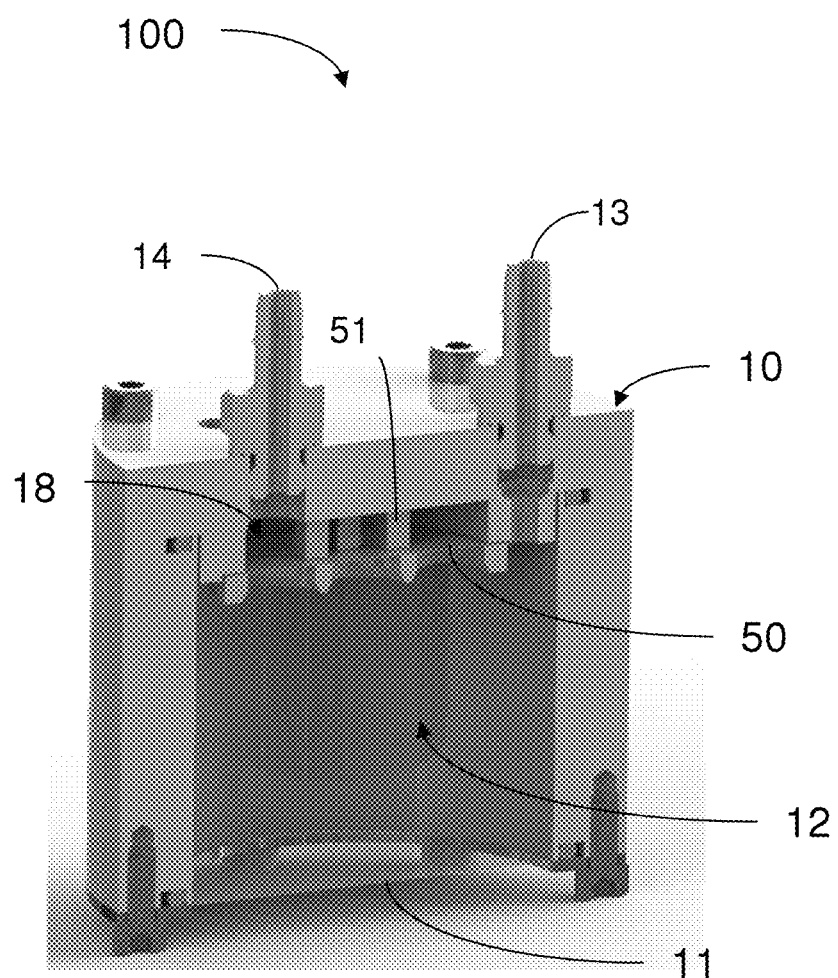
FIG. 8 shows a cross-sectional view of a sample treatment apparatus in accordance with some embodiments.

FIG. 8 depicts a cross-section of another embodiment of a portion of a sample treatment system 100 (acoustic energy source and radiation source are not expressly shown in FIG. 8). The system 100 includes an inlet 13 providing a conduit for entry of sample material into the internal volume 12 of the processing chamber 10, and an outlet 14 providing for exit of sample material from the internal volume via an outlet region 18. A filter 50, including a porous material with openings that are substantially uniform in size and shape is positioned between the internal volume and the outlet region 18. As shown, the filter 50 is held in place by support members 51 (e.g., columns, ribs, protrusions, etc.). Accordingly, any material that enters the internal volume 12 of the processing chamber through the inlet 13 passes through the filter 50 before exiting through the outlet 14 via the outlet region 18.

Figure 9A:
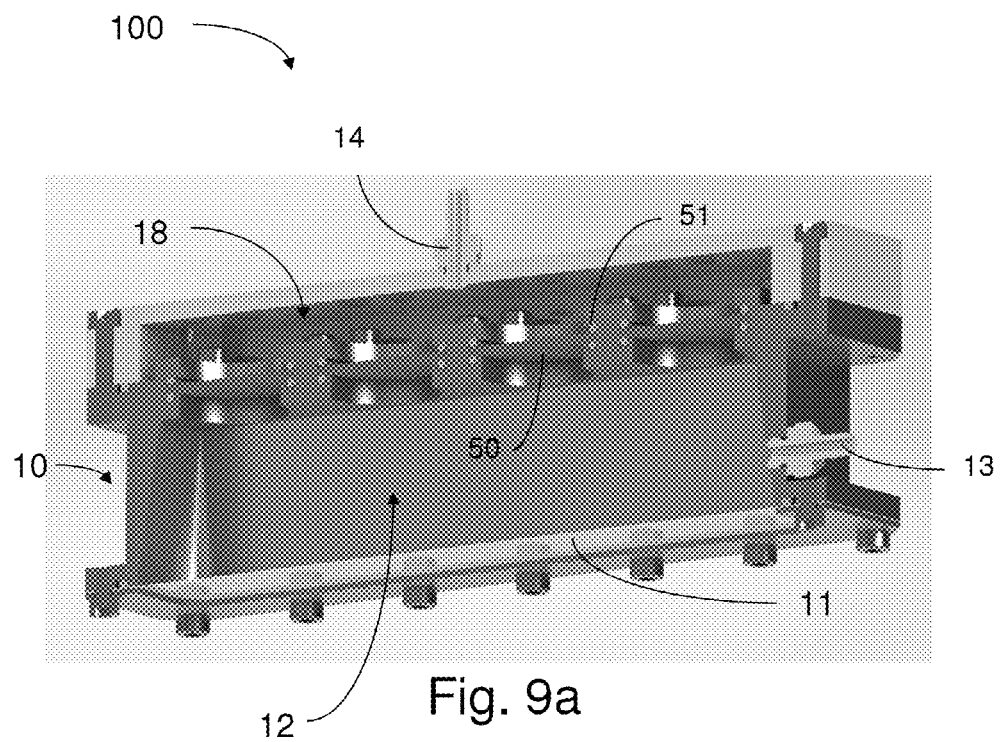
FIG. 9a depicts a cross-sectional view of a sample treatment apparatus in accordance with some embodiments.
Figure 9B:
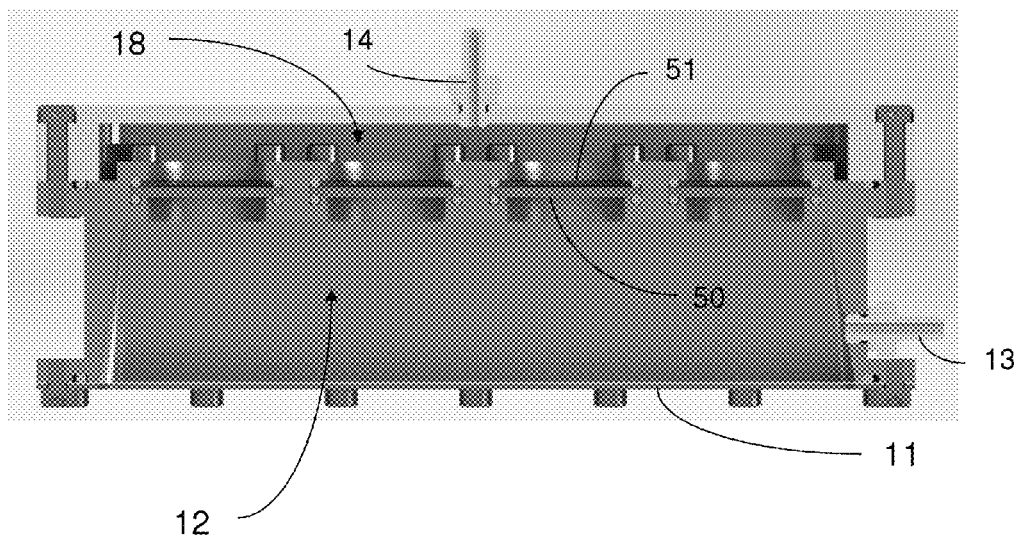

FIGS. 9a-9b illustrate a cross-sectional view of another embodiment of a sample treatment system 100, including multiple filters 50. The chamber 10 of the system 100 has a length that allows for a plurality of filters to be incorporated therein. In some embodiments, inclusion of multiple filters may provide for increased flow rates (e.g., multiple paths for fluid flow) between the inlet 13 and outlet 14 than would be the case for a system that includes fewer filters, or a single filter. As shown, support members 51, provided as o-rings, may be positioned on either side of each filter 50 so as to hold the filter in place while providing for a seal between the filter and the chamber wall.

As discussed above, any suitable filter may be used in sample treatment systems according to the present disclosure. For example, the filter may be composed of an appropriate material (e.g., polyethersulfone). The filter may also have suitable dimensions (e.g., 0.2-3 micron pore size; 20-30 mm diameter, etc.). Further, the filter may be suitably supported, such as by a porous disc (e.g., pores approximately 30-50 microns in size).

Figure 10A:
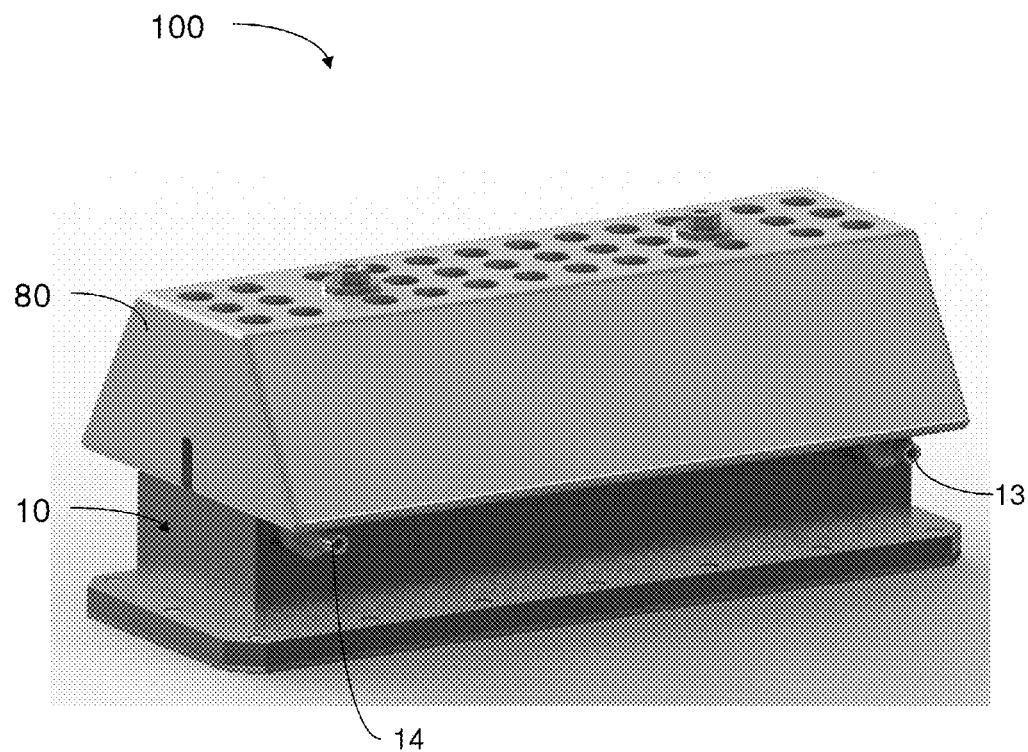
FIG. 10a depicts a perspective view of a sample treatment apparatus having a shroud in accordance with some embodiments.

FIGS. 10a-10d show another embodiment of various portions of a sample treatment system 100. Here, the system 100 includes a processing chamber 10 having a housing with an inlet 13 and an outlet 14 attached or otherwise coupled thereto. Located over the processing chamber 10 is a cover 80 shielding the internal volume of the processing chamber from external light. The cover 80 may also prevent radiation generated from underneath the cover from escaping. As shown in FIG. 10a, the cover 80 has a number of holes through which an operator may inspect to see if the system is operating properly.

Figure 10B:
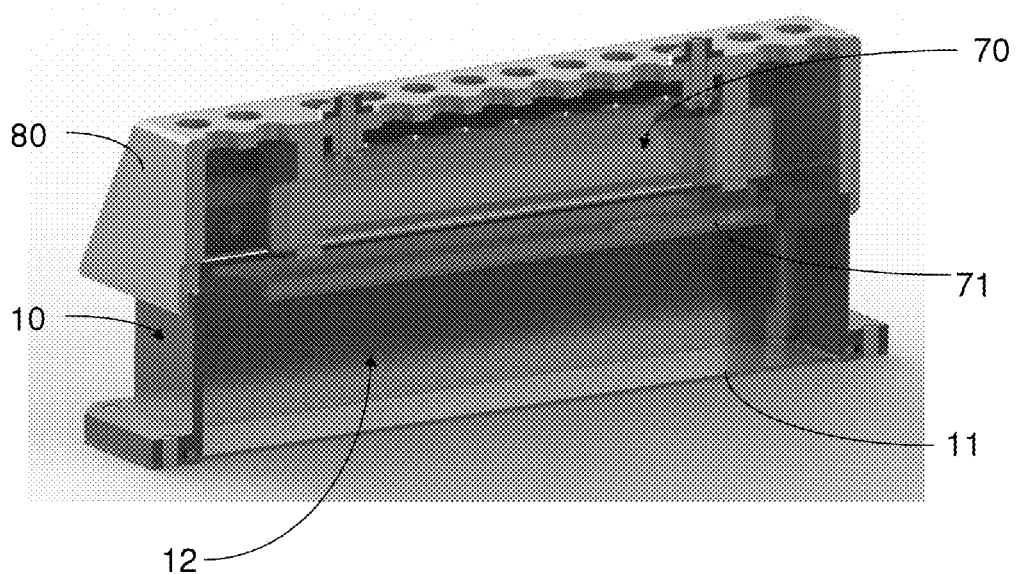

FIG. 10b shows a cross-section of this embodiment where the radiation source 70 is provided as a rod-shaped ultraviolet source, optionally fixed to housing of the system. As shown in this embodiment, the radiation source 70 is positioned behind a window 71, which provides protection for the radiation source 70 while transmitting radiation emitted from the source therethrough toward the internal volume 12 where sample material is subject to focused acoustic energy.

Figure 10C:
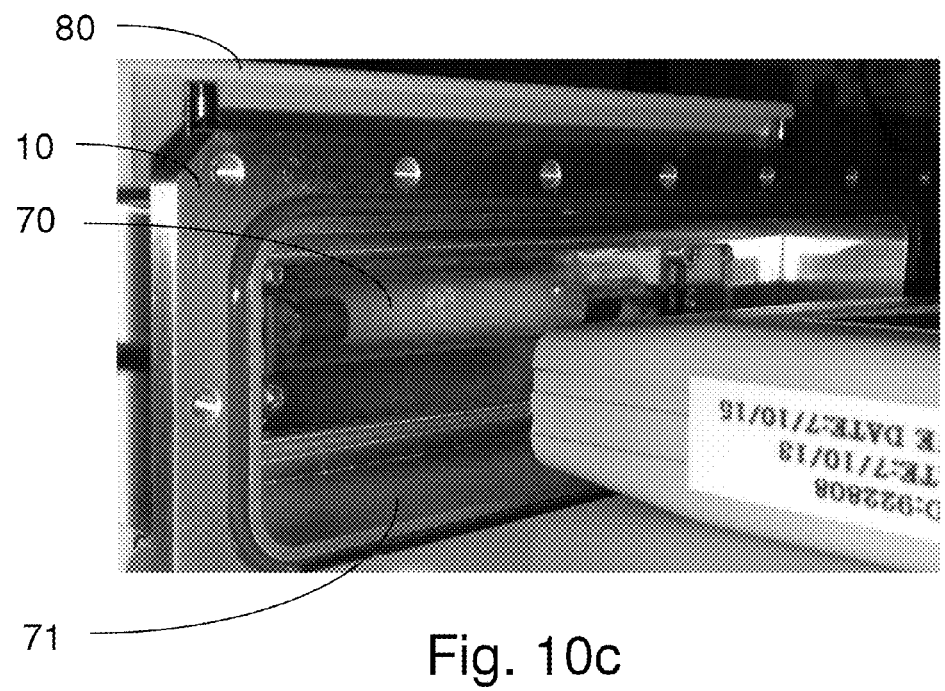

FIG. 10c shows a view of the underside of the apparatus with the processing volume of the chamber removed. As shown, the window 71 may be transparent or translucent and may transmit radiation emitted from the source 70 through the window and toward the internal volume 12 of the chamber. As discussed above, the wall of the chamber around the radiation source may optionally direct radiation emitted thereon toward the internal volume of the processing chamber. The cover 80 may be further shaped (e.g., tapered, curved, etc.) so as to reflect or otherwise direct radiation toward the internal volume of the processing chamber, resulting in increased or enhanced exposure of the sample material to the radiation treatment. Accordingly, the cover 80 may serve as a shroud that substantially retains light emitted from the radiation source and blocks external light from entering into the internal volume of the processing chamber.

Figure 10D:
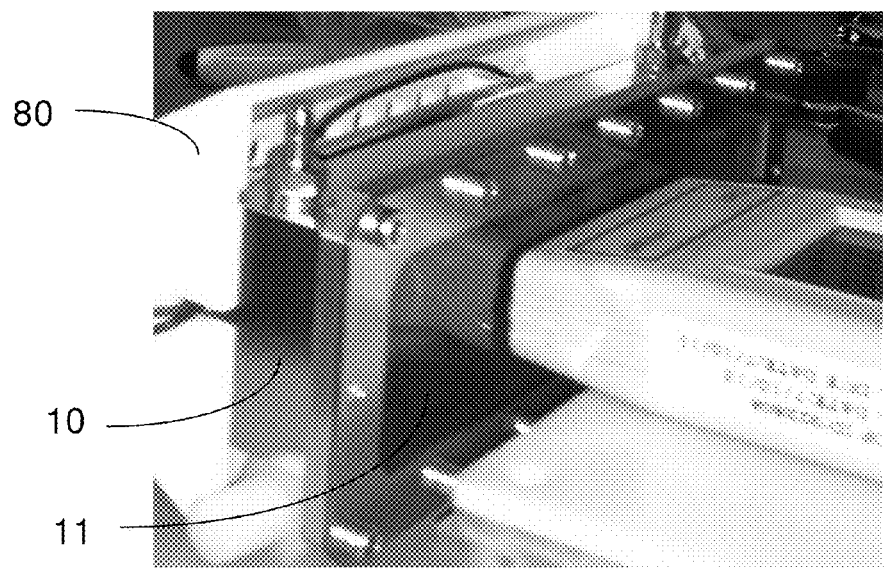

FIG. 10d shows another view of the underside of the apparatus with the processing volume of the chamber included. The window 11 is provided at the bottom of the chamber and transmits acoustic energy emitted from an acoustic energy source toward the internal volume of the chamber. In this embodiment, the acoustic energy source (not shown in this figure) is located external to the processing chamber on a side of the internal volume opposite the radiation source. In some embodiments, the window 11 may be composed of a material (e.g., Kapton®) that substantially prevents radiation (e.g., ultraviolet) from being transmitted therethrough. That is, the window 11 may allow for acoustic energy transmission, yet "traps" ultraviolet radiation within the internal volume of the chamber. Accordingly, a system that effectively retains radiation within the internal volume of the chamber may exhibit an increased efficiency in radiation treatment (e.g., sterilization using UVC radiation), without substantial loss of energy, as compared to systems that do not retain radiation within the processing volume (e.g., by incorporating windows that allow for radiation transmission).

Figure 10E:
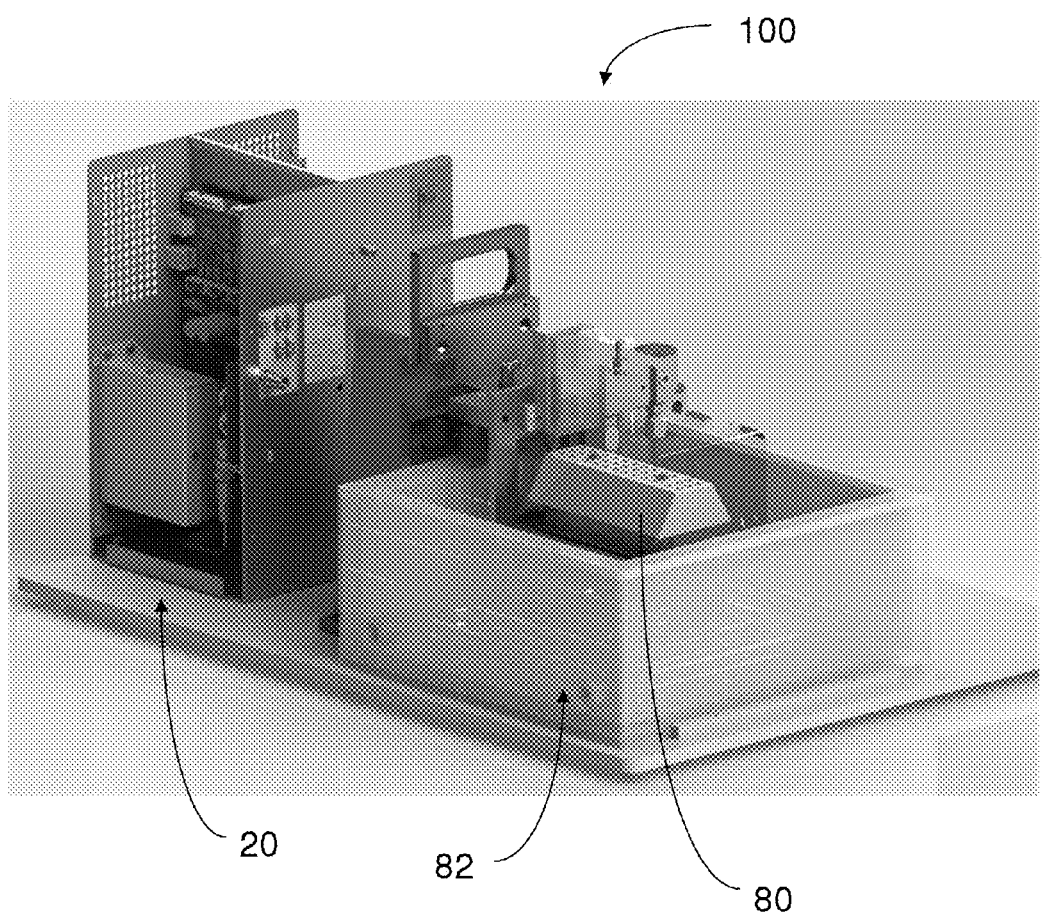
FIG. 10e shows a perspective view of a sample treatment apparatus in accordance with some embodiments.

FIG. 10e shows the sample treatment system 100 including the processing chamber having a cover 80, a temperature control system 82 and a controller 20. The temperature control system 82 includes a container for holding a water bath and conduits for flow and replenishment of coolant around the processing chamber. As described herein, a temperature control system may be useful for maintaining the temperature of the sample material within a desired range. The controller 20 is in electrical communication with each of the components of the system (e.g., acoustic energy source, radiation source, temperature control system, mechanical actuators, retaining member, sensors, etc.) and may provide for automated acoustic and/or radiation processing of the sample material within a flow through arrangement.

As discussed above, treatment systems described herein may provide for irradiation of sample materials without substantial loss of energy. By way of example, in accordance with the embodiment of FIGS. 10a-10e, a rod-shaped tube in free air was measured to exhibit a radiation power density of 382 $\mu W/cm^2$. With the cover 80 and window 11 (which resists radiation transmission therethrough) in place, shown in FIG. 10d, there was no detected radiation power output leaked from the chamber. That is, substantially all of the radiation emitted from the source was retained within the internal volume of the processing chamber.

However, upon removal of the window 11 (not shown in the figures), a radiation power density of 252 $\mu W/cm^2$ was detected at a location approximate to where sample material would be during processing. This measurement shows that the system has experienced a radiation power loss of approximately 130 $\mu W/cm^2$, from 382 $\mu W/cm^2$. Upon removal of both the window 11 and the chamber housing (with the cover 80 remaining), such as that shown in FIG. 10c, a radiation power density of 296 $\mu W/cm^2$ was detected at a location approximate to where the sample material would be during processing. Accordingly, based on the above observations, the radiation power loss from the radiation source when utilized by the system is less than 35%, and may be less than 30%, less than 25%, less than 20%, less than 15% or less than 10%.

Figure 11A:
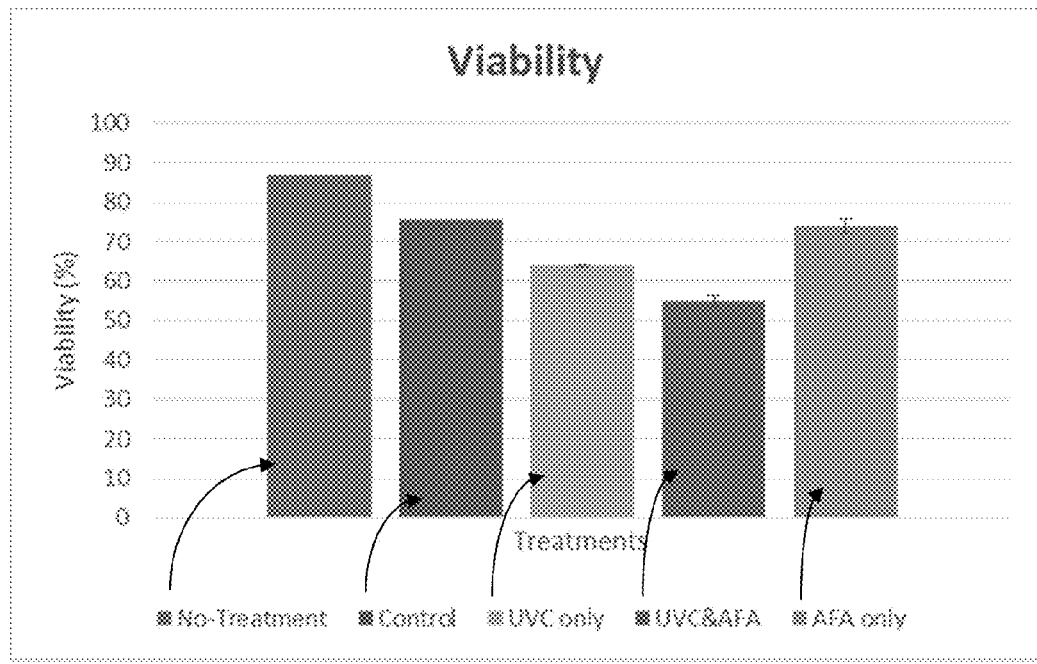
FIGS. 11a-11b illustrate graphs showing results of samples treated under various conditions.
Figure 11B:
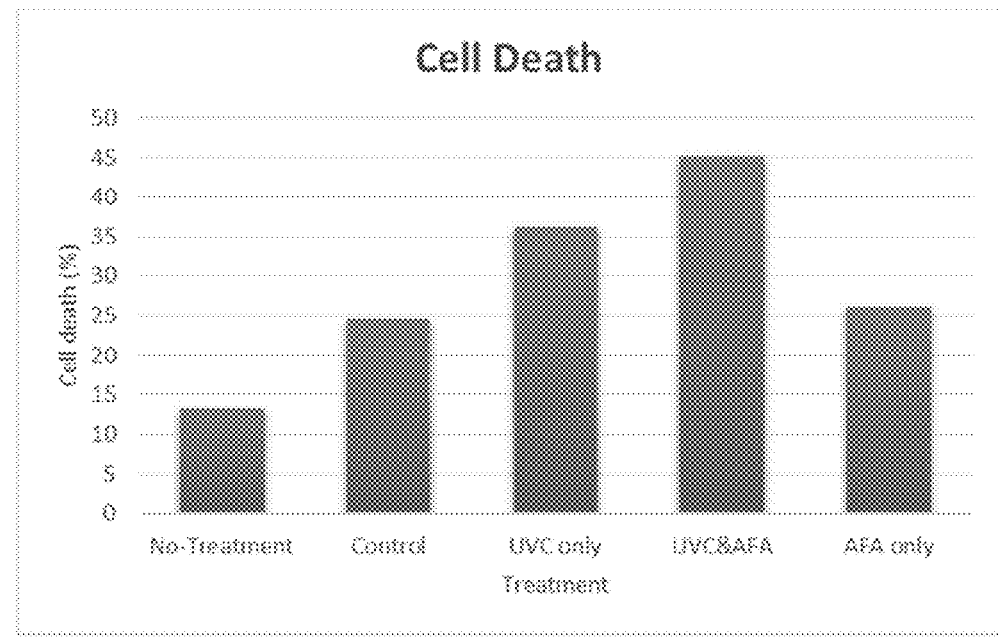

Further, focused acoustic energy used in conjunction with radiation treatment may enhance the effects of the radiation. For instance, focused acoustics may enhance the sterilization effects of UVC radiation on a sample. In an example, the effects of UVC radiation on a sample, employed with and without focused acoustics in a continuous flow through system, were observed. FIGS. 11a-11b show graphs that include experimental data of Cell Viability and Cell Death (Cell Viability %+Cell Death %=100%) under various processing conditions. In this example, the greater the Cell Death (lower the Cell Viability), the more effective the sterilization protocol. Experiments corresponding to these graphs were run on samples of yeast having a volume of approximately 110 mL. Focused acoustic energy was provided by a line shaped transducer having an average acoustic power output of approximately 100 W where no significant cell lysis was observed. The results of each of the processing protocols will now be discussed.

For the "No-Treatment" experiment, the yeast sample was not subject to recirculation, focused acoustic treatment or UVC radiation. In accordance with FIGS. 11a-11b, the Cell Viability % and Cell Death % were observed to be approximately 87% and 13%, respectively.

For the "Control" experiment in the example of FIGS. 11a-11b, the yeast sample was recirculated through a continuous flow through system, via peristaltic pumping, without exposure to focused acoustic energy or UVC radiation. The Cell Viability % and Cell Death % were observed to be approximately 75% and 25%, respectively.

For the "AFA only" experiment, the yeast sample was recirculated through a continuous flow through system. During circulation, while not exposed to UVC radiation, the sample was concurrently exposed to focused acoustic energy having a power of 100 W, 50% duty cycle and 1000 cycles per burst for 10 minutes. The Cell Viability % and Cell Death % were observed to be approximately 74% and 26%, respectively. It can be appreciated that any suitable focused acoustic energy parameters may be used.

For the "UVC only" experiment, the yeast sample was recirculated through the continuous flow through system and, while any suitable radiation parameters may be used, the sample was exposed to a UVC radiation power density through a quartz window of 250 mW/cm$^2$ for 10 minutes, without exposure to focused acoustic energy. The Cell Viability % and Cell Death % were observed to be approximately 63% and 37%, respectively.

For the "UVC&AFA" experiment, the yeast sample was recirculated through the continuous flow through system. The sample was also exposed to focused acoustic energy and UVC radiation, each having the above described parameters. The Cell Viability % and Cell Death % were observed to be approximately 55% and 45%, respectively. Accordingly, in this example, it was observed that exposure to the focused acoustic energy in conjunction with UVC radiation resulted in an enhanced sterilization treatment, where Cell Death was shown to increase from approximately 37% to 45%; and the Cell Viability was observed to decrease from approximately 74% to 63%. It is thought that the turbulence generated in the sample material by the focused acoustic energy may contribute to improving the overall effects of the UVC radiation. For example, focused acoustic energy may be run at a power setting that is sufficient to give rise to agitation/turbulence within the sample, resulting in greater overall exposure of the sample to the radiation.

As discussed above, overexposure and/or non-uniform delivery of ultraviolet radiation, or other types of radiation, may result in tissue and/or protein damage. As described herein, the sterilizing effects of the irradiation may be enhanced by the focused acoustic energy and, thus, irradiation treatment of samples may be comparatively more efficient when coupled with focused acoustics, than without. Accordingly, the risk of overexposure of tissue/cellular samples to irradiation may be effectively reduced when irradiation is employed in the presence of focused acoustic energy.

In further embodiments of the present disclosure, focused acoustic energy generated from sample treatment systems described herein may be used to move material located on retaining members. That is, when debris and/or residual sample material collects on or adjacent to a retaining member (e.g., filter), the focused acoustic energy may be directed at the retaining member itself, rather than a simple space within the internal volume of the processing chamber, for acoustically treating the retaining member. For example, the focal zone of the acoustic energy may converge directly on a surface of the retaining member. In this respect, the retaining member may be agitated in a manner that dislodges residual material from the surface of the retaining member. The focal zone may be moved relative to the retaining member so as to suitably "sweep" various regions of the retaining member. In some embodiments, the focal zone may move relative to the retaining member in a direction that runs counter to the direction of flow of the sample through the retaining member.

Figure 12A:
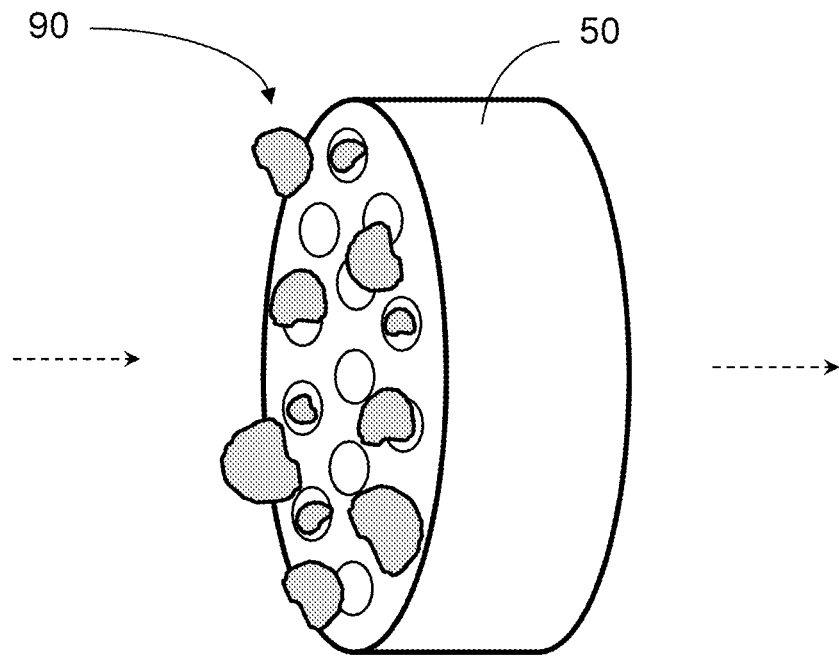
FIG. 12a depicts a side perspective view of a retaining member and various particles in accordance with some embodiments.

FIG. 12a shows an illustrative embodiment of a porous filter 50 having a number of openings that would normally allow particles having a size less than a threshold particle size through the filter. However, particulate debris 90 has collected on the surface of the filter 50 (e.g., via cohesion, adhesion to the surface), blocking entrance of particles that would otherwise be permitted to flow through the openings of the filter. That is, flow through the filter 50 in the direction indicated by the dashed arrows is substantially impeded.

Figure 12B:
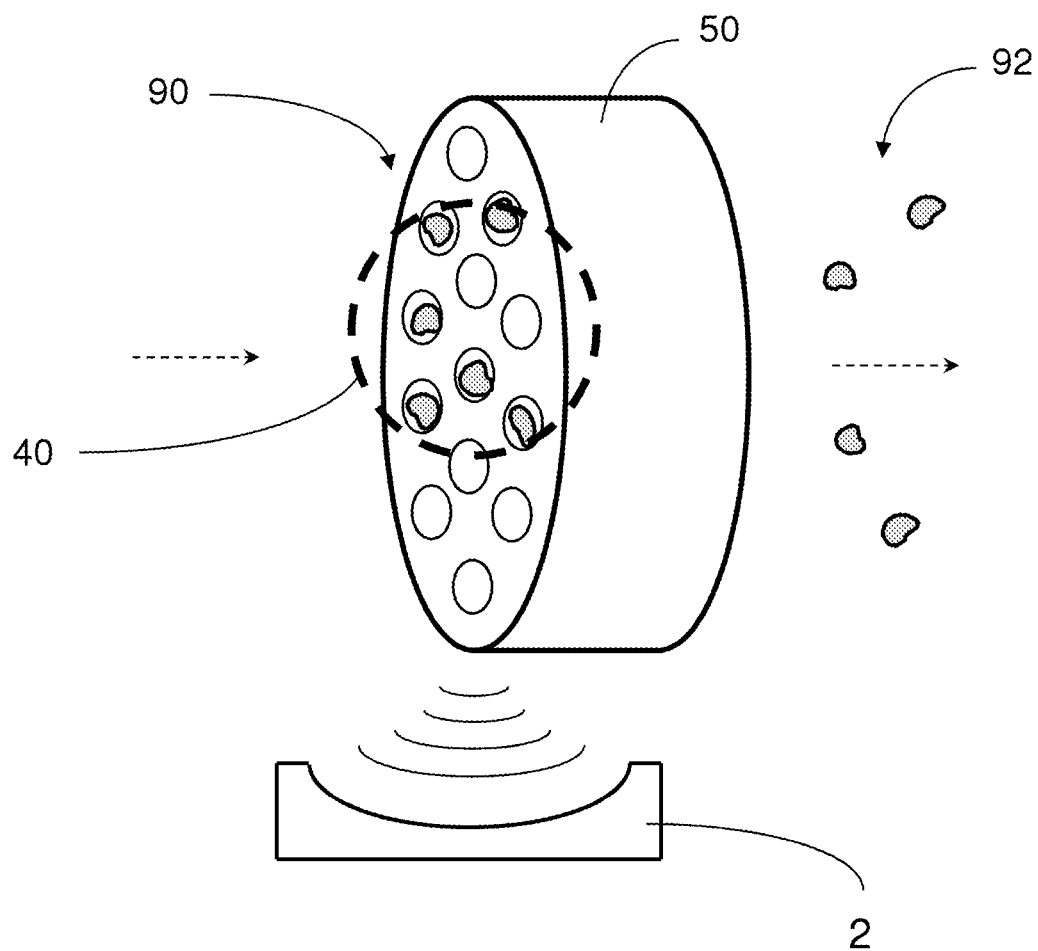
FIG. 12b shows a side perspective view of the retaining member of FIG. 12a treated with focused acoustic energy in accordance with some embodiments.

In FIG. 12b, an acoustic energy source 2 is oriented so as to direct focused acoustic energy toward the filter 50, forming a focal zone 40 at the surface of the filter. Once in contact with, or otherwise affected by, the focused acoustic energy, the particulate debris 90 is broken down into smaller fragments 92. These smaller fragments 92 are now of a particle size that is smaller than the size of the openings of the porous filter. Accordingly, the small fragments fall within the threshold particle size range that results in flow of the fragments through the filter. In addition, the focused acoustic energy may cause constant agitation of the particulate debris and the filter itself so that the surface of the filter remains substantially clean.

Figure 13A:
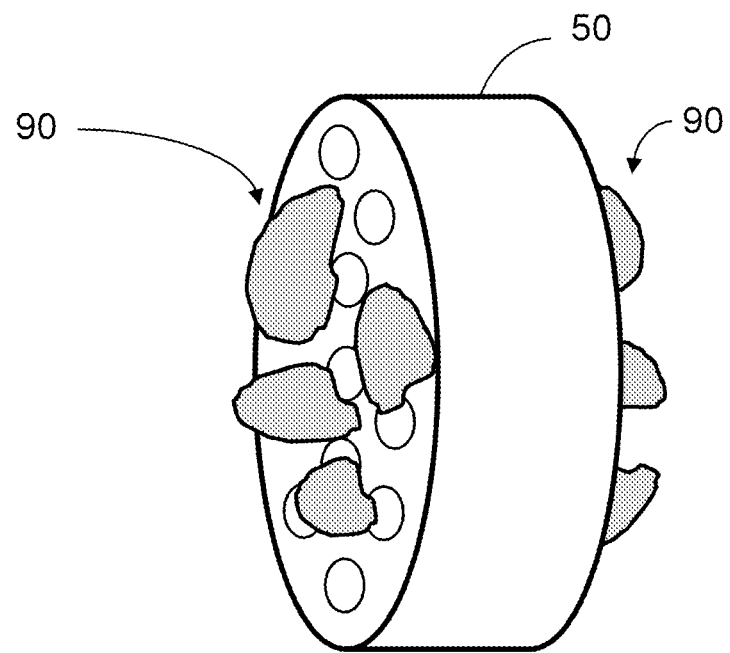
FIG. 13a illustrates a side perspective view of a retaining member and various particles in accordance with some embodiments.

FIG. 13a shows another illustrative embodiment of a porous filter 50 similar to that shown in FIG. 12a. Particulate debris 90 has collected on the surface of both sides of the filter 50, obstructing flow of particles that would otherwise be able to flow through the filter.

Figure 13B:
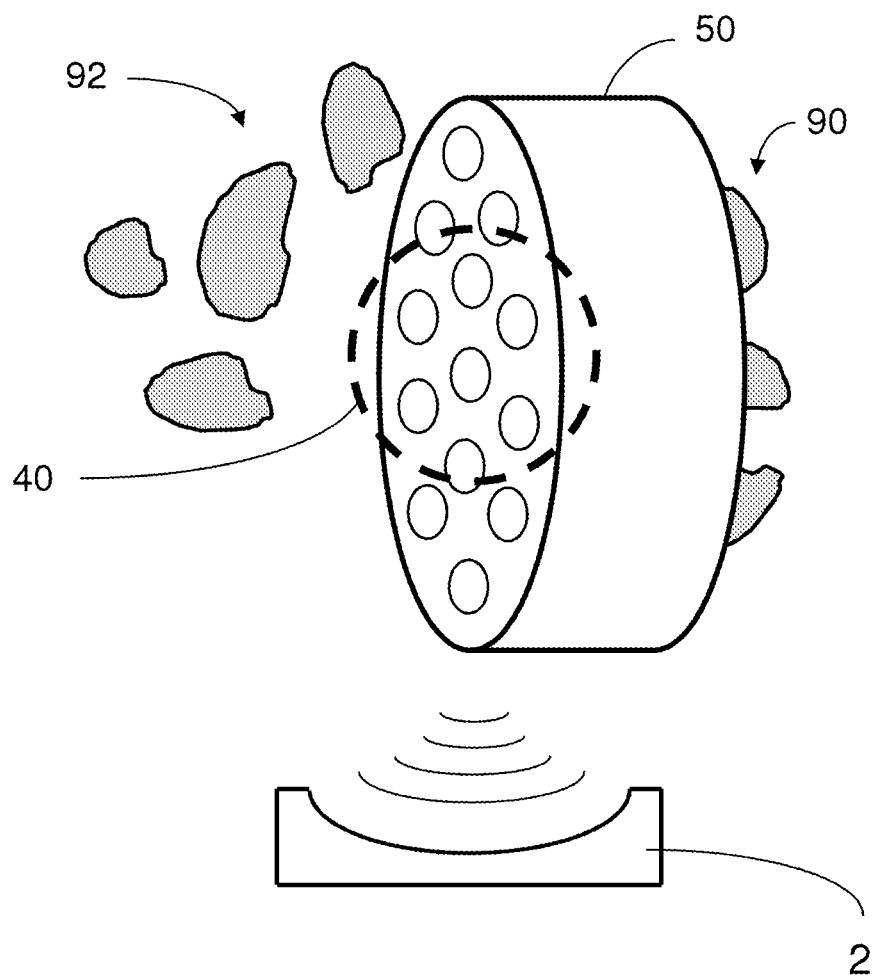
FIG. 13b-13c depict side perspective views of the retaining member of FIG. 13a treated with focused acoustic energy in accordance with some embodiments
Figure 13C:
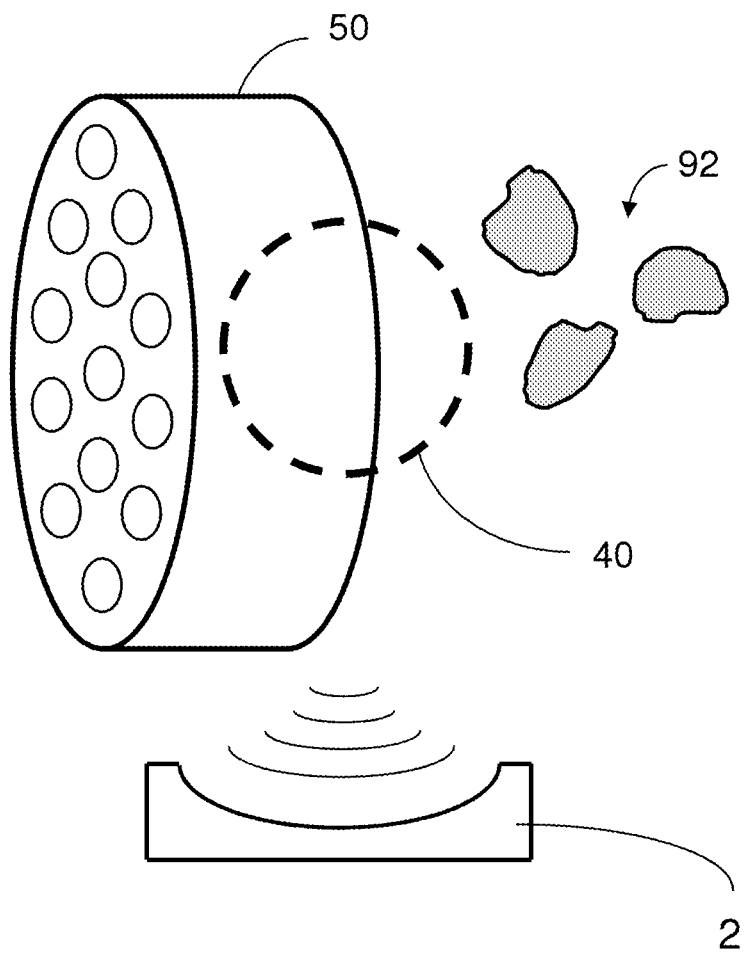

In FIG. 13b, an acoustic energy source 2 is oriented so as to direct focused acoustic energy toward the filter 50, forming a focal zone 40 at one of the surfaces of the filter. In this embodiment, when the focused acoustic energy reaches the particulate debris 90, the debris is removed or "cleaned" from the surface of the filter. In FIG. 13c, the acoustic energy source 2 is moved relative to the filter so as to direct the focused acoustic energy toward the other side of the filter 50, forming a focal zone 40 at an opposite surface of the filter. Accordingly, the particulate debris is removed from the surface of the filter upon exposure to the focused acoustic energy. In some embodiments, focused acoustic treatment does not remove material completely from the retaining member, but rather may simply move the material aside so that other particles or solution may flow through.

Flow Circuit Arrangements

Figure 14:
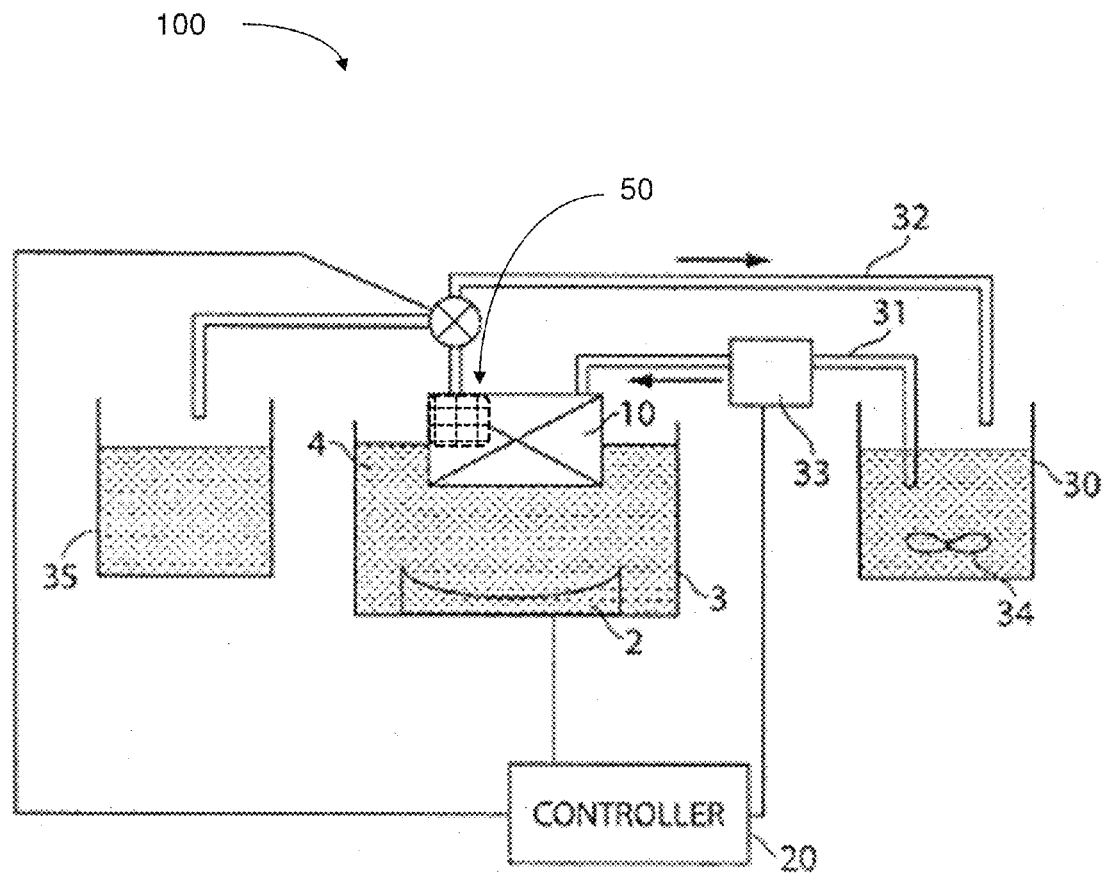
FIG. 14 is an illustrative embodiment of a sample treatment apparatus including a reservoir with an agitator in accordance with some embodiments.
Figure 15:
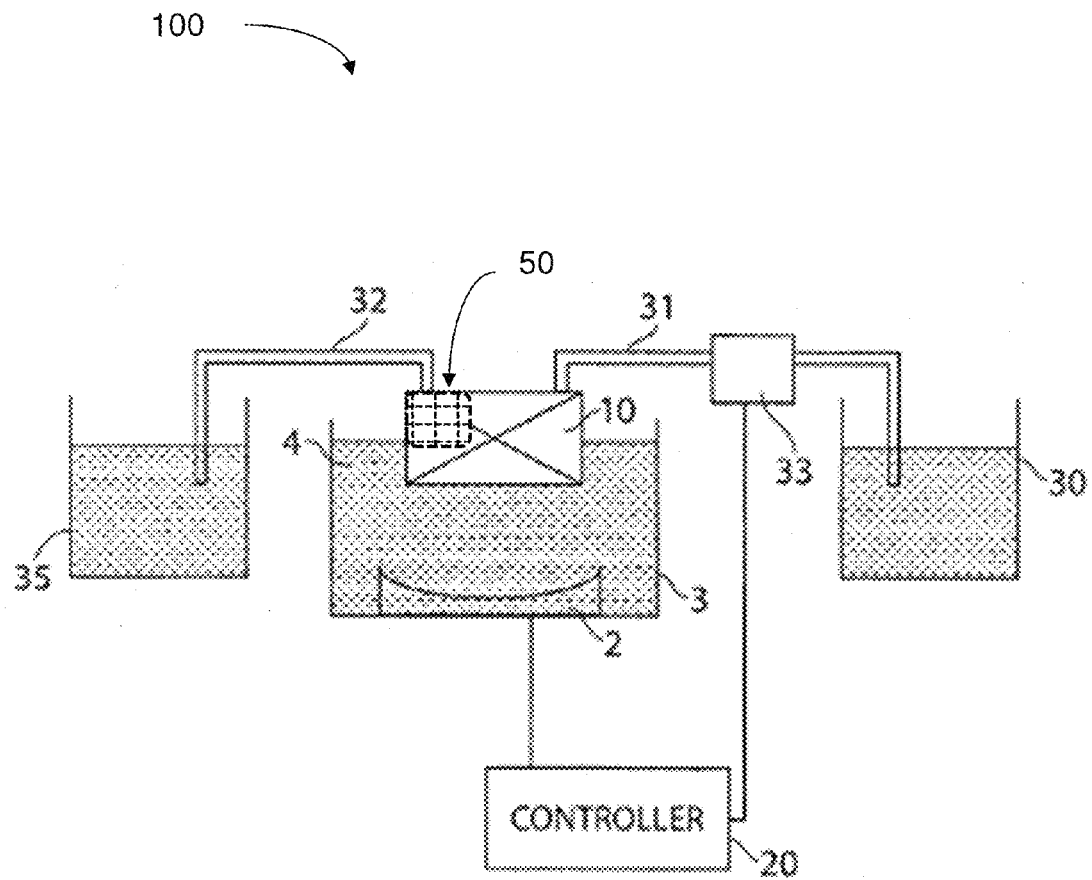
FIG. 15 is an illustrative embodiment of a sample treatment apparatus arranged for oscillating flow of material in accordance with some embodiments.
Figure 16:
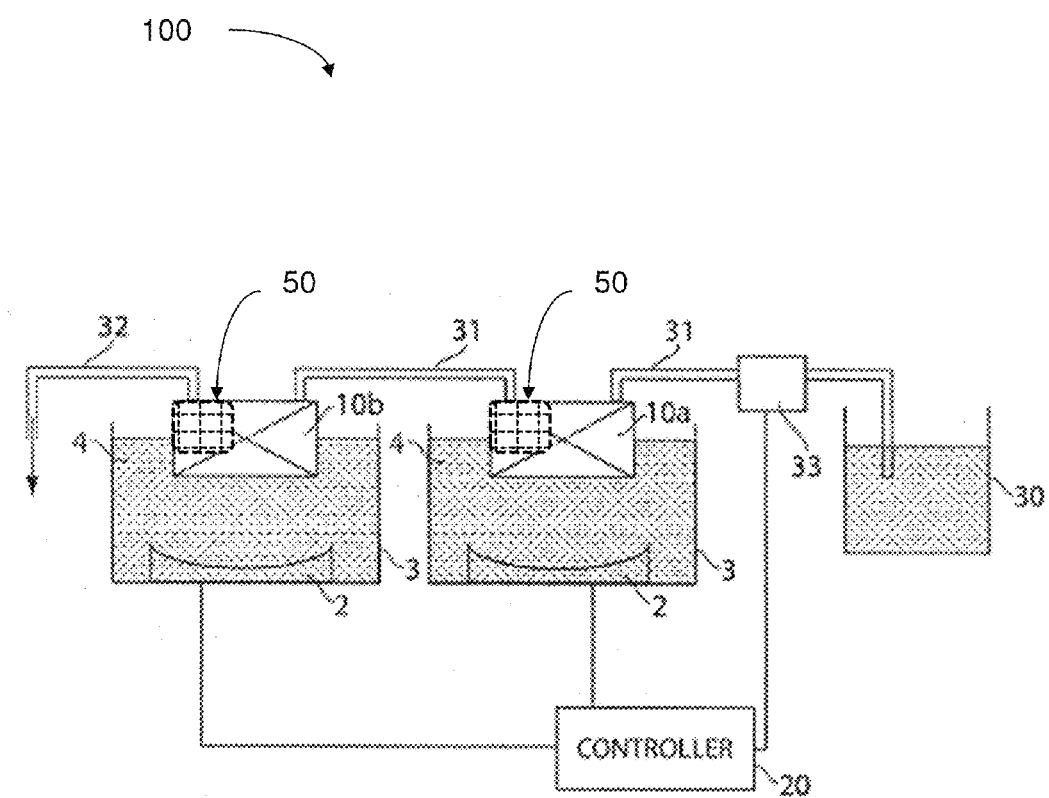
FIG. 16 is an illustrative embodiment of a sample treatment apparatus arranged for serial treatment of material using multiple processing chambers.

Additional aspects of the present disclosure relate to flow circuit arrangements for acoustically treating sample material. For example, in some embodiments, the sample material can be transferred to/from the treatment chamber through passive or active mechanisms, with the use of direct pumping methods or passive gravity driven methods. FIGS. 14-16 depict a number of illustrative embodiments of flow through arrangements that may incorporate focused acoustics and/or radiative treatment.

In some embodiments, a sample treatment system 100 may include one or more treatment chambers 10 that are fluidly coupled to a reservoir that holds material to be treated in the chamber(s). For example, as shown in FIG. 14, the inlet of a chamber 10 may be fluidly coupled to a supply conduit 31 and the outlet of the chamber 10 may be fluidly coupled to a return conduit 32. Thus, material in the reservoir 30 may be circulated through the chamber 10 at any suitable flow rate, pressure, time or other parameter so that the material is suitably processed by acoustic energy in the chamber 10. Flow of the material may be caused by gravity, by acoustic streaming (e.g., in the chamber 10), by a pump 33 (such as a syringe pump, a peristaltic pump, a gear pump, and so on), or other motive force. In some embodiments, a pressure may be maintained in the chamber 10 (and/or in the reservoir 30) by applying a pressurized gas, a pump or other component to generate the desired pressure in the desired locations. In some cases, pressurizing the material in the chamber 10 and/or elsewhere may help reduce cavitation, enhance reaction rates, and/or have other desired affects.

FIG. 14 further shows a filter 50 positioned at the outlet of the chamber 10, as similarly described above, for retaining particles of sample material that have particle sizes greater than the threshold particle size. Accordingly, the filter obstructs particles that do not meet an appropriate criterion from exiting the chamber. As a result, particles that remain within the internal volume of the chamber are further exposed to suitable focused acoustic energy and/or radiation (radiation source not shown in FIGS. 14-16). While not expressly shown in FIG. 14, the chamber may also include a radiation source for providing further treatment to the sample material.

In some embodiments of the present disclosure, the reservoir 30 may include an agitator 34, such as a mixing blade, stirrer, homogenizer or other device that functions to mechanically mix, shear or otherwise cause movement of the material in the reservoir 30. Movement of the material may have desired effects, such as pretreating the material prior to acoustic treatment, maintaining a desired distribution of material components throughout the volume in the reservoir, and so on. It can be appreciated that the agitator 34 is not required to include an impeller-like structure; for example, an acoustic transducer for generating focused or unfocused acoustic energy may be suitably provided for mixing and/or shearing the material. An arrangement like that in FIG. 14 may allow the system 100 to repeatedly expose the material to acoustic treatment so that the material has desired properties when treatment is complete.

The acoustic treatment conditions in the chamber 10 may remain constant, or nearly constant throughout the process, or the conditions may vary over time, as desired. For example, the material may initially include relatively large particles of a substance to be broken down into smaller particles and ultimately solubilized in a carrier liquid. Initial acoustic treatment conditions (as well as operation of the agitator 34) may be favorable to break the large particles down into smaller particles. After some initial treatment, the large particles may be broken down, and the acoustic treatment conditions (and the operation of the agitator 34) may be adjusted to enhance the speed and effectiveness of putting components of the small particles into solution. Adjustments to the treatment conditions may be made based on any suitable criteria, such as sensed material properties (such as particle size, density, concentration, transmittance, etc.), a time elapsed, user input, and so on.

The system 100 may optionally include a second reservoir 35 that receives material when processing of the material is determined to be complete (again, which determination may be made based on detected material properties, elapsed time, etc.). In this embodiment, the return conduit 32 includes a three-way valve (or other suitable arrangement) that permits the controller 20 to direct material to the second reservoir 35 as desired. Of course, other flow control arrangements may be used, and control of material flow to the second reservoir 35 may be based on sensed parameters, such as elapsed processing time, detected particle sizes or density, material color or other optical properties, or other characteristics of the sample material.

FIG. 15 shows another illustrative embodiment for a sample treatment system 100 that includes a first reservoir 30 fluidly coupled to a chamber 10 via a supply conduit 31, and a second reservoir 35 fluidly coupled to the chamber 10 via a return conduit 32. A filter 50 is positioned at the outlet of the chamber 10. The chamber may also include a radiation source (not expressly shown in this figure) so as to provide further treatment to the sample material. In this embodiment, material in the first reservoir 30 may flow through the chamber 10 for acoustic and/or radiation treatment, and material that passes through the filter is thereafter deposited in the second reservoir 35. In the case that subsequent acoustic and/or radiation treatment is desired, the material may be again caused to flow through the chamber 10 (and through the filter 50), albeit in the opposite direction and into the first reservoir 30 after a second treatment. Flow of the material may be caused in any suitable way, such as by a pump 33, by acoustic streaming in the chamber 10, by gravity (e.g., by establishing the level of material in one reservoir to be higher than the other, causing a siphon to be created for flow), or others. The chamber 10 and/or the conduits 31, 32 may include one or more windows, retaining members, sensors suitable to detect properties of the sample material, or other components. The detected features may be used to control various parameters of the system 100, such as flow rate, pressure, acoustic and/or radiation treatment characteristics, and so on.

In another illustrative embodiment, a sample treatment system 100 may include two or more treatment chambers 10 that are arranged in serial fashion. For example, FIG. 16 shows an embodiment in which two chambers 10 are in fluid communication with each other and a reservoir 30. Each of the chambers 10 include a filter 50 for retaining particles larger than a threshold particle size within the respective internal volume of the chamber. It can be appreciated that any suitable retaining member(s), or method in which sample material may be retained within the internal volume of a processing chamber until a particular criterion is reached, may be employed.

The first chamber 10a may be used to apply a 'pretreatment' or other first treatment to the sample material, while the second chamber 10b applies a 'finishing" or other second treatment to the material. The acoustic energy and other treatment parameters may be set and controlled independently at each chamber 10 to optimize the overall processing goals. For example, the sample material can first pass through a 'roughing' stage in the first chamber 10a to break up large chunks/clumping in the sample material (e.g., where the treatment conditions provide a general, high level mixing and homogenization of the sample) before the material passes to the next stage (e.g., a 'finishing' stage) for additional acoustic and/or radiation treatment that refines the ultimate properties of the material, such as by extracting desired materials, solubilizing components in the material, sterilization, and so on.

In some cases, the threshold particle size defined by the filter of the first chamber 10a may be different than that of the second chamber 10b. In the example above, the corresponding threshold particle size for the filter employed with the first chamber 10a used for 'roughing' may be greater than the corresponding threshold particle size for the filter used with the second chamber 10b used for 'finishing.' As many stages, i.e., chambers 10, as is necessary may be used in a system 100 like that in FIG. 16 to achieve the desired output.

Aspects of the present disclosure also relate to methods for acoustically treating material using the various systems 100 described above. For example, one method in accordance with the present disclosure involves treating a material using a system like that in FIG. 14 wherein material is agitated by an agitator in a reservoir, the material is caused to flow from the reservoir into a chamber 10, the material is exposed to focused acoustic energy and/or electromagnetic radiation in the internal volume of the chamber 10 (where the acoustic energy at a focal zone has the properties described herein), the material is permitted to flow out of the chamber after a characteristic of the material reaches a predetermined criterion (e.g., having a particle size less than a threshold particle size, exhibiting a particular degree of transmittance, presence or absence of a certain chemical or biological material, or reaching one or more different criteria), and the material is caused to flow back to the reservoir.

Optionally, a processing state of the material may be detected, e.g., while the material is in the chamber 10 or return conduit, and if the material is suitably processed (i.e., reaches one or more physical/chemical/biological criteria), the material may be caused to flow to another reservoir. Relatively large volumes of material, such as 1 gallon, 10 gallons, 100 gallons, 1000 gallons or more of material may be held in the reservoir and caused to flow in a circulatory manner through one or more chambers 10 in a continuous fashion. Thus, the treatment method may be continuously performed for 1 hour or more, with the acoustic energy source continuously operating at a power output equivalent to 200 watts or more.

Another method in accordance with the present disclosure relates to treating material using a system like that in FIG. 15, or a similar system. For example, material may be caused to flow in a first direction into a chamber 10, the material is exposed to focused acoustic energy and/or radiation in the internal volume of the chamber 10, and the material is caused to flow past a retaining member, having reached one or more appropriate criteria, and out of the chamber 10. Thereafter, the sample material may be caused to flow in a second direction opposite to the first direction into the chamber 10, where the material is again acoustically and/or radiation treated, and flows in the second direction out of the chamber 10. As such, the sample material may, again, flow through, or past, the retaining member. Flow may be caused by one or more pumps, acoustic streaming, gravity and/or other motive forces. Also, acoustic treatment may be performed in a continuous manner, for extended periods of time (over 1 hour) with the acoustic energy source 2 operation at a power output of 200 watts or greater. As with other methods in accordance with the present disclosure, various aspects may be combined together, such as chambers that include acoustic windows, chambers that include heat exchanger features, and so on.

Another method in accordance with the present disclosure relates to treating material using a system like that in FIG. 16 or a similar system. For example, material may be caused to flow into a first chamber 10, the material is exposed to focused acoustic energy and/or radiation in the internal volume of the first chamber 10, and the material is caused to flow through a first retaining member, once a first criterion is reached, and out of the first chamber 10 and into a second chamber 10, where the material is again acoustically and/or radiation treated (which may employ different parameters than that of the first treatment).

Serial treatment of the material may be repeated with three or more chambers, and the treatment conditions may be the same, or different, in the different chambers 10. Acoustic and/or radiation treatment may be performed in a continuous manner, for extended periods of time (over 1 hour) with the acoustic energy source 2 operation at a power output of 200 watts or greater. As with other methods in accordance with the present disclosure, various aspects may be combined together, such as chambers that include acoustic windows, chambers that include heat exchanger features, and so on.

Flow through acoustic processing arrangements may be used for scaling a process utilizing focused acoustical energy and/or radiation to larger volume batch and continuous process flows, such that the desired result of acoustic treatment and/or radiation can be achieved in a consistent and uniform manner on larger sample volumes that are well mixed.

Figure 17:
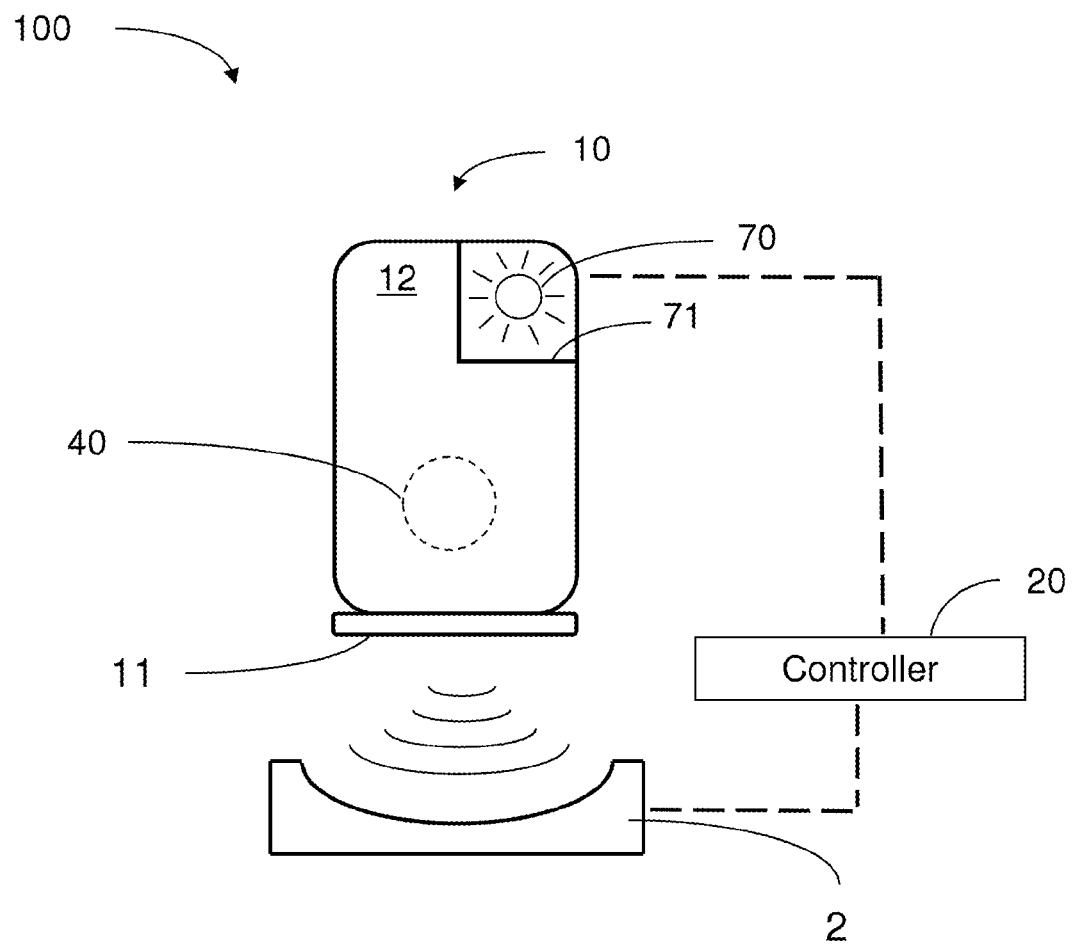
FIG. 17 is an illustrative embodiment of a sample treatment apparatus arranged for single batch vessel treatment of material.

Another method in accordance with the present disclosure relates to treating material using a single batch treatment system such as that shown in FIG. 17, or a similar system. For example, sample material may be placed in the process chamber or vessel and enclosed (e.g., capped tightly) so as to be exposed to focused acoustic energy and/or radiation within the internal volume. The material may be tested at appropriate times for certain characteristics (e.g., physical, chemical, biological, etc.). Once one or more criteria is reached, the sample may be removed from the process chamber or vessel and used subsequently for respective applications (e.g., clinical sample sterilization).

The desired result of acoustic treatment, which may be achieved or enhanced by use of ultrasonic wavetrains, can be without limitation, heating the sample, cooling the sample, fluidizing the sample, micronizing the sample, mixing the sample, stirring the sample, disrupting the sample, permeabilizing a component of the sample, forming a nanoemulsion or nanoformulation, enhancing a reaction in the sample, solubilizing, sterilizing the sample, lysing, extracting, comminuting, catalyzing, and selectively degrading at least a portion of a sample. Sonic waves may also enhance filtration, fluid flow in conduits, and fluidization of suspensions. Processes of the present disclosure may be synthetic, analytic, or simply facilitative of other processes such as stirring.

For example, altering the permeability or accessibility of a material in a controlled manner can allow for manipulation of the material while preserving the viability and/or biological activity of the material. In another example, mixing materials or modulating transport of a component into or out of materials, in a reproducible, uniform, and automated manner, can be beneficial. According to one embodiment of the system, sample processing control includes a feedback loop for regulating at least one of sonic energy location, pulse pattern, pulse intensity, duration, and absorbed dose of the ultrasound to achieve the desired result of acoustic treatment. In one embodiment, the ultrasonic energy is in the megahertz (MHz) frequency range, in contrast to classical sonic processing which typically employs ultrasonic energy in the kilohertz (kHz) frequency range.

In prior systems, when unfocused, and uncontrolled ultrasonic energy interacts with a complex biological or chemical system, the acoustic field often becomes distorted, reflected, and defocused. The net effect is that energy distribution becomes non-uniform and/or defocused compared to the input. Non-uniform reaction conditions can limit reaction applications to non-critical processes, such as bulk fluid treatment where temperature gradients within a sample are inconsequential. However, some of the non-uniform aspects are highly deleterious to samples, such as extreme temperature gradients that damage sample integrity. For example, in some instances, high temperatures generated would irreversibly denature target proteins. As another example, when improperly controlled ultrasound is applied to a bulk biological sample solution, such as for the extraction of intracellular constituents from tissue, the treatment causes a complex, heterogeneous, mixture of sub-events that vary during the course of a treatment dose. For example, the energy may spatially displace a target moiety and shift the target out of the optimal energy zone.

Additionally or alternatively, the energy may result in interference that reflects the acoustic energy. For example, a "bubble shield" may occur when a wave front of sonic energy creates cavitation bubbles that persist until the next wave front arrives, such that the energy of the second wave front is at least partially blocked and/or reflected by the bubbles. Still further, larger particles in the sample may move to low energy nodes, thereby leaving the smaller particles in the sample with more dwell-time in the high energy nodes. In addition, the sample viscosity, temperature, and uniformity may vary during the ultrasonic process, resulting in gradients of these parameters during processing. Accordingly, current processes are generally random and non-uniform, especially when applied to in vitro applications, such as membrane permeabilization, hindering the use of ultrasound in high throughput applications where treatment standardization from one sample to the next is required. As a consequence, many potential applications of ultrasound, especially biological applications, are limited to specific, highly specialized applications, such as lithotripsy and diagnostic imaging, because of the potentially undesirable and uncontrollable aspects of ultrasound in complex systems.

The use of focused acoustical energy, as described in U.S. Pat. No. 7,521,023, which is incorporated herein by reference in its entirety, and others, can overcome these limitations, and methods for acoustic treatment of a sample in an enclosed vessel are disclosed. Processing of sample material volumes greater than that of a single vessel can be achieved by transfer of the material into, and out of a focused acoustical 'process zone' or 'reaction chamber.' The material may be resident in the processing zone until the desired result is achieved (single pass), and then transferred to downstream process steps, or captured as a finished product.

Aspects of the present disclosure addresses the problem of scaling the application of focused ultrasonic energy and/or electromagnetic irradiation to treat larger volumes of material, including continuous processes as well as batch scale processing, and provides apparatus and methods for the non-contact treatment of samples with ultrasonic energy using a focused beam of energy. In various embodiments, as discussed herein, focused acoustic energy and irradiation may be used separately or in combination.

The frequency of the acoustic energy may be variable, can be in the range of about 100 kHz to 100 MHz, more preferably 500 kHz to 10 MHz, and can be focused to a processing zone of approximately 10 mm to 20 mm (and possibly of larger size with increases in energy), with the sample material passing through this zone to achieve the desired effect. For example, some embodiments in accordance with the present disclosure can treat samples with ultrasonic energy while controlling the temperature of the sample, by use of computer-generated complex wave trains, which may further be controlled by the use of feedback from a sensor. The acoustic output signal, or wave train, can vary in any or all of frequency, intensity, duty cycle, burst pattern, and pulse shape. Moreover, this treatment can be undertaken automatically under computer control, and can also be linked to instrumentation and measurement feedback from the bulk or output stream. In another example, some embodiments of the present disclosure can treat samples with ultrasonic energy by relative movement of the sample and the focus of the beam, in any or all of two or three dimensions, to ensure complete and thorough mixing within the processing zone.

In some embodiments, material can be processed in a chamber that is sealed and has one or more inlets and outlets to the chamber for effective transfer of the bulk fluid material through the chamber. The chamber can be sealed during the focused acoustic and/or radiation treatment to prevent contamination of the sample material or of the environment. In some embodiments, arrays of chambers can be used for processing multiple sample streams in parallel, where very large sample volumes are needed, such as in manufacturing process streams. In some embodiments, the chambers and/or other components that contact a material processed may be made in a disposable form, e.g., for one time use in processing a material and discarded thereafter.

The sample container can be a chamber comprised of one or more pieces and may include an acoustic 'window' through which the sonic energy passes. This window can be made from a variety of materials to optimize the desired effect, and can include glass, thin film polymers such as polyimide (e.g., Kapton®), other moldable polymers, quartz, sapphire and other materials. The chamber can have one or more inlets and one or more outlets for transfer of material into or out of the chamber. The rate at which material is transferred through the chamber can be controlled actively via a pumping system, such as a peristaltic, gear, or other pump, or passively via gravity fed methods such as elevation changes or tilting a chamber through an oscillation about its axis. The apparatus can also include an acoustically transparent material disposed between the sonic energy source and the holder. An acoustically transparent material may be effective to transmit acoustic energy emitted from one side of the acoustically transparent material to the opposite side. The sonic energy source can generate sonic energy at two or more different frequencies, optionally in the form of a serial wavetrain. The wavetrain can include a first wave component and a different second wave component. Alternatively or additionally, the wavetrain can include about 1000 cycles per burst at about a 10% duty cycle at about a 500 mV amplitude.

The window may be generally transparent to acoustic energy having a frequency of about 100 kHz to 100 MHz. In this way, the window may minimally impede the acoustic energy traveling into the internal volume. In some embodiments, the window may impede ultraviolet radiation (or other forms of radiation) from transmission therethrough, so that radiation emitted from the source 70 is substantially retained within the internal volume of the process chamber.

In some arrangements, the window may help direct the acoustic energy, e.g., the window may have a convex face or other arrangement that has a focusing or lens effect on the acoustic energy. An acoustic energy source, such as one or more piezoelectric transducers, may be spaced from the window and be arranged to emit acoustic energy having a frequency of about 100 kHz to 100 MHz so as to create a focal zone of acoustic energy in the internal volume. The system may be arranged to accommodate continuous acoustic and/or radiation treatment of material in the chamber for an extended time period, e.g., for 1 hour or more, at a relatively high intensity, e.g., at an output of the acoustic transducer of 200 watts or more, without experiencing excessive heat buildup or other problems. (In a continuous acoustic treatment, material may be caused to flow in a continuous fashion in a chamber, or may flow in an intermittent fashion. Also, the acoustic energy source may operate at a power level that varies, but on a time averaged basis operates at a relatively high power output level, e.g., 200 watts or more) This is in contrast to prior acoustic treatment arrangements in which continuous acoustic treatment for 1 hour or more could not have been achieved for a variety of different reasons, such as excessive heat buildup, failure of the acoustic source, damage to the sample material, and so on.

In some arrangements, the internal volume may be suitably sized or otherwise arranged to help expose material in the internal volume to the acoustic energy. For example, the internal volume may include walls that are located near the boundaries of an acoustic focal zone in the internal chamber to help ensure that material is maintained in or near the focal zone during treatment. In other arrangements, the internal volume may include elements that provide nucleation points for cavitation or other acoustically-caused affects. A coupling medium, which may be liquid or solid, may be arranged to transmit acoustic energy from the acoustic energy source to the window. For example, a water bath may be positioned between the acoustic energy source and the window of the chamber. In some arrangements, the chamber may be partially or completely submerged in a liquid coupling medium, such as water.

In accordance with an aspect of the present disclosure, various embodiments of the focused acoustic processing system may be arranged to accommodate continuous acoustic and radiation treatment of material in a chamber 10, or multiple chambers 10, for an extended time period, e.g., for 1 hour or more, at a relatively high intensity, e.g., at an output of the acoustic transducer of 200 watts or more, without experiencing excessive heat buildup or other problems.

In one embodiment, a piezoelectric transducer functioning at part of the acoustic energy source 2 may operate at an intensity level equal to about 286 watts for several hours in an equilibrium state, i.e., a state in which material is acoustically processed in a chamber 10 without excessive heat build up, transducer burn out or failure, or other conditions that would require stoppage of the acoustic treatment. This is in contrast to prior acoustic treatment arrangements in which continuous acoustic treatment for 1 hour or more could not have been achieved for a variety of different reasons, such as excessive heat buildup, failure of the acoustic source (e.g., due to transducer overheating and subsequent burn out), damage to the sample material, and so on.

Transducer

In certain embodiments, the sonic energy source 2 may include, for example, an ultrasound transducer or other transducer, that produces acoustic waves in the "ultrasonic" frequency range. Ultrasonic waves start at frequencies above those that are audible, typically about 20,000 Hz or 20 kHz, and continue into the region of megahertz (MHz) waves. The speed of sound in water is about 1000 meters per second, and hence the wavelength of a 1000 Hz wave in water is about a meter, typically too long for specific focusing on individual areas less than one centimeter in diameter, although usable in non-focused field situations. At 20 kHz, the wavelength may be about 5 cm, which is effective in relatively small treatment vessels.

Depending on the sample and vessel volume, preferred frequencies may be higher, for example, about 100 kHz, about 1 MHz, or about 10 MHz, with wavelengths, respectively, of approximately 1.0, 0.1, and 0.01 cm. In contrast, for conventional sonication, including sonic welding, frequencies are typically approximately in the tens of kHz, and for imaging, frequencies are more typically about 1 MHz and up to about 20 MHz. In lithotripsy, repetition rates of pulses are fairly slow, being measured in the hertz range, but the sharpness of the pulses generated may give rise to an effective pulse wavelength, or in this case, pulse rise time, with frequency content up to about 100 to about 300 MHz, or 0.1-0.3 gigahertz (GHz).

The frequency used in certain embodiments of the present disclosure also will be influenced by the energy absorption characteristics of the sample or of the chamber 10, for a particular frequency. To the extent that a particular frequency is better absorbed or preferentially absorbed by the sample material, it may be preferred. The energy can be delivered in the form of short pulses or as a continuous field for a defined length of time. The pulses can be bundled or regularly spaced.

A generally vertically oriented focused ultrasound beam may be generated in several ways by the acoustic energy source 2. For example, a single-element piezoelectric transducer, such as those supplied by Sonic Concepts, Woodinville, Wash., that can be a 1.1 MHz focused single-element transducer, can have a spherical or other curved transmitting surface that is oriented such that the focal axis is vertical. Another embodiment uses a flat unfocused transducer and an acoustic lens (e.g., the window 11 or other element) to focus the beam. Still another embodiment uses a multi-element transducer such as an annular array in conjunction with focusing electronics to create the focused beam. The annular array potentially can reduce acoustic sidelobes near the focal point by means of electronic apodizing, that is by reducing the acoustic energy intensity, either electronically or mechanically, at the periphery of the transducer. This result can be achieved mechanically by partially blocking the sound around the edges of a transducer or by reducing the power to the outside elements of a multi-element transducer. This reduces sidelobes near the energy focus, and can be useful to reduce heating of the chamber 10. Alternatively, an array of small transducers can be synchronized to create a converging beam. Still another embodiment combines an unfocused transducer with a focusing acoustic mirror to create the focused beam. This embodiment can be advantageous at lower frequencies when the wavelengths are large relative to the size of the transducer. The axis of the transducer of this embodiment can be horizontal and a shaped acoustic mirror used to reflect the acoustic energy vertically and focus the energy into a converging beam.

In certain embodiments, the focal zone can be small relative to the dimensions of the treatment chamber 10 to avoid heating of the treatment chamber 10. In one embodiment, the focal zone has a width of approximately 1 mm. Heating of the treatment chamber 10 can be reduced by minimizing acoustic sidelobes near the focal zone. Sidelobes are regions of high acoustic intensity around the focal point formed by constructive interference of consecutive wavefronts. The sidelobes can be reduced by apodizing the transducer either electronically, by operating the outer elements of a multi-element transducer at a lower power, or mechanically, by partially blocking the acoustic waves around the periphery of a single element transducer. Sidelobes may also be reduced by using short bursts, for example in the range of about 3 to about 5 cycles in the treatment protocol.

The transducer can be formed of a piezoelectric material, such as a piezoelectric ceramic. The ceramic may be fabricated as a "dome," which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses.

Typically, these domes have a longer focal length than that found in lithotriptic systems, for example, about 20 cm versus about 10 cm focal length. Ceramic domes can be damped to prevent ringing. The response is linear if not overdriven. The high-energy focus zone of one of these domes is typically cigar-shaped. At 1 MHz, the focal zone is about 6 cm long and about 2 cm wide for a 20 cm dome, or about 15 mm long and about 3 mm wide for a 10 cm dome. The peak positive pressure obtained from such systems is about 1 MPa (mega Pascal) to about 10 MPa pressure, or about 150 PSI (pounds per square inch) to about 1500 PSI, depending on the driving voltage. The focal zone, defined as having an acoustic intensity within about 6 dB of the peak acoustic intensity, is formed around the geometric focal point.

The wavelength, or characteristic rise time multiplied by sound velocity for a shock wave, is in the same general size range as a biological cell, for example about 10 to about 40 micron. This effective wavelength can be varied by selection of the pulse time and amplitude, by the degree of focusing maintained through the interfaces between the source and the material to be treated, and the like.

Another source of focused acoustic pressure waves is an electromagnetic transducer and a parabolic concentrator, as is used in lithotripsy. The excitation of such devices tends to be more energetic, with similar or larger focal regions. Strong focal peak negative pressures of about −16 MPa have been observed. Peak negative pressures of this magnitude provide a source of cavitation bubbles in water, which can be desirable in an extraction process.

Drive Electronics and Waveform Control.

One treatment protocol for treating material with acoustic energy in the chamber 10 can include variable acoustic waveforms combined with sample motion and positioning to achieve a desired effect. The acoustic waveform of the transducer may have many effects, including: acoustic microstreaming in and near cells due to cavitation, that is flow induced by, for example, collapse of cavitation bubbles; shock waves due to nonlinear characteristics of the fluid bath; shock waves due to cavitation bubbles; thermal effects, which lead to heating of the sample, heating of the sample vessel, and/or convective heat transfer due to acoustic streaming; flow effects, causing deflection of sample material from the focal zone due to shear and acoustic pressure, as well as mixing due to acoustic streaming, that is flow induced by acoustic pressure; and chemical effects. The waveform of focused sound waves can be a single shock wave pulse, a series of individual shock wave pulses, a series of shock wave bursts of several cycles each, or a continuous waveform. Incident waveforms can be focused directly by either a single element, such as a focused ceramic piezoelectric ultrasonic transducer, or by an array of elements with their paths converging to a focus. Alternatively, multiple foci can be produced to provide ultrasonic treatment to multiple treatment zones, vessels, or wells. Additionally, the flow of the sample material into, or out of the processing chamber 10 can interact with the acoustic effects, and the acoustic streaming can be modified to enhance this sample flow in a desirable manner.

The treatment protocol can be optimized to maximize energy transfer while minimizing thermal and flow effects. The treatment protocol also can effectively mix the contents of the treatment chamber 10, in the case of a particulate sample suspended in a liquid. Energy transfer into the sample can be controlled by adjusting the parameters of the acoustic wave such as frequency, amplitude, and cycles per burst. Temperature rise in the sample can be controlled by limiting the duty cycle of the treatment and by optimizing heat transfer between the treatment chamber 10 and the coupling medium 4. Heat transfer can be enhanced by making the treatment chamber 10 with thin walls, of a relatively highly thermally conductive material, and/or by promoting forced convection by acoustic streaming in the treatment chamber 10 and in the fluid bath in the proximity of the treatment chamber 10. Additionally, the chamber 10 can be modified to enhance the thermal coupling between the sample and the exterior environment by providing enhanced surface treatments such as increased area such as fins, an actively pumped water jacket, and/or high conductivity vessel materials. Monitoring and control of temperature is discussed in more detail below.

For example, for a cellular disruption and extraction treatment, an example of an effective energy waveform is a high amplitude sine wave of about 1000 cycles followed by a dead time of about 9000 cycles, which is about a 10% duty cycle, at a frequency of about 1.1 MHz. The sine wave electrical input to the transducer typically results in a sine wave acoustic output from the transducer. As the focused sine waves converge at the focal point, they can become a series of shock waves due to the nonlinear acoustic properties of the water or other fluid in the coupling medium 4. This protocol treats the material in the focal zone effectively during the "on" time. As the material is treated, it is expelled from the focal zone and new material circulates into the focal zone. The acoustic "on" and "off" times can be cycled to be effective, for example, for extracting the cellular contents of ground or particulate leaf tissue, while causing minimal temperature rise in the treatment vessel.

Further advantage in disruption and other processes may be gained by creating a high power "treat" interval alternating with a low power "mix" interval. More particularly, in this example, the "treat" interval utilizes a sine wave that has a treatment frequency, a treatment cycles-per-burst count, and a treatment peak-to-peak amplitude. The "mix" interval has a mix frequency, a mix cycles-per-burst count and a lower mix peak-to-peak amplitude. Following each of the intervals is a dead time. Of course, these relationships are merely one example of many, where one interval in considered to be high power and one interval is considered to be low power, and these variables and others can be altered to produce more or less energetic situations. Additionally, the treat function or interval and the mix function or interval could emit from different or multiple transducers in the same apparatus, optionally emitting at different frequencies.

High power/low power interval treatments can allow multiple operations to be performed, such as altering permeability of components, such as cells, within the sample followed by subsequent mixing of the sample. The treat interval can maximize cavitation and bioeffects, while the mix interval can maximize mixing within the treatment vessel and/or generate minimal heat. Adding a longer, high power "super-mix" interval occasionally to stir up particles that are trapped around the periphery of the chamber 10 can provide further benefits. This "super-mix" interval generates additional heat, so it is programmed to treat infrequently during the process, for example, every few seconds. Additionally, dead times between the mix and treat intervals, during which time substantially no energy is emitted from the sonic energy source, can allow fresh material to circulate into the energy focal zone of the target.

The waveform of the sound wave typically is selected for the particular material being treated. For example, to enhance cavitation, it can be desirable to increase the peak negative pressure following the peak positive pressure. For other applications, it can be desirable to reduce cavitation, but maintain the peak positive pressure. This result can be achieved by performing the process in a pressurized chamber 10 at a slight pressure above ambient. For example, if the waveform generated has a peak negative pressure of about −5 MPa, then the entire chamber may be pressurized to about 10 MPa to eliminate cavitation from occurring during the process. Material to be treated can be pressurized on a batch or a continuous basis within the internal volume 12 of the chamber 10. That is, a volume of material may be delivered into the internal volume 12, treated acoustically while material flow is stopped, and then a new volume of material may be delivered into the internal volume 12 once treatment of the initial volume is complete.

Typically, the shock wave is characterized by a rapid shock front with a positive peak pressure in the range of about 15 MPa, and a negative peak pressure in the range of about negative 5 MPa. This waveform is of about a few microseconds duration, such as about 5 microseconds. If the negative peak is greater than about 1 MPa, cavitation bubbles may form. Cavitation bubble formation also is dependent upon the surrounding medium. For example, glycerol is a cavitation inhibitive medium, whereas liquid water is a cavitation promotive medium. The collapse of cavitation bubbles forms "microjets" and turbulence that impinge on the surrounding material.

Control of the acoustic energy source 2 may be performed by the controller 20 using a feedback control mechanism so that any of accuracy, reproducibility, speed of processing, control of temperature, provision of uniformity of exposure to sonic pulses, sensing of degree of completion of processing, monitoring of cavitation, and control of beam properties (including intensity, frequency, degree of focusing, wave train pattern, and position), can enhance performance of the treatment system 1. A variety of sensors or sensed properties may be used by the controller 20 for providing input for feedback control. These properties can include sensing of temperature of the sample material; sonic beam intensity; pressure; coupling medium properties including temperature, salinity, and polarity; sample material position; conductivity, impedance, inductance, and/or the magnetic equivalents of these properties, and optical or visual properties of the sample material. These optical properties, which may be detected by the sensor 21 typically in the visible, IR, and UV ranges, may include apparent color, emission, absorption, fluorescence, phosphorescence, scattering, particle size, laser/Doppler fluid and particle velocities, and effective viscosity. Sample integrity or comminution can be sensed with a pattern analysis of an optical signal from the sensor 21. Particle size, solubility level, physical uniformity and the form of particles could all be measured using instrumentation either fully stand alone sampling of the fluid and providing a feedback signal, or integrated directly with the focused acoustical system via measurement interface points such as an optical window. Any sensed property or combination thereof can serve as input into a control system. The feedback can be used to control any output of the system, for example beam properties, sample position or flow in the chamber 10, treatment duration, and losses of energy at boundaries and in transit via reflection, dispersion, diffraction, absorption, dephasing and detuning.

According to certain embodiments of the present disclosure, several aspects of the treatment system 100 can enhance the reproducibility and/or effectiveness of particular treatments using ultrasonic energy in in vitro applications, where reproducibility, uniformity, and precise control are desired. These aspects include the use of feedback, precise focusing of the ultrasonic energy, monitoring and regulating of the acoustic waveform (including frequency, amplitude, duty cycle, and cycles per burst), positioning of the chamber 10 relative to the ultrasonic energy so that the sample material is uniformly treated, controlling movement or flow of the sample relative to the focus of ultrasonic energy during a processing step, and/or controlling the temperature of the sample being treated, either by the ultrasonic energy parameters or through the use of temperature control devices such as a water bath. A treatment protocol can be optimized, using one or a combination of the above variables, to maximize, for example, shearing, extraction, permeabilization, comminution, stirring, or other process steps, while minimizing undesirable thermal effects.

In one embodiment of the present disclosure, high intensity ultrasonic energy is focused on a chamber 10, and "real time" feedback relating to one or more process variables is used to control the process. In another embodiment, the process is automated and is used in a high throughput system, such as a continuous flowing stream of material to be treated, optionally segmented.

In certain embodiments, the processing system can include a high intensity transducer that produces acoustic energy when driven by an electrical or optical energy input; a device or system for controlling excitation of the transducer, such as an arbitrary waveform generator, an RF amplifier, and a matching network for controlling parameters such as time, intensity, and duty cycle of the ultrasonic energy; a system or method for transferring material into and out of the process zone, either actively or passively, to allow automation and the implementation of feedback from monitoring; a temperature sensor; a device for controlling temperature; one or more reaction chambers 10; and a sensor for detecting, for example, optical, radiative, and/or acoustic signatures. The feedback signal can also come from a signal provided by either external or integrated measurement methods such as particle size, solubility, and form factors.

It can be appreciated that adjustments which may apply to focused acoustic energy treatment described above may also apply to irradiation treatments of the sample material. For example, depending on feedback information regarding the sample (e.g., level of sterilization, whether tissue/protein damage has occurred), the energy output from the radiation source may vary appropriately.

Temperature, Cavitation, Particle Size, Solubility, and Pressure Management and Control. Visual Monitoring of the Sample Optical or video detection and analysis can be employed to optimize treatment of the sample. For example, in a suspension of biological tissue, the viscosity and/or transmittance of the mixture can increase during treatment due to the diminution of the particles by the treatment and/or by the liberation of macromolecules into the solution. Video analysis of the sample during treatment allows an automated assessment of the mixing caused by the treatment protocol. The protocol may be modified during the treatment to promote greater mixing as a result of this assessment. The video data may be acquired and analyzed by the computer control system (i.e., part of the controller 20) that is controlling the treatment process. Other optical measurements such as spectral excitation, absorption, fluorescence, emission, and spectral analysis also can be used to monitor treatment of the sample, whether in the chamber 10 or in a flow path upstream or downstream of the chamber 10. A laser beam, for example, can be used for alignment and to indicate current sample position. In certain embodiments the visual or optical detection can be performed through a window in the reaction chamber. This window can be the upper or lower window of the chamber 10, a visual window integrated into the vessel side itself, or can be a window integrated into the transfer tubing or sample reservoir.

Temperature Control

Certain applications require that the temperature of the sample being processed be managed and controlled during processing. For example, many biological samples should not be heated above 4 degrees C. during treatment. Other applications require that the samples be maintained at a certain elevated temperature during treatment. The ultrasound and radiation treatment protocol influences the sample temperature in several ways: the sample absorbs acoustic and radiation energy and converts it to heat; the sample treatment chamber absorbs acoustic and radiation energy and converts it to heat which, in turn, can heat the sample; and acoustic streaming develops within the sample treatment chamber and the coupling medium, forcing convective heat transfer between the sample treatment chamber and the coupling medium.

The acoustic waves or pulses can be used to regulate the temperature of the solutions in the treatment chamber. At low power, the acoustic energy produces a slow stirring without marked heating. Although energy is absorbed to induce the stirring, heat may be lost rapidly through the sides of the treatment chamber, resulting in a negligible equilibrium temperature increase in the sample. At higher energies, more energy is absorbed, and the temperature rises. The degree of rise per unit energy input can be influenced and/or controlled by several characteristics, including the degree of heat absorption by the sample or the treatment chamber and the rate of heat transfer from the treatment chamber to its surroundings (e.g., the coupling medium). Additionally, the treatment protocol may alternate a high-powered treatment interval, in which the desired effects are obtained, with a low power mixing interval, in which acoustic streaming and convection are achieved without significant heat generation. This convection may be used to promote efficient heat exchange or cooling.

The sample temperature may be required to remain within a given temperature range during a treatment procedure. Temperature can be monitored remotely by, for example, an infrared sensor. Temperature probes such as thermocouples may not be particularly well suited for all applications because the sound beam may interact with the thermocouple and generate an artificially high temperature in the vicinity of the probe. Temperature can be monitored by the same computer that controls acoustic waveform. The control responds to an error signal which is the difference between the measured actual temperature of the sample and the target temperature of the sample. The control algorithm can be as a hysteritic bang-bang controller, such as those in kitchen stoves, where, as an output of the control system, the acoustic energy is turned off when the actual temperature exceeds a first target temperature and turned on when the actual temperature falls below a second target temperature that is lower than the first target temperature. More complicated controllers can be implemented. For example, rather than simply turning the acoustic signal on and off, the acoustic signal could continuously be modulated proportionally to the error signal, for example, by varying the amplitude or the duty cycle, to provide finer temperature regulation.

In the application of a bang-bang control algorithm for a multiple sample format, once a maximum temperature value has been exceeded and the sonic energy is turned off for a particular sample, an alternative to waiting for the sample to cool below a selected temperature before turning the sonic energy on again, is to move on to the next sample, or increase the flow rate of new sample material into the treatment chamber. Another alternative is to switch to a predefined "cooling" waveform which promotes convection without adding significant heat to a particular sample, and synchronizing this cycle with the introduction of new sample material to the chamber.

Cavitation Control

In some applications, it can be preferable to treat the sample with as much energy as possible without causing cavitation. This result can be achieved by suppressing cavitation. Cavitation can be suppressed by pressurizing the treatment chamber above ambient, often known as "overpressure," to the point at which no negative pressure develops during the rarefaction phase of the acoustic wave. This suppression of cavitation is beneficial in applications such as cell transformation where the desired effect is to open cellular membranes while maintaining viable cells. In other applications it may be desirable to enhance cavitation. In these applications, a "negative" overpressure or vacuum can be applied to the region of the focal zone.

The control of cavitation in the sample also can be important during acoustic treatment processes. In some scenarios, the presence of small amounts of cavitation may be desirable to enhance biochemical processes; however, when large numbers of cavitation bubbles exist they can scatter sound before it reaches the target, effectively shielding the sample.

Cavitation can be detected by a variety of methods, including acoustic and optical methods. An example of acoustic detection is a passive cavitation detector (PCD) which includes an external transducer that detects acoustic emissions from cavitation bubbles. (That is, the PCD may be external to the chamber 10, e.g., the PCD may be located in the coupling medium 4.) The signal from the PCD can be filtered, for example using a peak detector followed by a low pass filter, and then input to a controlling computer (part of controller 20) as a measure of cavitation activity. The acoustic signal could be adjusted in ways similar to those described in the temperature control example to maintain cavitation activity at a desired level.

Overpressure: Increased pressure in the chamber 10 is one technique for controlling cavitation. Overpressure tends to remove cavitation nuclei and increases the energy level required to create cavitation. Motes in the fluid are strongly affected by overpressure and so cavitation in free-fluid is often dramatically reduced, even by the addition of one atmosphere of overpressure. Nucleation sites on the chamber 10 walls tend to be more resistant to overpressure; however the cavitation tends to be restricted to these sites and any gas bubbles that float free into the free-fluid are quickly dissolved. By increasing the ambient pressure of the system, the pressures required for bubble nucleation and collapse increase, thus increasing the force imparted by collapse of the cavitation bubble. This relationship is roughly linear—that is, doubling the ambient pressure of the system doubles the resulting force of bubble collapse. Careful system design to accommodate higher overall pressures can allow this to scale by many factors. Overpressure may be applied to the treatment chamber, an array of treatment chambers, the treatment coupling medium and vessel, or to the entire system to achieve a higher than atmospheric pressure in the region of the focal zone.

Degassing: Reducing the gas content of the material fluid tends to reduce cavitation, again by reducing cavitation nuclei and making it harder to initiate cavitation. Another method of controlling cavitation or the effects of cavitation is to control the gasses that are dissolved in the sample fluid. For instance, cavitation causes less mechanical damage in fluid saturated with helium gas than in fluid saturated with argon gas.

Monitoring of Cavitation

A variety of methods may be employed to detect cavitation. For example, acoustic emissions, optical scattering, high-speed photography, mechanical damage, and sonochemicals can be used. As described above for monitoring temperature, information from cavitation detection can be used by the system to produce an output that selectively controls exposure of a sample to sonic energy in response to the information. Each of these methods to monitor cavitation are described more fully below.

Acoustic emissions: Bubbles are effective scatterers of ultrasound. The pulsation mode of a bubble is referred to as monopole source, which is an effective acoustic source. For small, generally linear oscillations, the bubble simply scatters the incident acoustic pulse. However, as the response becomes more nonlinear, it also starts to emit signals at higher harmonics. When driven harder, the bubbles start to generate subharmonics as well. Eventually as the response becomes a periodic or chaotic, the scattered field tends towards white noise. In the scenario where inertial collapses occur, short acoustic pressure pulses are emitted. An acoustic transducer can be configured to detect these emissions. There is a detectable correlation between the onset of the emissions and cell disruption.

Optical scattering: Bubbles also scatter light. When bubbles are present, light is scattered. Light can normally be introduced into the system using fiber optic light sources so that cavitation can be detected in real-time, and therefore can be controlled by electronic and computer systems. High-speed photography: Bubbles can be photographed. This method typically requires high-speed cameras and high intensity lighting, because the bubbles respond on the time frame of the acoustics. It also requires good optical access to the sample under study. This method can give detailed and accurate data and may be a consideration when designing systems according to the present disclosure. Stroboscopic systems, which take images far less frequently, can often give similar qualitative performance more cheaply and easily than high-speed photography.

Mechanical damage: Cavitation is known to create damage to mechanical systems. Pitting of metal foils is a particularly common effect, and detection method. There is a correlation between the cavitation needed to pit foils and to disrupt cells.

Sonochemicals: A number of chemicals are known to be produced in response to cavitation. The yield of these chemicals can be used as a measure of cavitational activity. A common technique is to monitor light generation from chemicals, such as luminol, that generate light when exposed to cavitation. Sonochemical yield usually cannot be done during cell experiments but can be done independently under identical conditions, and thereby, provide a calibrated standard.

Materials for Treatment

A. Biological Materials

Many biological materials can be treated according the present disclosure. For example, such materials for treatment include, without limitation, growing plant tissue such as root tips, meristem, and callus, bone, yeast and other microorganisms with tough cell walls, bacterial cells and/or cultures on agar plates or in growth media, stem or blood cells, hybridomas and other cells from immortalized cell lines, and embryos. Additionally, other biological materials, such as serum and protein preparations, can be treated with the processes of the present disclosure, including sterilization.

B. Binding Materials

Many binding reactions can be enhanced with treatments according to the present disclosure. Binding reactions involve binding together two or more molecules, for example, two nucleic acid molecules, by hybridization or other non-covalent binding. Binding reactions are found, for example, in an assay to detect binding, such as a specific staining reaction, in a reaction such as the polymerase chain reaction where one nucleotide molecule is a primer and the other is a substrate molecule to be replicated, or in a binding interaction involving an antibody and the molecule it binds, such as an immunoassay. Reactions also can involve binding of a substrate and a ligand. For example, a substrate such as an antibody or receptor can be immobilized on a support surface, for use in purification or separation techniques of epitopes, ligands, and other molecules.

C. Chemical and Mineral Materials

Organic and inorganic materials can be treated with controlled acoustic pulses according to the methods of the present disclosure. The sonic pulses may be used to commute a solid material, particularly under a feedback control regime, or in arrays of multiple samples. As with biological samples, individual organic and inorganic samples in an array can be treated in substantial isolation from the laboratory environment. Beside altering their physical integrity, materials can be dissolved in solvent fluids, such as liquids and gasses, or extracted with solvents. For example, dissolution of polymers in solvents can be very slow without stirring, but stirring multiple samples with current methods is difficult and raises the possibility of cross-contamination between samples. However, stirring of multiple samples without cross-contamination between samples can be accomplished with apparatus and methods of the present disclosure.

Treatment Applications

A. Altering Cell Accessibility

Sonicators can disrupt cells using frequencies around 20 kHz. It is generally thought there are two ways in which ultrasound can affect cells, namely by heating and by cavitation, which is the interaction of the sound wave with small gas bubbles in the sample. Heating occurs primarily due to absorption of the sound energy by the medium or by the container. For dilute aqueous systems, it is absorption by the container that is a main source of the heating. Heating is not desirable in some treatment applications, as described herein. The heating associated with the compression and cooling associated with the rarefaction of a sound wave is relatively small, even for intense sound.

In accordance with the present disclosure, controlled sonic pulses in a medium are used to treat a sample containing biological material. The pulses can be specifically adapted to preferentially interact with supporting matrices in a biological material, such as plant cell walls or extracellular matrices such as bone or collagen, thereby lessening or removing a barrier function of such matrices and facilitating the insertion of extracellular components into a cell. In this application, the cell is minimally altered and cell viability is preserved. These pulses can be caused by shock waves or by sound waves. The waves can be created external to the sample, or directly in the sample, via applied mechanical devices. In experiments where thermal effects are negligible, there typically is no lysis, unless cavitation is present. Other modes of sonic energy can have different effects than disrupting a matrix and can be used either with pre-treatment, with disrupting sonic energy, or by themselves. For, example the conditions to disrupt a matrix can be different from those to permeabilize a cell membrane.

There are many possible mechanisms by which cavitation may affect cells and there is no consensus as to which mechanisms, if any, dominate. The principle mechanisms are thought to include shear, microjets, shock waves, sonochemistry, and other mechanisms.

B. Extracting

In a variation of the method to alter cellular accessibility described above, controlled pulses in a medium can be used to treat a sample containing biological material to extract a fraction or fractions of the biological material. The pulses are specifically adapted to preferentially interact with supporting matrices, such as plant cell walls or extracellular matrices such as bone or collagen, or materials having differences in rigidity or permeability in a biological material, thereby lessening or removing a barrier function of such matrices or materials. These pulses can be caused by shock waves or by sound waves. The waves can be created external to the sample, or directly in the sample, via applied mechanical means.

The supporting matrix of a biological sample can be disrupted without disrupting one or more selected internal structures of the cells contained within the matrix. Representative examples of such samples are: i) bone, in which a rigid matrix contains living cells of interest; ii) mammalian tissue samples, which contain living cells embedded in a matrix of elastic connective tissue and "glycocalyx" or intercellular matrix; and iii) plant tissues, such as leaves, which contain cells in a matrix of cellulose, often crosslinked with other materials, of moderate rigidity.

Virtually all living cells are gelatinous in texture, and can be deformed to some extent without rupture or internal damage. Matrices, in contrast, are designed to support and protect cells, as well as to achieve other biological functions. In the three examples above, the matrices of bone and leaves are designed to provide rigidity to the structure, while the support of most collagenous matrices has a strongly elastic character. Thus, different protocols for example, amplitude, duration, number of pulses, and temperature of sample, may be used to disrupt different matrices by mechanical means without damaging the cellular material.

Three areas to optimize for extraction are treatment waveform, mixing waveform, and positioning or dithering. One method to determine the appropriate treatment and positioning parameters for a target sample for extraction purposes is described below.

First, a solid sample is placed in a volume of liquid in about a 1:1 ratio (weight/volume), in a treatment chamber. For example, 0.25 ml of methanol is added to 0.25 gm of leaf tissue in a 0.5 ml treatment chamber. A single sample is placed within the focal zone of the sonic apparatus. Without using the treatment protocol, the mixing waveform is adjusted to provide "stirring" of the sample at the lowest amplitude, fewest cycles/burst, and lowest duty cycle. After the mixing waveform protocol is defined, the disruption treatment waveform is adjusted by immobilizing the target sample in the focal zone such that there is no mixing and no sample movement, such as dithering. Using a sonic energy source such as a piezoelectric transducer, the sample is subjected to a minimum number of cycles per burst, for example, three. For extraction purposes, the amplitude is initially used with a nominal 500 mV setting. A portion of the sample is treated and inspected under a microscope for signs of membrane disruption. Such inspection can be done in conjunction with dyes that stain intracellular organelles. The number of cycles/burst is then increased until a particular desired tissue disruption level is achieved in the immobilized portion of tissue. With a fresh sample, and with a 1:1 ratio of tissue to liquid, the temperature of the sample is monitored during a million cycle total treatment with an infra-red sensor directed to the top of a thin polyethylene film covering the sample vessel. The duty cycle is adjusted to keep the temperature within predefined ranges, such as 4 degrees C. within +/−2 degrees C. As discussed above, the different phases of extraction can be performed with different treatment chambers arranged in series (as in FIG. 16) or with the same chamber (e.g., where material flows in an oscillating manner through the chamber 10). The different chambers, or treatment conditions, may be adjusted to achieve the desired result for each stage in the process.

C. Introducing a Molecule into or Removing a Molecule from a Cell

Once a sample having a matrix has been sufficiently weakened or attenuated, but not to the point where a substantial number of cells contained within the matrix are killed or lysed, an exposed target cell or cells become amenable to insertion of exogenous molecules by techniques such as transfection or transformation. With some matrices, it may be convenient to isolate the cells from the matrices and then to transfect the cells. In other cases, it will be preferable, particularly in an automated system, to perform the transfection directly on the treated tissue sample, using solutions and conditions adapted from known techniques. Alternatively, in situations where a cell to be treated is not situated within a matrix, the cell can be directly treated according to the process below without having to pre-treat the matrix. While the treatment below is described mainly for transfection, methods and apparatus according to the present disclosure are equally applicable to a transformation process or other processes to introduce an exogenous material into a permeabilized cell membrane.

The waveforms used to alter the permeability of a cell are refined depending on the particular application. Typically, the shock wave is characterized by a rapid shock front with a positive peak pressure, for example about 100 MPa, and a negative peak pressure, for example about negative 10 MPa. This waveform is of a few microsecond duration, on the order of about 5 microseconds. If the negative peak is greater than about 1 MPa, cavitation bubbles may form. Cavitation bubble formation is also dependent upon the surrounding medium. For example, glycerol is a cavitation inhibitive medium; whereas, liquid water is a cavitation promotive medium. The collapse of cavitation bubbles forms "microjets" and turbulence that impinge on the surrounding material.

Sound waves, namely acoustic waves at intensities below the shock threshold, provide an alternative means of disrupting the matrix to allow access to the plasma membranes of the cells to allow transformation. Such sound waves can be generated by any known process. As biological material is subjected to subzero temperatures, for example about negative 5 degrees C., most but not all of the water is in the solid phase. However, in certain biological tissues micro-domains of liquid water still remain for several reasons, such as natural "antifreeze" molecules or regions of higher salt concentration. Therefore, as a sample temperature is varied during the treatment with sound or shock waves, microdomains of liquid water are able to form shock waves and induce cavitation bubble formation and collapse, with the resultant shear stresses that impinge on surrounding tissues. Indeed, gradual alteration of the sample temperature can be desirable, as it provides focused domains of liquid water for impingement on the surrounding material. The waves can be applied to the samples either directly, as piezoelectric pulses, or via an intervening medium. This medium may be water, buffer, stabilizing medium for the target material to be isolated, or extraction medium for the target. An intervening medium also can be a solid, formed of a material which is intrinsically solid, or of a frozen solution.

At that point, or, optionally, previously, a solution or suspension containing the material to be incorporated into the cells is added to the sample. In one embodiment, the exogenous material is incorporated into the cells in a conventional manner, as is known in the art for cells with exposed plasma membranes. In another embodiment, acoustic energy is used to transiently permeabilize a plasma membrane to facilitate introduction of exogenous materials into the cells.

The exogenous material may be present in the sample during the weakening of the matrix by acoustic energy. Even when the cells remain intact, as determined by dye exclusion or other viability measurements, the process of weakening the cell matrix by acoustic energy transiently destabilizes the plasma membranes, increasing the uptake of exogenous macromolecules and structures. If a further increase in the rate of incorporation is needed, then the intensity or time of application of acoustic energy is slightly increased until the cell membrane becomes transiently permeable. For example, a gentle pulse or wave is applied to the mixture, with a predetermined amplitude. This amplitude can be determined readily in separate experiments on samples of the same type to transiently make a plasma membrane of a cell type porous, in a similar empirical manner to the steps described above for determining an appropriate treatment to disrupt a matrix. During the transient porous state, exogenous materials diffuse into the cell and the materials are trapped there once the sonic or shock pulse is removed.

A major advantage of these methods for transfection, or other incorporation of exogenous material into living cells, is that the methods are readily amenable to scale-up, to automation, and to marked reduction in sample size and reagent volume. Thus, the methods are adaptable to large scale automation, in large part because they do not require the isolation of the cells from their matrix. Additionally, these methods are amenable to a continuous flow process such as those described herein. For example, the sonic energy treatment can be different for permeabilization than for sterilization, but the sample to be treated can be flowed through an apparatus similar to that described in FIG. 14.

The number of cells per ml of media is also important factor for cellular applications to use acoustics effectively the concentration of the cells should not be too low (as the energy generated and utilized depends on the concentration of cells) or too high (viscosity is high). Additionally, with the process of permeabilization and with the mixing profile, other techniques of gene transfer may be augmented. Examples include, calcium phosphate coprecipitation, electroporation, and receptor-dependent processes.

D. Sterilizing

The terms "sterilize," "disinfect," "preserve," decontaminate," "inactivation," "disinfect," and "kill" are used interchangeably herein, unless otherwise demanded by the context. "Sterilization," namely killing of all organisms, may not be synonymous in certain operations with "decontamination," for example, when the contaminant is non-living, such as a protein or prion. These terms, typically, mean the substantial elimination of or interference with any activity of a particular organism and/or particle.

It can be appreciated that irradiation methods in accordance with the present disclosure may be used with or without focused acoustics in systems described herein for sterilizing sample material.

Methods for permeabilization and extraction, described above, can be modified to sterilize a sample. The apparatus and methods for sterilizing can be optimized for efficient sterilization of particular materials in particular volumes and containers. For a particular material to be sterilized, an initial set of conditions is selected. Such conditions can include selection of a type of sonic pulse generator, intensity of sonic energy, frequency of sonic energy, where relevant, and/or like variables. The conditions also can include volume, mode of transport, and/or exposure of the materials to be sterilized. Then, the initial conditions and near variants are applied to the sample, and the percentage of cells or viruses killed is determined by standard assay conditions. Further variables are selected for change. Accordingly, a zone of maximal killing of the test organism is found. Finally, other variables, such as flow rate and/or length and/or intensity of sonic exposure, are optimized to provide both a technical solution and a commercially useful solution to the problem of sterilizing a particular material. Any of these empirically determined values can be programmed into a control system of an apparatus used for sterilization to actively control sterilization, or the apparatus can have these values previously determined such that a user need only select a predetermined sterilization mode and the apparatus.

For many liquids, adequate sterilization is provided by destroying the cell walls of bacteria, fungi, and other living cells. This result is accomplished by using frequencies and wavelengths of sound which preferentially excite the membranes of the cells while minimally heating the solution until the cells are lysed. In most cellular organisms, opening the membrane and allowing the contents to mix with an extracellular fluid will kill the organism.

Viruses can be opened to the solution by similar processing. In the case of viruses, exposure of their internal nucleic acid to the solution may not be adequate to completely inactivate them, since the naked DNA or RNA can also be infectious. Adjuncts such as iodine or nucleic-acid digesting enzymes in the solution can be provided to complete the inactivation of the viruses.

Bodily fluids are routinely analyzed as a part of clinical pathology, with the most common fluids analyzed in clinical environments being blood (serum/plasma) and urine. Efficient sterilization of these samples is important because pre-clinical analytical samples, such as blood/plasma, may give rise to a risk of transmission of infectious diseases within analytical laboratories. Ultraviolet (e.g., UVC) radiation may be effective to inactivate spores and infectious microbes, however, the efficacy of ultraviolet radiation varies widely depending on how the radiation is applied and the type of microbe (e.g., virus, bacteria, fungi). Focused acoustic processing may enhance the uniformity of sample exposure to ultraviolet radiation and may further reduce the potential risk of exposure of operators to non-sterilized samples. Based on different applications, pre-clinical samples may be processed in batch mode (e.g., using a single non-flow through treatment vessel) or in continuous flow mode (e.g., incorporating a series of inlets and outlets). Physical, chemical and/or biological characterization may also be used during and/or after the sterilization process to ensure that the sample is fully sterilized.

As an example, with expanding populations, blood banking and transfusion medicine has increased demands. Needless to say, pooling of blood samples originating from different donors increases overall risk of infections. Accordingly, appropriate virucidal procedures are important to ensure adequate levels of safety with respect to the transmission of infectious diseases, such as through the hepatitis B virus (HBV), hepatitis C virus (HCV), human immune deficiency virus (HIV), etc. Thus, ultraviolet radiation (e.g., UVC) may be employed to sterilize such samples, and can be further improved when implemented along with focused acoustic energy (e.g., adaptive focused acoustics).

As another example, certain clinical applications may require purification of drinking water and various solutions (e.g., other types of water, saline). Ultraviolet radiation (e.g., UVC) may be used to sterilize water and other fluids, and the efficacy can be enhanced considerably when used in conjunction with focused acoustic energy (e.g., adaptive focused acoustics).

E. Mixing, Stirring, and Heating

In fluid samples, including powdered and granular media and gasses, sample mixing is conventionally performed by vortexing or stirring, or other methods such as inversion of a sample containing an air space, and shaking. Vortexing is essentially achieved by mechanical motion of the entire vessel while stirring involves mechanical contact of a driven device with a fluid. Stirring is accomplished with a variety of devices, for example with propellers, impellers, paddles, and magnetic stir bars. One problem with these methods is that it is difficult to increase their scale in order to handle dozens or hundreds of sample vessels at once. Another problem with these methods is the difficulty of mixing multiple samples while keeping the each sample substantially free from contamination. As described in more detail below, methods according to the present disclosure can use sonic energy to mix a sample while avoiding problems with contamination. Factors, such as focusing the sonic energy, as well as otherwise controlling an acoustic waveform of the sonic energy, can be used to selectively mix a sample, for example, through acoustic streaming and/or microstreaming.

A fluid sample can be mixed controllably using the systems described herein. No direct contact between the material to be mixed and the sonic energy source is required. When the material to be mixed is in a treatment chamber, the treatment chamber itself is not necessarily touched by the source and is typically coupled to the source by a coupling medium.

F. Enhancing Reactions and Separations

In certain embodiments, temperature, mixing, or both can be controlled with ultrasonic energy to enhance a chemical reaction. For example, the association rate between a ligand present in a sample to be treated and an exogenously supplied binding partner can be accelerated.

In another example, an assay is performed where temperature is maintained and mixing is increased to improve association of two or more molecules compared to ambient conditions. It is possible to combine the various aspects of the process described herein by first subjecting a mixture to heat and mixing in order to separate a ligand or analyte in the mixture from endogenous binding partners in the mixture. The temperature, mixing, or both, are changed from the initial condition to enhance ligand complex formation with an exogenously supplied binding partner relative to ligand/endogenous binding partner complex formation at ambient temperature and mixing. Generally, the second temperature and/or mixing conditions are intermediate between ambient conditions and the conditions used in the first separating step above. At the second temperature and mixing condition, the separated ligand is reacted with the exogenously supplied binding partner.

Polymerase Chain Reaction ("PCR") Thermal Cycling

One of the bottlenecks of the PCR technique is cooling time. The heating cycle is rapid; however, cooling is limited by convection. Even in biochip formats, in which DNA or another target molecule is immobilized in an array on a microdevice, there is no "active" cooling process. However, certain embodiments of the present disclosure can be used to overcome this bottleneck.

In certain embodiments, a treatment process can be used to both heat and cool the sample rapidly with little overshoot from a baseline temperature at which the primer and target to be amplified anneal. The process can be summarized as follows. A sample is treated with relatively high power sonic energy such that the sample absorbs sonic energy and is heated. Then, the sample is mixed at low power to cool the sample by forcing convection, which may be accomplished in conjunction with a cool water bath. The heating and cooling steps can be performed in the same chamber 10, or alternately in separate chambers 10, e.g., in a system like that in FIG. 16. The material can be controlled by the timing of the transfer mechanism, such as the pump, to allow discrete processing times 'in chamber' before discharging the material and bringing in new material. This can provide time for process steps such as processing, mixing, cooling and others to fully develop before introducing new unprocessed sample to the chamber.

G. Purification, Separation, and Reaction Control

Focused sonic fields can be used to enhance separations. As noted elsewhere, sonic foci can be used to diminish or eliminate wall effects in fluid flow, which is an important element of many separation processes, such as chromatography including gas chromatography, size exclusion chromatography, ion exchange chromatography, and other known forms, including filed-flow fractionation. The ability to remotely modulate and/or reduce or eliminate the velocity and concentration gradients of a flowing stream is applicable in a wide variety of situations.

Sonic fields also can be used to minimize concentration polarization in membrane processes, including particle classification, filtration of fine particles and colloids, ultrafiltration, reverse osmosis, and similar processes. Concentration polarization is the result of the tendency of filtered material to be present at high concentration in a layer on the filter. This layer has a low fluid concentration and, thus, diminishes the rate of filtration as the filtered solution becomes more concentrated, or as the layer thickens. This layer can be stirred remotely by focused sonic energy of low to moderate intensity. Flow rate, thus, can be enhanced without significant cost in energy or membrane life.

H. Further Uses for Remotely Actuated and Controlled Solution Mixing with Sonic Energy Control of sonic energy emission, sonic energy characteristics, and/or location of a target relative to sonic energy also can be used to pump and control the flow rate of liquids, especially in capillaries; enhance chemical reactions, such as enhancing second-order reaction rates; increase effective Reynolds number in fluid flow; and control the dispensing of semi-solid substances.

By focusing sonic energy and positioning it near a wall of a chamber or another discontinuity in a fluid path, many local differences in the distribution of materials within a sample and/or spatially-derived reaction barriers, particularly in reactive and flowing systems, can be reduced to the minimum delays required for microscopic diffusion. Put differently, enhanced mixing can be obtained in situations where imperfect mixing is common.

The controller 20 may include any suitable components to perform desired control, communication and/or other functions as described above. For example, the controller 20 may include one or more general purpose computers, a network of computers, one or more microprocessors, etc., for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the acoustic energy source 2, a pump 33, etc., as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the material in a chamber 10, a video camera or other imaging device to capture and analyze image information regarding the chamber 10 or other components, position sensors to indicate positions of the acoustic transducer 2 and/or the vessel 10, and so on), user data input devices (such as buttons, dials, knobs, a keyboard, a touch screen or other), information display devices (such as an LCD display, indicator lights, a printer, etc.), and/or other components for providing desired input/output and control functions.

While aspects of the present disclosure have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the present disclosure.

The controller 20 may include a system control circuit that has any suitable components to perform desired control, communication and/or other functions. For example, the system control circuit may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the sample holder, initial substrate or other components, position sensors to indicate positions of the acoustic transducer 14 and/or the sample holder or initial substrate, and so on), user data input devices (such as buttons, dials, knobs, a keyboard, a touch screen or other), information display devices (such as an LCD display, indicator lights, a printer, etc.), and/or other components for providing desired input/output and control functions.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited. While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

What is claimed is:

1. A method of sample treatment, comprising:
moving material to an inlet of a chamber, the chamber defining an internal volume and having an outlet to discharge an outflow of material from the internal volume;
exposing material located within the internal volume of the chamber to focused acoustic energy having a frequency of about 100 kHz to 100 MHz and a focal zone of acoustic energy in the internal volume;
retaining a portion of the material at a region of the chamber using a particle size filter based on whether the portion of the material has a characteristic that meets a criterion; and
permitting flow of the portion of the material out of the outlet and from the internal volume of the chamber after exposure to the focused acoustic energy.

2. The method of claim 1, wherein the particle size filter is located at the inlet, the method further comprising flowing the portion of the material through the inlet of the chamber and into the internal volume only if the characteristic of the portion of the material does not meet the criterion.

3. The method of claim 1, wherein the particle size filter is located at the outlet, and the step of permitting flow comprises flowing the portion of the material through the outlet and out of the chamber only if the characteristic of the portion of the material does not meet the criterion.

4. The method of claim 1, wherein the characteristic of the portion of the material is particle size of particles in the portion of the material, and the criterion is that the particle size of particles is above a threshold particle size.

5. The method of claim 1, wherein exposing the material to acoustic energy comprises reducing an average particle size of the material.

6. The method of claim 5, wherein the material comprises cells and reducing the average particle size of the material comprises lysing the cells.

7. The method of claim 5, wherein the material comprises solid particles and reducing the average particle size of the material comprises fragmenting the solid particles.

8. The method of claim 1, wherein retaining the portion of the material at a region of the chamber comprises preventing the portion of the material from exiting the internal volume of the chamber through the outlet.

9. The method of claim 8, wherein preventing the portion of the material from exiting the internal volume of the chamber comprises obstructing particles that meet the criterion from flowing through the particle size filter located at the outlet of the chamber.

10. The method of claim 9, further comprising exposing the particle size filter to the focused acoustic energy such that a portion of the particle size filter is located at least partially within the focal zone of acoustic energy.

11. The method of claim 1, wherein the characteristic is optical transmittance, and the criterion is that the portion of the material has an optical transmittance below a threshold transmittance value.

12. The method of claim 1, wherein the characteristic is a chemical or biological characteristic, and the criterion is that the portion of the material has a sensed chemical or biological composition.

13. The method of claim 1, further comprising exposing the material located within the internal volume of the chamber to ultraviolet radiation.

14. The method of claim 13, wherein exposing the material located within the internal volume of the chamber to ultraviolet radiation occurs during the exposing of the material to focused acoustic energy.

15. A sample treatment apparatus, comprising:
a chamber defining an internal volume and having an inlet to receive an inflow of material into the internal volume and an outlet to discharge an outflow of material from the internal volume;

an acoustic energy source spaced from the chamber and arranged to emit acoustic energy having a frequency of about 100 kHz to 100 MHz to create a focal zone of acoustic energy in the internal volume; and at least one retaining member including a particle size filter constructed and arranged to retain a portion of the material at a region of the chamber based on whether the portion of the material has a characteristic that meets a criterion.

16. The apparatus of claim 15, wherein the characteristic is particle size of particles in the portion of the material, and the criterion is that the particle size of particles is above a threshold particle size.

17. The apparatus of claim 15, wherein the at least one retaining member is positioned at the inlet of the chamber to prevent the portion of the material from entering the internal volume of the chamber.

18. The apparatus of claim 15, wherein the at least one retaining member is positioned at the outlet of the chamber to prevent the portion of the material from exiting the internal volume of the chamber.

19. The apparatus of claim 15, wherein the characteristic is optical transmittance, and the criterion is that the portion of the material has an optical transmittance below a threshold transmittance value.

20. The apparatus of claim 15, wherein the characteristic is a chemical or biological characteristic, and the criterion is that the portion of the material has a sensed chemical or biological composition.

21. The apparatus of claim 15, further comprising one or more ultraviolet radiation sources arranged to emit ultraviolet radiation toward the internal volume.

* * * * *